United States Patent
Goodrich et al.

(10) Patent No.: US 11,237,156 B2
(45) Date of Patent: Feb. 1, 2022

(54) METHOD AND COMPOSITION FOR DETECTION OF PEPTIDE CYCLIZATION USING PROTEIN TAGS

(71) Applicant: Roche Sequencing Solutions, Inc., Pleasanton, CA (US)

(72) Inventors: Lauren Goodrich, Madison, WI (US); Jigar Patel, Madison, WI (US); Eric Sullivan, Madison, WI (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 15/677,633

(22) Filed: Aug. 15, 2017

(65) Prior Publication Data

US 2018/0045721 A1    Feb. 15, 2018

Related U.S. Application Data

(60) Provisional application No. 62/375,167, filed on Aug. 15, 2016.

(51) Int. Cl.
| | |
|---|---|
| *G01N 33/543* | (2006.01) |
| *C07K 7/64* | (2006.01) |
| *C07K 1/13* | (2006.01) |
| *C07K 1/04* | (2006.01) |
| *G01N 33/68* | (2006.01) |

(52) U.S. Cl.
CPC ....... *G01N 33/54306* (2013.01); *C07K 1/047* (2013.01); *C07K 1/13* (2013.01); *C07K 7/64* (2013.01); *G01N 33/54353* (2013.01); *G01N 33/6845* (2013.01); *B01J 2219/00439* (2013.01); *B01J 2219/00659* (2013.01); *B01J 2219/00725* (2013.01)

(58) Field of Classification Search
CPC ....... G01N 33/54306; G01N 33/54353; G01N 33/6845; C07K 1/047; C07K 1/13; C07K 7/64; B01J 2219/00439; B01J 2219/00659; B01J 2219/00725
See application file for complete search history.

(56) References Cited

U.S. PATENT DOCUMENTS

2007/0048806 A1*   3/2007   Charych ................ B82Y 15/00
                                                           435/7.2

FOREIGN PATENT DOCUMENTS

| WO | 2015097077 A2 | 7/2015 |
|---|---|---|
| WO | 2016/170107 A1 | 10/2016 |

OTHER PUBLICATIONS

Pepperprint ("High Resolution Conformational Epitope Mapping" website retrieved on Dec. 18, 2019 from archive.org, available on or before Mar. 20, 2015 and the referenced "Application Note" and "Detailed Report", 26 pages).*
Liu et al. (Bioorg. Med. Chem., 17 (2009), p. 1026-1033).*
Anonymous, High Resolution Conformational Epitope Mapping, retrieved from the internet, Jun. 28, 2016, URL: http://www.pepperprint.com/applications/conformational-epitope-mapping/?utm_source=CleverReach&utm medium=email&utm campaign=Testversand+RitUximab-Webinar+RerTlinder&utm content=Mailing_9151248.
Baxter et al. (Dec. 22, 2014) Future Medicinal Chemistry vol. 6, p. 2073-2092.
Blackwell, H.E., Hitting the SPOT: small-molecule macroarrays advance combinatorial synthesis, Current Opinion in Chemical Biology, (2006), pp. 203-212, vol. 10 Issue 3.
Database Biosis, Smart peptide libraries are accessible via enzymatic modifications, Database Biosis (online), (2001), -, PREV200200502416.
International preliminary search report dated Oct. 24, 2017 in corresponding PCT application PCT/EP2016/058998.
International Search report & written opinion dated Jul. 8, 2016 in corresponding PCT application No. PCT/EP2016/058998.
International Search Report & written opinion dated Nov. 17, 2017 in corresponding PCT application No. PCT/EP2017/070393; pp. 1 to 14.
Koivunen, E. et al., Tumor targeting with a selective gelatinase inhibitor, Nature Biotechnology, (1999), pp. 768-774, vol. 17 No. 8.
Laurent, N. et al., Enzyme catalysis on solid surfaces, Trends in Biotechnology, (2008), pp. 328-337, vol. 26 Issue 6.
Li, S. et al., Photolithographic synthesis of cyclic peptide arrays using a differential deprotection strategy, Chemical Communications, (2005), pp. 581-583, No. 5.
Liu, T. et al., Synthesis and screening of a cyclic peptide library: Discovery of small-molecule ligands against human prolactin receptor, Bioorganic & Medicinal Chemistry, (2009), pp. 1026-1033, vol. 17 Issue 3.
Marthandan, N., et al., Construction and Evaluation of an Automated Light Directed Protein-Detecting Microarray Synthesizer, IEEE Transact, on Nanobiosci., (2008), pp. 20-27, vol. 7.
Menegatti, S. et al., Reversible Cyclic Peptide Libraries for the Discovery of Affinity Ligands, Analytical Chemistry, (2013), pp. 9229-9237, vol. 85 No. 19.

(Continued)

*Primary Examiner* — Robert H Havlin
(74) *Attorney, Agent, or Firm* — Foley & Lardner LLP

(57) ABSTRACT

This invention relates to peptide microarrays, methods of generating peptide microarrays, and methods of identifying peptide binders using microarrays. More specifically, this invention relates to peptide microarrays, methods of generating peptide microarrays, and methods of identifying peptide binders using microarrays wherein the microarrays comprise cyclic peptides. The invention also relates to methods and compositions for detecting the formation of cyclized peptides from linear peptides on a microarray by contacting the microarray with a detectable protein. The cyclized peptides include tags that are activated upon cyclization, facilitating the detection of successful cyclization reactions. In additional aspects, the invention relates to developing fragmented peptide tags that, upon cyclization, bind to detectable proteins. Additionally, the invention relates to methods of generating linear and cyclic peptides subarrays on a microarray.

17 Claims, 33 Drawing Sheets

Specification includes a Sequence Listing.

(56) References Cited

OTHER PUBLICATIONS

Sang Hoon Joo, "Cyclic Peptides as Therapeutic Agents and Biochemical Tools", Biomolecular & Therapeutics, 2012, 19-26, 20(1).
Tanaka, Y. et al., Exploring enzymatic catalysis at a solid surface: a case study with transglutaminase-mediated protein immobilization, Organic and Biomolecular Chemistry, (2007), pp. 1764-1770, vol. 5 No. 11.
Timmerman, P. et al., A Combinatorial Approach for the Design of Complementarity-determining Region-derived Peptidomimetics with in Vitro Anti-tumoral Activity, JBC, (2009), p. 34126-34134, vol. 284 No. 49.
Zang, X. et al., Tight-binding streptavidin ligands from a cyclic peptide library, Bioorganic & Medicinal Chemistry Letters, (1998), pp. 2327-2332, vol. 8 Issue 17.
Zhang et al., "Cyclic peptidyl inhibitors of Grb2 and tension SH2 domains identified from combinational libraries" Journal of Combinatorial Chemistry vol. 10 p. 247-255 (2008).

* cited by examiner

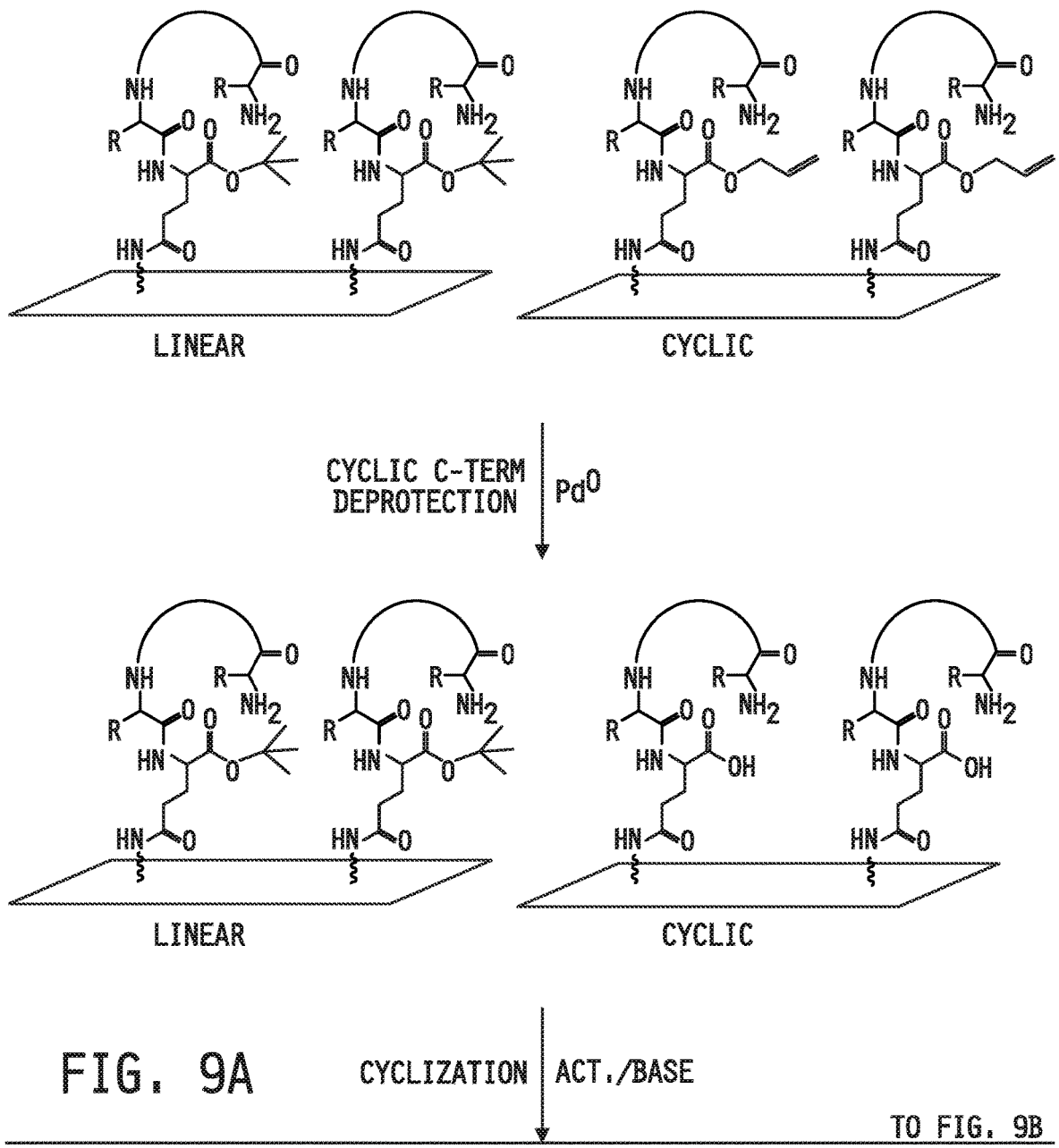
FIG. 9A  CYCLIZATION ACT./BASE
TO FIG. 9B

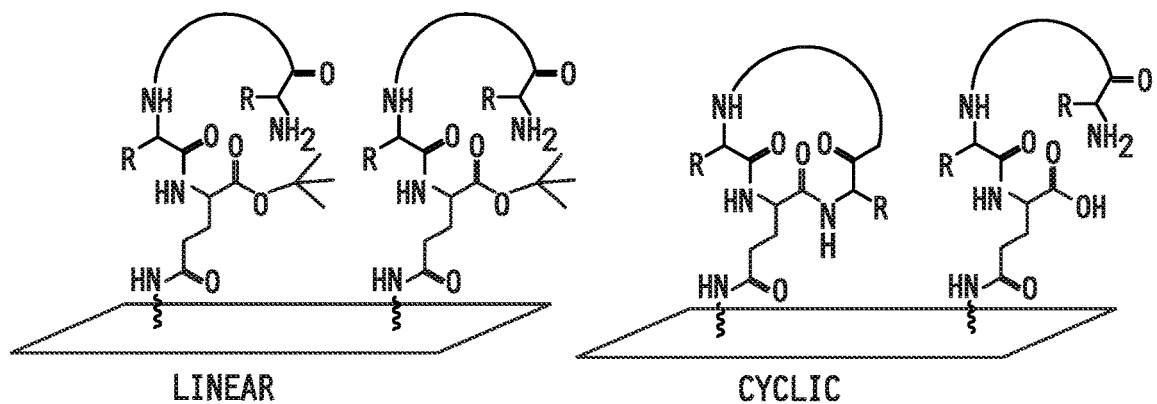
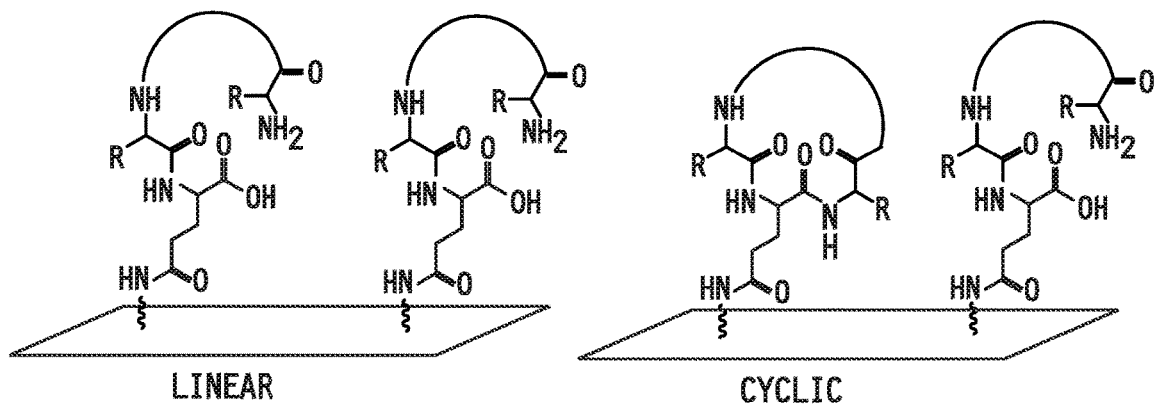
FIG. 9B

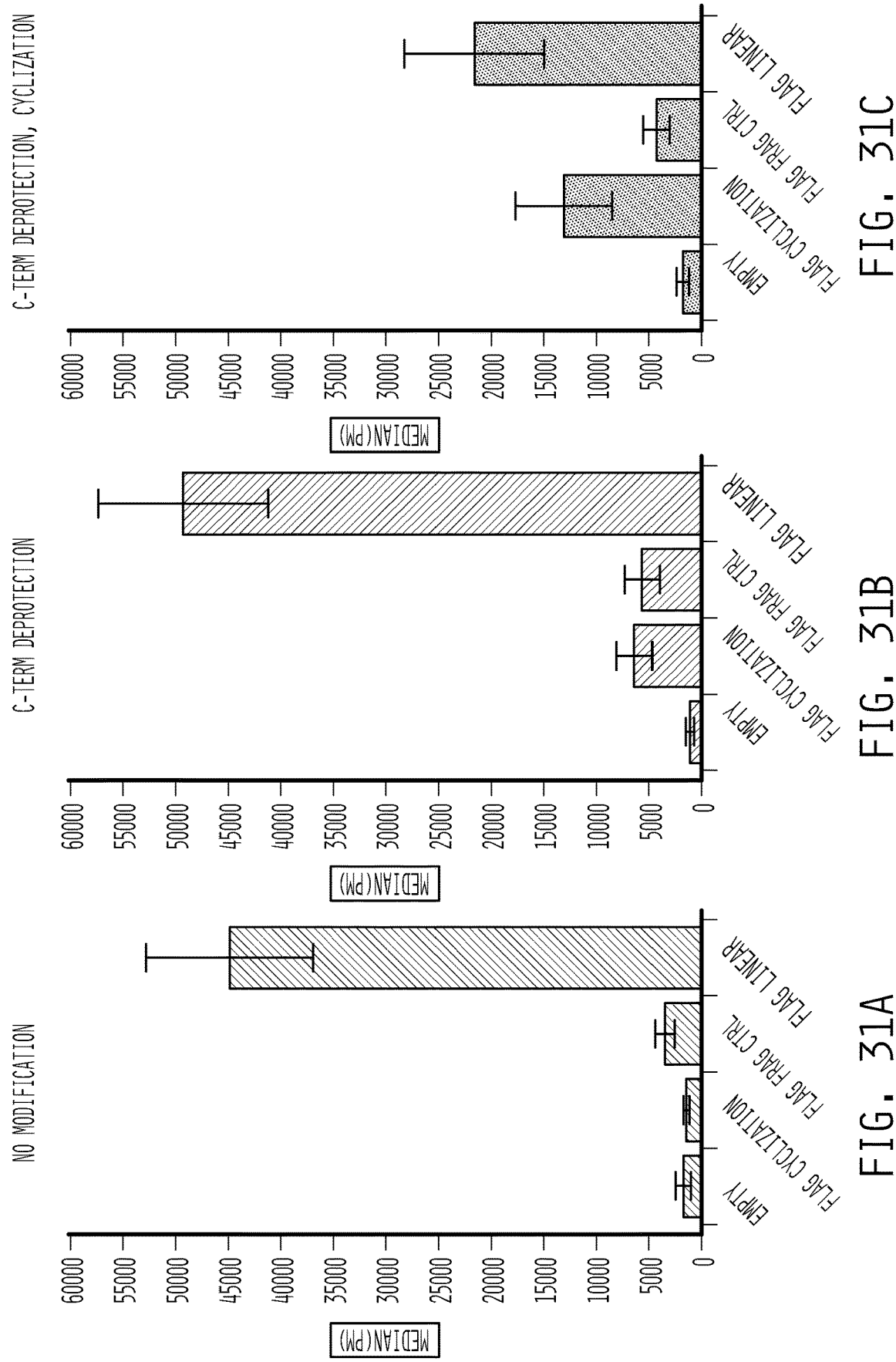

METHOD AND COMPOSITION FOR DETECTION OF PEPTIDE CYCLIZATION USING PROTEIN TAGS

CROSS REFERENCE TO RELATED APPLICATION

This application claims priority under 35 U.S.C. § 119(e) to U.S. Provisional Application Ser. No. 62/375,167, filed Aug. 15, 2016, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 28, 2017, is named 5727-267483_SL.txt and is 78,145 bytes in size.

TECHNICAL FIELD

This invention relates to peptide-coated surfaces such as peptide microarrays, methods of generating peptide-coated surfaces and microarrays, and methods of identifying peptide binders using peptide-coated surfaces and microarrays. More specifically, this invention relates to methods of detecting the formation of cyclized peptides from linear peptides on a surface by contacting the surface with a detectable protein. In some aspects, the cyclized peptides include tags that are activated upon cyclization, facilitating the detection of successful cyclization reactions. In additional aspects, the invention relates to developing fragmented peptide tags that, upon cyclization, bind to detectable proteins.

BACKGROUND

Understanding protein-protein interactions is important for basic research as well as various biomedical and other practical applications. Examples of this kind include binding between peptide fragments or epitopes and antibodies, the interaction between proteins and short fragments of other proteins, as well as binding between peptides referred to as aptamers to their target molecules. Development of simple and reliable methods for identifying peptide binders for proteins would help in understanding the mechanisms of protein-protein interaction and open new opportunities for drug discovery.

With the identification of cellular pathways and targets that play key roles in metabolism and disease progression, the understanding of disease states continues to expand exponentially. Although our understanding of diseases is advanced, our ability to treat them lags behind due to the limitations inherent in existing drug platforms. At present, the available drug platforms are based primarily on small molecules and therapeutic proteins, which address only about 10 to 20 percent of the identified therapeutic targets for treatment of diseases.

Peptides combine the high specificity of biological drugs with the bioavailability of small molecules, and, thus, offer exciting opportunities to address difficult targets for disease treatment. In fact, peptides have proven to be effective when used to target extracellular receptors, but can be limited by instability within the body and breakdown by circulating proteases. The concept of using peptides to modulate intracellular processes has been investigated for decades, yet these strategies have largely failed because peptides lack the ability to enter cells.

Cyclic peptides, with their conformational rigidity, may be advantageous relative to their linear peptide counterparts, such as improved target affinity and specificity. Their higher target specificity and affinity as well as resistance to proteolysis have made them attractive candidates for drug discovery. Cyclic peptides have been isolated from large combinatorial libraries using library screening tools, such as phage display and mRNA display, but improved methods are needed to screen large numbers of cyclic peptides, to mature cyclic peptides in situ, and to identify cyclic peptides of interest. Currently, there is no systematic approach to identifying and maturing cyclic peptides to obtain optimized cyclic peptide binders.

Another powerful method to study peptide-protein interactions is the use of peptide microarrays. Peptide microarrays can be made with peptides synthesized using solid phase peptide synthesis and then immobilized on a solid support or can be directly prepared by in situ synthesis methods. Although peptide microarrays are commercially available, their application is limited by a relatively low density of peptides and high cost of manufacturing. Both of these issues can be addressed by use of maskless light-directed technology, see (Pellois, Zhou et al. (2002) *Individually addressable parallel peptide synthesis on microchips.*) and U.S. Pat. No. 6,375,903.

Using an instrument for maskless light-directed microarray synthesis, the selection of peptide sequences to be constructed on the peptide microarray is under software control such that it is now possible to create individually-customized arrays based on the particular needs of an investigator. In general, maskless light-directed microarray synthesis technology allows for the parallel synthesis of millions of unique peptide features in a very small area of a standard microscope slide. The peptide microarrays are generally synthesized by using light to direct which peptides are synthesized at specific locations on the microarray.

There exists an unmet need for a more efficient and successful method of identifying therapeutic cyclic peptide candidates for existing and potential new drug targets, in part, because many targets and diseases are presently "undruggable" using existing therapeutic modalities. More generally, there is a need for systems and methods to study cyclic peptides, either alone, or alongside their linear counterparts. Further, there is a need for systems and methods to screen and identify cyclic peptide binders or substrates in an efficient and high-throughput manner.

Along with the above-mentioned needs, there is a need for systems and methods to identify and confirm the successful cyclization of linear peptides. Inefficient cyclization may be difficult to predict because cyclization reactions can be sequence specific. In situations where cyclization does not go to completion, the resulting mixture comprises linear and cyclic peptides, where the ratio of cyclic to linear peptides is not constant or simple to predict based on methods known in the art. The lack of available methods to determine whether cyclization is successful creates challenges in quality control when generating cyclic peptides.

SUMMARY

Applicants disclose herein novel peptide microarrays having peptides with tags for detecting cyclization, methods of generating peptide microarrays, methods of detecting and measuring the extent of peptide cyclization on peptide microarrays, and methods of identifying peptide binders using the microarrays described herein. Applicants also disclose herein methods for developing tags for detecting peptide cyclization. The tags are activated upon peptide cyclization by increasing their binding interaction with a detectable target protein, allowing for the detection of successful cyclization reactions. Specifically, the cyclic peptides described herein are formed from linear peptide precursors each having a fragmented peptide tag sequence, and portions of the peptide tag sequence are combined upon successful cyclization of the linear peptide precursors. After portions of the peptide tag sequence are combined, the cyclic peptide having the peptide tag sequence has an increased interaction with the detectable target protein compared to its linear form where the peptide tag sequence is fragmented. As such, the peptides described herein include tags for measuring the extent to which cyclization takes place. In some embodiments described herein, the cyclic peptides include segments that can be used as therapeutic peptides. Also disclosed herein are methods of designing and generating a peptide tag sequence for use in detecting cyclization of peptide microarrays.

Several embodiments of the invention are described by the following enumerated clauses:

1. A peptide microarray comprising at least one cyclic peptide coupled to a solid support, wherein the at least one cyclic peptide comprises a peptide tag sequence capable of binding to a detectable target protein.

2. The peptide microarray of clause 1, wherein the peptide tag sequence comprises an amino acid side chain coupled to the solid support.

3. The peptide microarray of clause 1 or 2, wherein the peptide tag sequence has at least 80% identity to WDYKD($R^4$)DQKGG (SEQ ID NO: 194) and wherein $R^4$ is an amino acid side chain coupled to the solid support.

4. The peptide microarray of any one of clauses 1 to 3, wherein the peptide tag sequence is WDYKD($R^4$)DQKGG (SEQ ID NO: 194) and $R^4$ is an amino acid side chain coupled to the solid support.

5. The peptide microarray of clause 1 or 2, wherein the peptide tag sequence has at least 80% identity to EQKLI($R^4$)EEDWG (SEQ ID NO: 195) and $R^4$ is an amino acid side chain coupled to the solid support.

6. The peptide microarray of clause 1, 2, or 5, wherein the peptide tag sequence is EQKLI($R^4$)EEDWG (SEQ ID NO: 195) and $R^4$ is an amino acid side chain coupled to the solid support.

7. The peptide microarray of clause 1, wherein the at least one cyclic peptide is of formula I

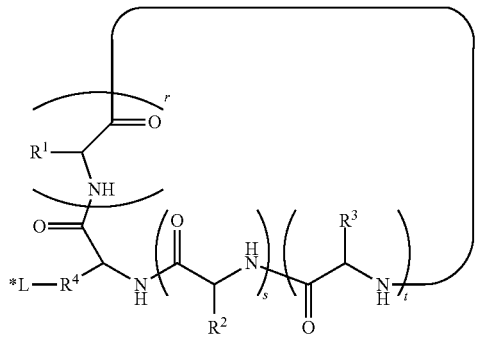

wherein each $R^1$, $R^2$, and $R^3$ is independently a natural amino acid side chain or a non-natural amino acid side chain;

$R^4$ is an amino acid side chain comprising a carboxylic acid, an alcohol, or an amine bonded to L;

L is a bivalent linking group;

each r and s is independently an integer from 1 to 50;

t is an integer from 0 to 50;

and * is a point of connection connecting the at least one cyclic peptide to the solid support, wherein each $R^1$, $R^2$, and $R^4$ is defined such that the at least one cyclic peptide comprises the peptide tag sequence.

8. The peptide microarray of any one of clauses 1 to 7, wherein the detectable target protein is an antibody against the peptide tag sequence.

9. The peptide microarray of any one of clauses 1 to 8, wherein the detectable target protein is a fluorescent protein.

10. The peptide microarray of clause 9, wherein the fluorescent protein is labeled with a cyanine dye.

11. The peptide microarray of clause 10, wherein the cyanine dye is Cy3 or Cy5.

12. The peptide microarray any one of clauses 1 to 11, wherein the peptide tag sequence is capable of binding selectively to the detectable target protein.

13. The peptide microarray of any one of clauses 1 to 12, wherein the detectable target protein is an anti-FLAG antibody or an anti-Myc antibody.

14. The peptide microarray of any one of clauses 7 to 13, wherein each r and s is independently an integer from 3 to 8.

15. The peptide microarray of any one of clauses 7 to 14, wherein s is 5.

16. The peptide microarray of any one of clauses 7 to 15, wherein r is 5.

17. The peptide microarray of any one of clauses 7 to 15, wherein r is 6.

18. The peptide microarray of any one of clauses 7 to 17, wherein the peptide tag sequence has at least 80% identity to WDYKD($R^4$)DQKGG (SEQ ID NO: 194).

19. The peptide microarray of any one of clauses 7 to 18, wherein the peptide tag sequence is WDYKD($R^4$)DQKGG (SEQ ID NO: 194).

20. The peptide microarray of any one of clauses 7 to 17, wherein the peptide tag sequence has at least 80% identity to EQKLI($R^4$)EEDWG (SEQ ID NO: 195).

21. The peptide microarray of any one of clauses 7 to 17 and 20, wherein the peptide tag sequence is EQKLI($R^4$)EEDWG (SEQ ID NO: 195).

22. The peptide microarray of any one of clauses 7 to 21, wherein $R^4$ and L form an ester or an amide.

23. The peptide microarray of any one of clauses 3 to 22, wherein $R^4$ is a glutamate side chain.

24. The peptide microarray of any one of clauses 7 to 23, wherein $R^4$ and L do not substantially interfere with the peptide tag sequence binding to the detectable target protein.

25. The peptide microarray of any one of clauses 7 to 24, wherein each $R^3$ is defined such that the at least one cyclic peptide comprises an amino acid sequence of interest.

26. The peptide microarray of clause 25, wherein the amino acid sequence of interest is capable of binding to a second target protein.

27. The peptide microarray of clause 26, wherein the second target protein is a therapeutic target.

28. The peptide microarray of any one of clauses 7 to 27, wherein t is an integer from 3 to 50.

29. The peptide microarray of any one of clauses 7 to 28, wherein t is an integer from 3 to 10.

30. The peptide microarray of any one of clauses 7 to 29, wherein t is the same for each cyclic peptide of the population of peptides.

31. The peptide microarray of any one of clauses 25 to 30, wherein the amino acid sequence of interest does not contain any of a methionine amino acid, a cysteine amino acid, an amino acid repeat of the same amino acid, or an amino acid motif consisting of a histidine (H)-proline (P)-glutamine (Q) sequence.

32. The peptide microarray of any one of clauses 1 to 31, wherein each cyclic peptide of the population of peptides comprises at least one of an N-terminal wobble synthesis oligopeptide or a C-terminal wobble synthesis oligopeptide.

33. The peptide microarray of clause 32, wherein the wobble synthesis oligopeptide of each cyclic peptide of the population of peptides comprises an amino acid sequence having the same number of amino acids.

34. The peptide microarray of clause 32 or 33, wherein the wobble synthesis oligopeptide of each peptide of the population of peptides is derived randomly from an amino acid mixture having each of the twenty amino acids or a subset of the twenty amino acids in approximately equal concentrations.

35. The peptide microarray of clause 32 or 33, wherein the wobble synthesis oligopeptide of each cyclic peptide of the population of peptides is derived randomly from an amino acid mixture having amino acids glycine (G) and serine (S) in approximately a 3 (G) to 1 (S) concentration.

36. The peptide microarray of any one of clauses 32 to 35, wherein there is a C-terminal and an N-terminal wobble synthesis oligopeptide and both the C-terminal and N-terminal wobble synthesis oligopeptides comprise the same number of five or more amino acids.

37. The peptide microarray of any one of clauses 7 to 36, wherein L is of the formula

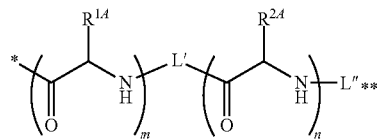

wherein each $R^{1A}$ and $R^{2A}$ is independently a natural amino acid side chain or a non-natural amino acid side chain;

each L' and L" is independently a bivalent linking group or a bond;

m is an integer from 0 to 6;

n is an integer from 0 to 6;

* is the point of connection connecting the at least one cyclic peptide to the solid support having the reactive surface;

and ** is a point of connection connecting L to the rest of the least one cyclic peptide. 38. The peptide microarray of clause 37, wherein each L' and L" is independently of the formula II

wherein each $R^8$ and $R^{8'}$ is independently selected from the group consisting of H, D, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^9$, —$OC(O)R^9$, —$NR^9R^{9'}$, —$NR^9C(O)R^{10}$, —$C(O)R^9$, —$C(O)OR^9$, and —$C(O)NR^9R^{9'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by halogen, $C_1$-$C_6$ alkyl, $C_2$-$C_6$ alkenyl, $C_2$-$C_6$ alkynyl, —$OR^{11}$; each $R^9$, $R^{9'}$, $R^{10}$, and $R^{11}$ is independently selected from the group consisting of H, D, hydroxyl, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl; and a is an integer from 1 to 10; or the formula III or IV

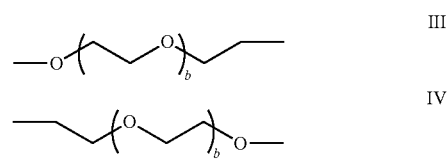

wherein b is an integer from 0 to 30.

39. The peptide microarray of clause 38, wherein each $R^8$ and $R^{8'}$ is hydrogen.

40. The peptide microarray of any one of clauses 37 to 39, wherein m is 0.

41. The peptide microarray of any one of clauses 37 to 40, wherein n is 0.

42. The peptide microarray of any one of clauses 37 to 41, wherein L is 6-aminohexanoic acid.

43. The peptide microarray of any one of clauses 1 to 42, wherein the solid support is selected from a group of materials consisting of plastic, glass, and carbon composite.

44. The peptide microarray of any one of clauses 7 to 43, wherein the solid support comprises an activated amine bonded to L.

45. A peptide microarray comprising at least one linear peptide coupled to a solid support, wherein the at least one linear peptide comprises a peptide tag sequence fragmented across a first end portion and a second end portion of the at least one linear peptide, wherein the binding interaction of the peptide tag sequence with a detectable target protein increases after the first end portion and the second end portion combine to cyclize the at least one linear peptide.

46. The peptide microarray of clause 45, wherein the peptide tag sequence comprises an amino acid side chain coupled to the solid support.

47. The peptide microarray of clause 46, wherein the C-terminus amino acid of the at least one cyclic peptide comprises the amino acid side chain coupled to the solid support.

48. The peptide microarray of clause 46 or 47, wherein the first end portion and the second end portion have higher specificities for binding to the detectable target protein compared to residue position of the amino acid side chain coupled to the solid support.

49. The peptide microarray of any one of clauses 45 to 48, wherein the peptide tag sequence has at least 80% identity to WDYKD($R^4$)DQKGG (SEQ ID NO: 194) and $R^4$ is an amino acid side chain coupled to the solid support.

50. The peptide microarray of any one of clauses 45 to 49, wherein the peptide tag sequence is WDYKD($R^4$)DQKGG (SEQ ID NO: 194) and $R^4$ is an amino acid side chain coupled to the solid support.

51. The peptide microarray of any one of clauses 45 to 48, wherein the peptide tag sequence has at least 80% identity to EQKLI(R⁴)EEDWG (SEQ ID NO: 195) and R⁴ is an amino acid side chain coupled to the solid support.

52. The peptide microarray of any one of clauses 45 to 48 and 51, wherein the peptide tag sequence is EQKLI(R⁴)EEDWG (SEQ ID NO: 195) and R⁴ is an amino acid side chain coupled to the solid support.

53. The peptide microarray of clause 45, wherein the at least one linear peptide is of formula II

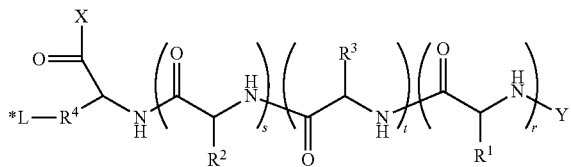

II wherein each $R^1$, $R^2$, and $R^3$ is independently a natural amino acid side chain or a non-natural amino acid side chain;

$R^4$ is an amino acid side chain comprising a carboxylic acid, an alcohol, or an amine bonded to L;

L is a bivalent linking group;

X is —OH or a C-terminal protecting group;

Y is hydrogen or an N-terminal protecting group;

each r and s is independently an integer from 1 to 50;

t is an integer from 0 to 50;

and * is a point of connection connecting the at least one cyclic peptide to the solid support, wherein each $R^1$, $R^2$, and $R^4$ is defined such that the at least one cyclic peptide comprises the peptide tag sequence.

54. The peptide microarray of any one of clauses 45 to 53, wherein the detectable target protein is an antibody against the peptide tag sequence.

55. The peptide microarray of any one of clauses 45 to 54, wherein the detectable target protein is a fluorescent protein.

56. The peptide microarray of clause 55, wherein the fluorescent protein is labeled with a cyanine dye.

57. The peptide microarray of clause 56, wherein the cyanine dye is Cy3 or Cy5.

58. The peptide microarray any one of clauses 45 to 57, wherein the peptide tag sequence is capable of binding selectively to the detectable target protein when the at least one linear peptide is cyclized.

59. The peptide microarray of any one of clauses 45 to 58, wherein the detectable target protein is an anti-FLAG antibody or an anti-Myc antibody.

60. The peptide microarray of any one of clauses 53 to 59, wherein each r and s is independently an integer from 3 to 8.

61. The peptide microarray of any one of clauses 53 to 60, wherein s is 5.

62. The peptide microarray of any one of clauses 53 to 61, wherein r is 5.

63. The peptide microarray of any one of clauses 53 to 61, wherein r is 6.

64. The peptide microarray of any one of clauses 53 to 63, wherein the peptide tag sequence has at least 80% identity to WDYKD(R⁴)DQKGG (SEQ ID NO: 194).

65. The peptide microarray of any one of clauses 53 to 64, wherein the peptide tag sequence is WDYKD(R⁴)DQKGG (SEQ ID NO: 194).

66. The peptide microarray of any one of clauses 53 to 63, wherein the peptide tag sequence has at least 80% identity to EQKLI(R⁴)EEDWG (SEQ ID NO: 195).

67. The peptide microarray of any one of clauses 53 to 64 and 66, wherein the peptide tag sequence is EQKLI(R⁴)EEDWG (SEQ ID NO: 195).

68. The peptide microarray of any one of clauses 53 to 67, wherein $R^4$ and L form an ester or an amide.

69. The peptide microarray of any one of clauses 53 to 68, wherein $R^4$ is a glutamate side chain.

70. The peptide microarray of any one of clauses 53 to 69, wherein $R^4$ and L do not substantially interfere with the peptide tag sequence binding to the detectable target protein.

71. The peptide microarray of any one of clauses 53 to 70, wherein each $R^3$ is defined such that the at least one cyclic peptide comprises an amino acid sequence of interest.

72. The peptide microarray of clause 71, wherein the amino acid sequence of interest is capable of binding to a second target protein.

73. The peptide microarray of clause 72, wherein the second target protein is a therapeutic target.

74. The peptide microarray of any one of clauses 53 to 73, wherein t is an integer from 3 to 50.

75. The peptide microarray of any one of clauses 53 to 74, wherein t is an integer from 3 to 10.

76. The peptide microarray of any one of clauses 53 to 75, wherein t is the same for each cyclic peptide of the population of peptides.

77. The peptide microarray of any one of clauses 71 to 76, wherein the amino acid sequence of interest does not contain any of a methionine amino acid, a cysteine amino acid, an amino acid repeat of the same amino acid, or an amino acid motif consisting of a histidine (H)-proline (P)-glutamine (Q) sequence.

78. The peptide microarray of any one of clauses 45 to 77, wherein each cyclic peptide of the population of peptides comprises at least one of an N-terminal wobble synthesis oligopeptide or a C-terminal wobble synthesis oligopeptide.

79. The peptide microarray of clause 78, wherein the wobble synthesis oligopeptide of each cyclic peptide of the population of peptides comprises an amino acid sequence having the same number of amino acids.

80. The peptide microarray of clause 78 or 79, wherein the wobble synthesis oligopeptide of each peptide of the population of peptides is derived randomly from an amino acid mixture having each of the twenty amino acids or a subset of the twenty amino acids in approximately equal concentrations.

81. The peptide microarray of clause 78 or 79, wherein the wobble synthesis oligopeptide of each cyclic peptide of the population of peptides is derived randomly from an amino acid mixture having amino acids glycine (G) and serine (S) in approximately a 3 (G) to 1 (S) concentration.

82. The peptide microarray of any one of clauses 78 to 81, wherein there is a C-terminal and an N-terminal wobble synthesis oligopeptide and both the C-terminal and N-terminal wobble synthesis oligopeptides comprise the same number of five or more amino acids.

83. The peptide microarray of any one of clauses 53 to 82, wherein L is of the formula

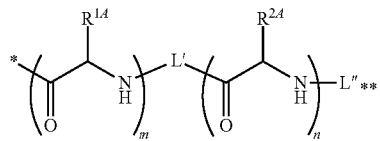

wherein each $R^{1A}$ and $R^{2A}$ is independently a natural amino acid side chain or a non-natural amino acid side chain;

each L' and L" is independently a bivalent linking group or a bond;

m is an integer from 0 to 6;

n is an integer from 0 to 6;

* is the point of connection connecting the at least one cyclic peptide to the solid support having the reactive surface;

and ** is a point of connection connecting L to the rest of the least one cyclic peptide. 84. The peptide microarray of clause 83, wherein each L' and L" is independently of the formula II

II wherein each $R^8$ and $R^{8'}$ is independently selected from the group consisting of H, D, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^9$, —$OC(O)R^9$, —$NR^9R^{9'}$, —$NR^9C(O)R^{10}$, —$C(O)R^9$, —$C(O)OR^9$, and —$C(O)NR^9R^{9'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by halogen, $C_1$-$C_6$ alkyl, $C_2$-$C_6$ alkenyl, $C_2$-$C_6$ alkynyl, —$OR^{11}$; each $R^9$, $R^{9'}$, $R^{10}$, and $R^{11}$ is independently selected from the group consisting of H, D, hydroxyl, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl; and a is an integer from 1 to 10; or the formula III or IV

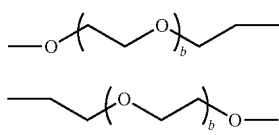

wherein b is an integer from 0 to 30.

85. The peptide microarray of clause 84, wherein each $R^8$ and $R^{8'}$ is hydrogen.

86. The peptide microarray of any one of clauses 83 to 85, wherein m is 0.

87. The peptide microarray of any one of clauses 83 to 86, wherein n is 0.

88. The peptide microarray of any one of clauses 83 to 87, wherein L is 6-aminohexanoic acid.

89. The peptide microarray of any one of clauses 45 to 88, wherein the solid support is selected from a group of materials consisting of plastic, glass, and carbon composite.

90. The peptide microarray of any one of clauses 53 to 89, wherein the solid support comprises an activated amine bonded to L.

91. The peptide microarray of any one of clauses 53 to 90, wherein X is OAll or OtBu.

92. The peptide microarray of any one of clauses 53 to 91, wherein Y is hydrogen.

93. A method of generating an oligopeptide tag, the method comprising a) providing a plurality of oligopeptides each comprising at least 5 amino acid residues and each having one of a plurality of modified sequences differing from a precursor sequence at 1 to 3 modified residue positions, b) measuring the binding interaction of each of the oligopeptides with a detectable target protein, c) optionally repeating steps a) and b) where one of the modified sequences is a subsequent precursor sequence, d) identifying a low specificity residue position having a lower specificity for binding to the detectable target protein compared to one or more of the other residues positions, and e) generating the oligopeptide tag having one of the modified sequences fragmented across a first end portion and a second end portion of the oligopeptide tag wherein the low specificity residue position is substituted with an amino acid having a side chain coupled to a solid surface, wherein the binding interaction of the peptide tag sequence with the detectable target protein increases after the first end portion and the second end portion combine to cyclize the at least one linear peptide.

94. The method of clause 93, wherein the low specificity residue position is the N-terminus or the C-terminus residue position of the oligopeptide tag.

95. The method of clause 93 or 94, wherein the low specificity residue position is the C-terminus residue position of the oligopeptide tag.

96. The method of any one of clauses 93 to 95, further comprising cyclizing the oligopeptide tag.

97. The method of clause 96, further comprising measuring the binding interaction of the oligopeptide tag with the detectable target protect after the cyclizing step.

98. The method of any one of clauses 93 to 97, wherein each of the modified sequences has an independently selected natural amino acid at each of the modified residue positions.

99. The method of any one of clauses 93 to 98, wherein each of the oligopeptides comprises 3 to 50 natural amino acid residues.

100. The method of any one of clauses 93 to 99, wherein each of the oligopeptides comprises 3 to 20 natural amino acid residues.

101. The method of any one of clauses 93 to 100, wherein each of the oligopeptides comprises 5 to 20 amino acids.

102. The method of any one of clauses 93 to 101, wherein each of the modified sequences differs from the precursor sequence at exactly 1 modified residue position.

103. The method of any one of clauses 93 to 102, wherein each sequence position is one of the modified residue positions in at least one of the oligopeptides.

104. The method of any one of clauses 93 to 103, wherein each of the oligopeptides has the same number of amino acid residues.

105. The method of any one of clauses 93 to 104, wherein the precursor sequence is based on a binding sequence for a known target.

106. The method of any one of clauses 93 to 105, wherein the precursor sequence has at least 80% identity to GDYKDDDDKGG (SEQ ID NO: 232).

107. The method of any one of clauses 93 to 106, wherein the precursor sequence is GDYKDDDDKGG (SEQ ID NO: 232).

108. The method of any one of clauses 93 to 105, wherein the precursor sequence has at least 80% identity to EQKLISEEDLG (SEQ ID NO: 233).

109. The method of any one of clauses 93 to 105 and 108, wherein the precursor sequence is EQKLISEEDLG (SEQ ID NO: 233).

110. A method of generating a peptide microarray comprising the at least one cyclic peptide of any one of clauses 1 to 44, the method comprising
a) generating the at least one linear peptide of any one of clauses 45-92;
b) treating the at least one linear peptide to form at least one deprotected linear peptide, and
c) treating the at least one deprotected linear peptide to form the at least one cyclic peptide.

111. The method of clause 110, wherein the at least one deprotected linear peptide is of formula III

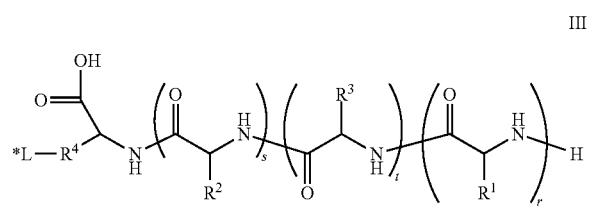

wherein each $R^1$, $R^2$, and $R^3$ is independently a natural amino acid side chain or a non-natural amino acid side chain;
$R^4$ is an amino acid side chain comprising a carboxylic acid, an alcohol, or an amine bonded to L;
L is a bivalent linking group;
each r and s is independently an integer from 1 to 50;
t is an integer from 0 to 50;
and * is a point of connection connecting the at least one cyclic peptide to the solid support.

112. The method of clause 110 or 111, wherein the C-terminal protecting group is OAll.

113. The method of any one of clauses 110 to 112, wherein treating the at least one linear peptide to form at least one deprotected linear peptide comprises contacting the at least one linear peptide with a palladium catalyst.

114. The method of clause 113, wherein the palladium catalyst is tetrakis(triphenylphosphine)palladium(0).

115. The method of any one of clauses 110 to 114, wherein treating the at least one deprotected linear peptide to form the at least one cyclic peptide comprises activating the carboxyl group of the C-terminus of the at least one deprotected linear peptide to react with the amino group of the N-terminus of the at least one deprotected linear peptide to form the peptide bond.

116. The method of any one of clauses 110 to 115, wherein treating the at least one deprotected linear peptide to form the at least one cyclic peptide comprises contacting the at least one deprotected linear peptide with HOBt and HBTU.

117. The method of any one of clauses 110 to 116, further comprising selecting the peptide tag sequence according to the method of any one of clauses 93 to 109.

118. A method of detecting peptide cyclization comprising
a) generating a peptide microarray according to the method of any one of clauses 110 to 117,
d) contacting the at least one cyclic peptide with the detectable target protein; and
e) detecting the presence of the detectable target protein that is bound to the at least one cyclic peptide.

119. The method of clause 118, wherein detecting the presence of the detectable target protein comprises spectrophotometry.

120. The method of clause 118 or 119, wherein detecting the presence of the detectable target protein comprises fluorescence spectroscopy.

121. The method of any one of clauses 118 to 120, further comprising removing the detectable target protein that is not bound to the at least one cyclic peptide prior to detecting the presence of the detectable target protein.

BRIEF DESCRIPTION OF THE DRAWINGS

FIG. 9 is a schematic view depicting a process for forming subarrays of linear and cyclic peptide libraries where the peptides of the cyclic library that fail to cyclize are the same as those of the linear library.

FIG. 15 discloses SEQ ID NOS 230-231, respectively, in order of appearance.

FIG. 31A is a chart showing signal intensity of anti-FLAG protein applied to an empty control, a cyclization tag before deprotection and cyclization, a fragmented control, and a linear control.

FIG. 31B is a chart showing signal intensity of anti-FLAG protein applied to an empty control, a cyclization tag after deprotection and before cyclization, a fragmented control, and a linear control.

FIG. 31C is a chart showing signal intensity of anti-FLAG protein applied to an empty control, a cyclization tag after cyclization, a fragmented control, and a linear control.

DETAILED DESCRIPTION OF ILLUSTRATIVE EMBODIMENTS

The instant disclosure provides peptide microarrays having peptides with tags for detecting cyclization and methods for using the same to detect and measure the extent of peptide cyclization. Applicants also disclose herein methods for developing tags for detecting peptide cyclization.

In some embodiments, this disclosure provides methods for identifying cyclic peptides where detection of peptide cyclization is desirable for quality control purposes. Such methods include, for example, methods of identifying therapeutic peptide binders (e.g., cyclic peptides) using microarrays by which novel peptide binders (e.g., cyclic peptides) can be synthesized, optimized and identified. In some embodiments, the final optimization step is cyclization according to the methods described herein after the peptide binders are matured and extended on the peptide microarray. Measuring the extent of completion of the cyclization step provides a better understanding of any assay results obtained from microarrays comprising the potential therapeutic peptide binders. In addition to comprising therapeutic portions, these exemplary peptide microarrays comprise cyclic peptides having peptide tags to allow for detection of cyclization. The peptide tags, which are initially fragmented, are activated upon cyclization, facilitating the detection of successful cyclization reactions.

According to further embodiments, the peptide microarrays disclosed herein may be used to identify therapeutic peptide binders (e.g., cyclic peptides) through identification of overlapping binding of the target of interest to small peptides comprising a comprehensive population of peptides immobilized on a peptide microarray, then performing an exhaustive peptide maturation of the isolated core binder sequence, followed by N-terminal and C-terminal extension procedures and, in one embodiment, followed by cyclization. Measuring the extent of completion of the cyclization step provides a better understanding of any assays performed using the potential therapeutic peptide binders. As such, in addition to comprising therapeutic portions, these exemplary cyclic peptides comprise the peptide tags described herein to allow for detection of cyclization. In some embodiments, the mature, extended core peptide binder sequence may be subjected to further maturation processes and a new series of N-terminal and C-terminal extension processes, and, for example, followed by cyclization.

Figure 24:
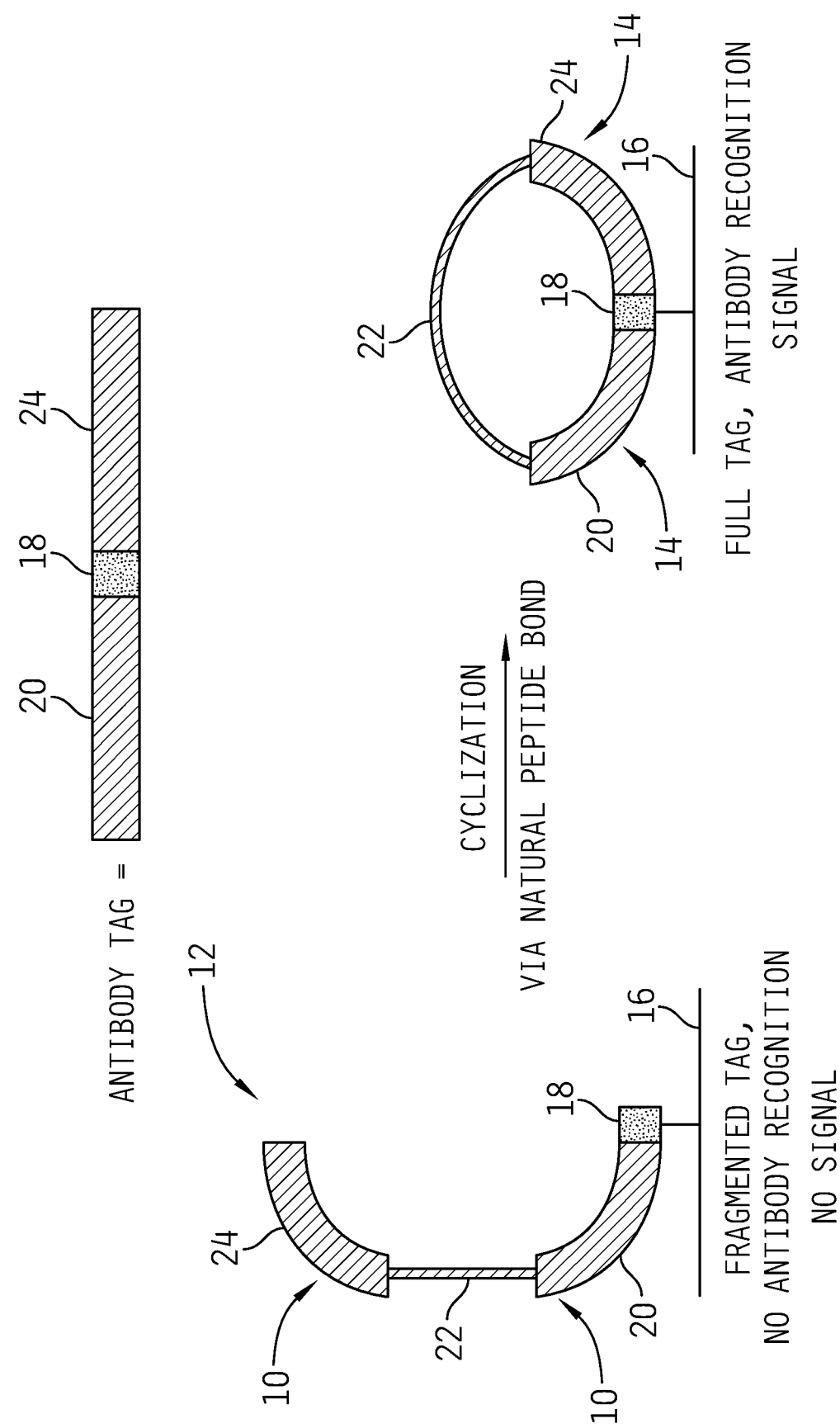
FIG. 24 is a schematic view showing a process for forming a full peptide tag in a cyclic peptide from a fragmented tag in a linear peptide.

The methods and compositions described herein make it possible to rapidly ensure that cyclization reactions to form the cyclic peptide libraries are successful. As shown in FIG. 24, a peptide tag is fragmented across the N- and C-termini of a linear peptide such that, upon cyclization, the full peptide tag is formed. After the full peptide tag is formed, peptide cyclization on the microarray can be detected by contacting the full peptide tag with a detectable protein. The detectable protein may be detectable by a variety of methods know in the art, including but not limited to spectroscopy. The methods described herein additionally allow for the development of peptide tags suitable for detecting peptide cyclization.

Several embodiments of the invention are described in the Summary section of this patent application and each of the embodiments described in this Detailed Description section of the application applies to the embodiments described in the Summary, including the embodiments described by the enumerated clauses below.

1. A peptide microarray comprising at least one cyclic peptide coupled to a solid support, wherein the at least one cyclic peptide comprises a peptide tag sequence capable of binding to a detectable target protein.

2. The peptide microarray of clause 1, wherein the peptide tag sequence comprises an amino acid side chain coupled to the solid support.

3. The peptide microarray of clause 1 or 2, wherein the peptide tag sequence has at least 80% identity to WDYKD($R^4$)DQKGG (SEQ ID NO: 194) and wherein $R^4$ is an amino acid side chain coupled to the solid support.

4. The peptide microarray of any one of clauses 1 to 3, wherein the peptide tag sequence is WDYKD($R^4$)DQKGG (SEQ ID NO: 194) and $R^4$ is an amino acid side chain coupled to the solid support.

5. The peptide microarray of clause 1 or 2, wherein the peptide tag sequence has at least 80% identity to EQKLI($R^4$)EEDWG (SEQ ID NO: 195) and $R^4$ is an amino acid side chain coupled to the solid support.

6. The peptide microarray of clause 1, 2, or 5, wherein the peptide tag sequence is EQKLI($R^4$)EEDWG (SEQ ID NO: 195) and $R^4$ is an amino acid side chain coupled to the solid support.

7. The peptide microarray of clause 1, wherein the at least one cyclic peptide is of formula I

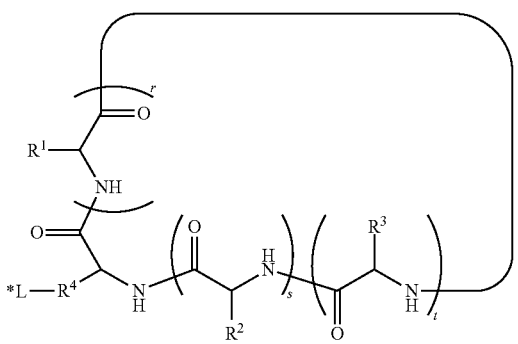

I wherein each $R^1$, $R^2$, and $R^3$ is independently a natural amino acid side chain or a non-natural amino acid side chain;

$R^4$ is an amino acid side chain comprising a carboxylic acid, an alcohol, or an amine bonded to L;

L is a bivalent linking group;

each r and s is independently an integer from 1 to 50;

t is an integer from 0 to 50;

and * is a point of connection connecting the at least one cyclic peptide to the solid support, wherein each $R^1$, $R^2$, and $R^4$ is defined such that the at least one cyclic peptide comprises the peptide tag sequence.

8. The peptide microarray of any one of clauses 1 to 7, wherein the detectable target protein is an antibody against the peptide tag sequence.

9. The peptide microarray of any one of clauses 1 to 8, wherein the detectable target protein is a fluorescent protein.

10. The peptide microarray of clause 9, wherein the fluorescent protein is labeled with a cyanine dye.

11. The peptide microarray of clause 10, wherein the cyanine dye is Cy3 or Cy5.

12. The peptide microarray any one of clauses 1 to 11, wherein the peptide tag sequence is capable of binding selectively to the detectable target protein.

13. The peptide microarray of any one of clauses 1 to 12, wherein the detectable target protein is an anti-FLAG antibody or an anti-Myc antibody.

14. The peptide microarray of any one of clauses 7 to 13, wherein each r and s is independently an integer from 3 to 8.

15. The peptide microarray of any one of clauses 7 to 14, wherein s is 5.

16. The peptide microarray of any one of clauses 7 to 15, wherein r is 5.

17. The peptide microarray of any one of clauses 7 to 15, wherein r is 6.

18. The peptide microarray of any one of clauses 7 to 17, wherein the peptide tag sequence has at least 80% identity to WDYKD($R^4$)DQKGG (SEQ ID NO: 194).

19. The peptide microarray of any one of clauses 7 to 18, wherein the peptide tag sequence is WDYKD($R^4$)DQKGG (SEQ ID NO: 194).

20. The peptide microarray of any one of clauses 7 to 17, wherein the peptide tag sequence has at least 80% identity to EQKLI($R^4$)EEDWG (SEQ ID NO: 195).

21. The peptide microarray of any one of clauses 7 to 17 and 20, wherein the peptide tag sequence is EQKLI($R^4$)EEDWG (SEQ ID NO: 195).

22. The peptide microarray of any one of clauses 7 to 21, wherein $R^4$ and L form an ester or an amide.

23. The peptide microarray of any one of clauses 3 to 22, wherein $R^4$ is a glutamate side chain.

24. The peptide microarray of any one of clauses 7 to 23, wherein $R^4$ and L do not substantially interfere with the peptide tag sequence binding to the detectable target protein.

25. The peptide microarray of any one of clauses 7 to 24, wherein each $R^3$ is defined such that the at least one cyclic peptide comprises an amino acid sequence of interest.

26. The peptide microarray of clause 25, wherein the amino acid sequence of interest is capable of binding to a second target protein.

27. The peptide microarray of clause 26, wherein the second target protein is a therapeutic target.

28. The peptide microarray of any one of clauses 7 to 27, wherein t is an integer from 3 to 50.

29. The peptide microarray of any one of clauses 7 to 28, wherein t is an integer from 3 to 10.

30. The peptide microarray of any one of clauses 7 to 29, wherein t is the same for each cyclic peptide of the population of peptides.

31. The peptide microarray of any one of clauses 25 to 30, wherein the amino acid sequence of interest does not contain any of a methionine amino acid, a cysteine amino acid, an amino acid repeat of the same amino acid, or an amino acid motif consisting of a histidine (H)-proline (P)-glutamine (Q) sequence.

32. The peptide microarray of any one of clauses 1 to 31, wherein each cyclic peptide of the population of peptides comprises at least one of an N-terminal wobble synthesis oligopeptide or a C-terminal wobble synthesis oligopeptide.

33. The peptide microarray of clause 32, wherein the wobble synthesis oligopeptide of each cyclic peptide of the population of peptides comprises an amino acid sequence having the same number of amino acids.

34. The peptide microarray of clause 32 or 33, wherein the wobble synthesis oligopeptide of each peptide of the population of peptides is derived randomly from an amino acid mixture having each of the twenty amino acids or a subset of the twenty amino acids in approximately equal concentrations.

35. The peptide microarray of clause 32 or 33, wherein the wobble synthesis oligopeptide of each cyclic peptide of the population of peptides is derived randomly from an amino acid mixture having amino acids glycine (G) and serine (S) in approximately a 3 (G) to 1 (S) concentration.

36. The peptide microarray of any one of clauses 32 to 35, wherein there is a C-terminal and an N-terminal wobble synthesis oligopeptide and both the C-terminal and N-terminal wobble synthesis oligopeptides comprise the same number of five or more amino acids.

37. The peptide microarray of any one of clauses 7 to 36, wherein L is of the formula

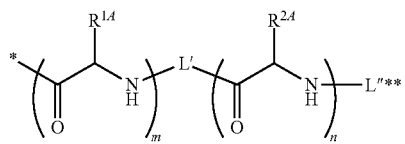

wherein each $R^{1A}$ and $R^{2A}$ is independently a natural amino acid side chain or a non-natural amino acid side chain;

each L' and L" is independently a bivalent linking group or a bond;

m is an integer from 0 to 6;

n is an integer from 0 to 6;

* is the point of connection connecting the at least one cyclic peptide to the solid support having the reactive surface;

and ** is a point of connection connecting L to the rest of the least one cyclic peptide. 38. The peptide microarray of clause 37, wherein each L' and L" is independently of the formula II

wherein each $R^8$ and $R^{8'}$ is independently selected from the group consisting of H, D, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^9$, —$OC(O)R^9$, —$NR^9R^{9'}$, —$NR^9C(O)R^{10}$, —$C(O)R^9$, —$C(O)OR^9$, and —$C(O)NR^9R^{9'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by halogen, $C_1$-$C_6$ alkyl, $C_2$-$C_6$ alkenyl, $C_2$-$C_6$ alkynyl, —$OR^{11}$; each $R^9$, $R^{9'}$, $R^{10}$, and $R^{11}$ is independently selected from the group consisting of H, D, hydroxyl, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl; and a is an integer from 1 to 10; or the formula III or IV

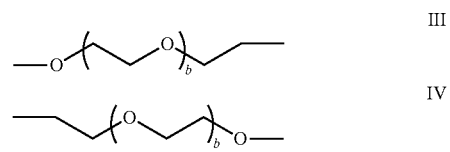

wherein b is an integer from 0 to 30.

39. The peptide microarray of clause 38, wherein each $R^8$ and $R^{8'}$ is hydrogen.

40. The peptide microarray of any one of clauses 37 to 39, wherein m is 0.

41. The peptide microarray of any one of clauses 37 to 40, wherein n is 0.

42. The peptide microarray of any one of clauses 37 to 41, wherein L is 6-aminohexanoic acid.

43. The peptide microarray of any one of clauses 1 to 42, wherein the solid support is selected from a group of materials consisting of plastic, glass, and carbon composite.

44. The peptide microarray of any one of clauses 7 to 43, wherein the solid support comprises an activated amine bonded to L.

45. A peptide microarray comprising at least one linear peptide coupled to a solid support, wherein the at least one linear peptide comprises a peptide tag sequence fragmented across a first end portion and a second end portion of the at least one linear peptide, wherein the binding interaction of the peptide tag sequence with a detectable target protein increases after the first end portion and the second end portion combine to cyclize the at least one linear peptide.

46. The peptide microarray of clause 45, wherein the peptide tag sequence comprises an amino acid side chain coupled to the solid support.

47. The peptide microarray of clause 46, wherein the C-terminus amino acid of the at least one cyclic peptide comprises the amino acid side chain coupled to the solid support.

48. The peptide microarray of clause 46 or 47, wherein the first end portion and the second end portion have higher specificities for binding to the detectable target protein compared to residue position of the amino acid side chain coupled to the solid support.

49. The peptide microarray of any one of clauses 45 to 48, wherein the peptide tag sequence has at least 80% identity to WDYKD($R^4$)DQKGG (SEQ ID NO: 194) and $R^4$ is an amino acid side chain coupled to the solid support.

50. The peptide microarray of any one of clauses 45 to 49, wherein the peptide tag sequence is WDYKD($R^4$)DQKGG (SEQ ID NO: 194) and $R^4$ is an amino acid side chain coupled to the solid support.

51. The peptide microarray of any one of clauses 45 to 48, wherein the peptide tag sequence has at least 80% identity to EQKLI($R^4$)EEDWG (SEQ ID NO: 195) and $R^4$ is an amino acid side chain coupled to the solid support.

52. The peptide microarray of any one of clauses 45 to 48 and 51, wherein the peptide tag sequence is EQKLI(R⁴)EEDWG (SEQ ID NO: 195) and R⁴ is an amino acid side chain coupled to the solid support.

53. The peptide microarray of clause 45, wherein the at least one linear peptide is of formula II

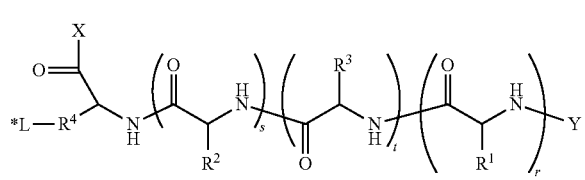

wherein each $R^1$, $R^2$, and $R^3$ is independently a natural amino acid side chain or a non-natural amino acid side chain;

$R^4$ is an amino acid side chain comprising a carboxylic acid, an alcohol, or an amine bonded to L;

L is a bivalent linking group;

X is —OH or a C-terminal protecting group;

Y is hydrogen or an N-terminal protecting group;

each r and s is independently an integer from 1 to 50;

t is an integer from 0 to 50;

and * is a point of connection connecting the at least one cyclic peptide to the solid support, wherein each $R^1$, $R^2$, and $R^4$ is defined such that the at least one cyclic peptide comprises the peptide tag sequence.

54. The peptide microarray of any one of clauses 45 to 53, wherein the detectable target protein is an antibody against the peptide tag sequence.

55. The peptide microarray of any one of clauses 45 to 54, wherein the detectable target protein is a fluorescent protein.

56. The peptide microarray of clause 55, wherein the fluorescent protein is labeled with a cyanine dye.

57. The peptide microarray of clause 56, wherein the cyanine dye is Cy3 or Cy5.

58. The peptide microarray any one of clauses 45 to 57, wherein the peptide tag sequence is capable of binding selectively to the detectable target protein when the at least one linear peptide is cyclized.

59. The peptide microarray of any one of clauses 45 to 58, wherein the detectable target protein is an anti-FLAG antibody or an anti-Myc antibody.

60. The peptide microarray of any one of clauses 53 to 59, wherein each r and s is independently an integer from 3 to 8.

61. The peptide microarray of any one of clauses 53 to 60, wherein s is 5.

62. The peptide microarray of any one of clauses 53 to 61, wherein r is 5.

63. The peptide microarray of any one of clauses 53 to 61, wherein r is 6.

64. The peptide microarray of any one of clauses 53 to 63, wherein the peptide tag sequence has at least 80% identity to WDYKD(R⁴)DQKGG (SEQ ID NO: 194).

65. The peptide microarray of any one of clauses 53 to 64, wherein the peptide tag sequence is WDYKD(R⁴)DQKGG (SEQ ID NO: 194).

66. The peptide microarray of any one of clauses 53 to 63, wherein the peptide tag sequence has at least 80% identity to EQKLI(R⁴)EEDWG (SEQ ID NO: 195).

67. The peptide microarray of any one of clauses 53 to 64 and 66, wherein the peptide tag sequence is EQKLI(R⁴)EEDWG (SEQ ID NO: 195).

68. The peptide microarray of any one of clauses 53 to 67, wherein $R^4$ and L form an ester or an amide.

69. The peptide microarray of any one of clauses 53 to 68, wherein $R^4$ is a glutamate side chain.

70. The peptide microarray of any one of clauses 53 to 69, wherein $R^4$ and L do not substantially interfere with the peptide tag sequence binding to the detectable target protein.

71. The peptide microarray of any one of clauses 53 to 70, wherein each $R^3$ is defined such that the at least one cyclic peptide comprises an amino acid sequence of interest.

72. The peptide microarray of clause 71, wherein the amino acid sequence of interest is capable of binding to a second target protein.

73. The peptide microarray of clause 72, wherein the second target protein is a therapeutic target.

74. The peptide microarray of any one of clauses 53 to 73, wherein t is an integer from 3 to 50.

75. The peptide microarray of any one of clauses 53 to 74, wherein t is an integer from 3 to 10.

76. The peptide microarray of any one of clauses 53 to 75, wherein t is the same for each cyclic peptide of the population of peptides.

77. The peptide microarray of any one of clauses 71 to 76, wherein the amino acid sequence of interest does not contain any of a methionine amino acid, a cysteine amino acid, an amino acid repeat of the same amino acid, or an amino acid motif consisting of a histidine (H)-proline (P)-glutamine (Q) sequence.

78. The peptide microarray of any one of clauses 45 to 77, wherein each cyclic peptide of the population of peptides comprises at least one of an N-terminal wobble synthesis oligopeptide or a C-terminal wobble synthesis oligopeptide.

79. The peptide microarray of clause 78, wherein the wobble synthesis oligopeptide of each cyclic peptide of the population of peptides comprises an amino acid sequence having the same number of amino acids.

80. The peptide microarray of clause 78 or 79, wherein the wobble synthesis oligopeptide of each peptide of the population of peptides is derived randomly from an amino acid mixture having each of the twenty amino acids or a subset of the twenty amino acids in approximately equal concentrations.

81. The peptide microarray of clause 78 or 79, wherein the wobble synthesis oligopeptide of each cyclic peptide of the population of peptides is derived randomly from an amino acid mixture having amino acids glycine (G) and serine (S) in approximately a 3 (G) to 1 (S) concentration.

82. The peptide microarray of any one of clauses 78 to 81, wherein there is a C-terminal and an N-terminal wobble synthesis oligopeptide and both the C-terminal and N-terminal wobble synthesis oligopeptides comprise the same number of five or more amino acids.

83. The peptide microarray of any one of clauses 53 to 82, wherein L is of the formula

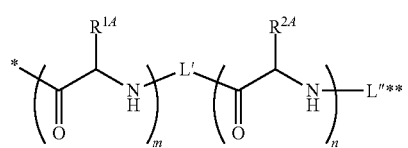

wherein each $R^{1A}$ and $R^{2A}$ is independently a natural amino acid side chain or a non-natural amino acid side chain;

each L' and L" is independently a bivalent linking group or a bond;

m is an integer from 0 to 6;

n is an integer from 0 to 6;

* is the point of connection connecting the at least one cyclic peptide to the solid support having the reactive surface;

and ** is a point of connection connecting L to the rest of the least one cyclic peptide.

84. The peptide microarray of clause 83, wherein each L' and L" is independently of the formula II $$-(CR^8R^{8'})_a- \quad \text{II}$$

wherein each $R^8$ and $R^{8'}$ is independently selected from the group consisting of H, D, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^9$, —$OC(O)R^9$, —$NR^9R^{9'}$, —$NR^9C(O)R^{10}$, —$C(O)R^9$, —$C(O)OR^9$, and —$C(O)NR^9R^{9'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by halogen, $C_1$-$C_6$ alkyl, $C_2$-$C_6$ alkenyl, $C_2$-$C_6$ alkynyl, —$OR^{11}$; each $R^9$, $R^{9'}$, $R^{10}$, and $R^{11}$ is independently selected from the group consisting of H, D, hydroxyl, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl; and a is an integer from 1 to 10; or the formula III or IV $$-O-(-O-)_b- \quad \text{III}$$

$$-(-O-)_b-O- \quad \text{IV}$$

wherein b is an integer from 0 to 30.

85. The peptide microarray of clause 84, wherein each $R^8$ and $R^{8'}$ is hydrogen.

86. The peptide microarray of any one of clauses 83 to 85, wherein m is 0.

87. The peptide microarray of any one of clauses 83 to 86, wherein n is 0.

88. The peptide microarray of any one of clauses 83 to 87, wherein L is 6-aminohexanoic acid.

89. The peptide microarray of any one of clauses 45 to 88, wherein the solid support is selected from a group of materials consisting of plastic, glass, and carbon composite.

90. The peptide microarray of any one of clauses 53 to 89, wherein the solid support comprises an activated amine bonded to L.

91. The peptide microarray of any one of clauses 53 to 90, wherein X is OAll or OtBu.

92. The peptide microarray of any one of clauses 53 to 91, wherein Y is hydrogen.

93. A method of generating an oligopeptide tag, the method comprising a) providing a plurality of oligopeptides each comprising at least 5 amino acid residues and each having one of a plurality of modified sequences differing from a precursor sequence at 1 to 3 modified residue positions, b) measuring the binding interaction of each of the oligopeptides with a detectable target protein, c) optionally repeating steps a) and b) where one of the modified sequences is a subsequent precursor sequence, d) identifying a low specificity residue position having a lower specificity for binding to the detectable target protein compared to one or more of the other residues positions, and e) generating the oligopeptide tag having one of the modified sequences fragmented across a first end portion and a second end portion of the oligopeptide tag wherein the low specificity residue position is substituted with an amino acid having a side chain coupled to a solid surface, wherein the binding interaction of the peptide tag sequence with the detectable target protein increases after the first end portion and the second end portion combine to cyclize the at least one linear peptide.

94. The method of clause 93, wherein the low specificity residue position is the N-terminus or the C-terminus residue position of the oligopeptide tag.

95. The method of clause 93 or 94, wherein the low specificity residue position is the C-terminus residue position of the oligopeptide tag.

96. The method of any one of clauses 93 to 95, further comprising cyclizing the oligopeptide tag.

97. The method of clause 96, further comprising measuring the binding interaction of the oligopeptide tag with the detectable target protect after the cyclizing step.

98. The method of any one of clauses 93 to 97, wherein each of the modified sequences has an independently selected natural amino acid at each of the modified residue positions.

99. The method of any one of clauses 93 to 98, wherein each of the oligopeptides comprises 3 to 50 natural amino acid residues.

100. The method of any one of clauses 93 to 99, wherein each of the oligopeptides comprises 3 to 20 natural amino acid residues.

101. The method of any one of clauses 93 to 100, wherein each of the oligopeptides comprises 5 to 20 amino acids.

102. The method of any one of clauses 93 to 101, wherein each of the modified sequences differs from the precursor sequence at exactly 1 modified residue position.

103. The method of any one of clauses 93 to 102, wherein each sequence position is one of the modified residue positions in at least one of the oligopeptides.

104. The method of any one of clauses 93 to 103, wherein each of the oligopeptides has the same number of amino acid residues.

105. The method of any one of clauses 93 to 104, wherein the precursor sequence is based on a binding sequence for a known target.

106. The method of any one of clauses 93 to 105, wherein the precursor sequence has at least 80% identity to GDYKDDDDKGG (SEQ ID NO: 232).

107. The method of any one of clauses 93 to 106, wherein the precursor sequence is GDYKDDDDKGG (SEQ ID NO: 232).

108. The method of any one of clauses 93 to 105, wherein the precursor sequence has at least 80% identity to EQKLISEEDLG (SEQ ID NO: 233).

109. The method of any one of clauses 93 to 105 and 108, wherein the precursor sequence is EQKLISEEDLG (SEQ ID NO: 233).

110. A method of generating a peptide microarray comprising the at least one cyclic peptide of any one of clauses 1 to 44, the method comprising
a) generating the at least one linear peptide of any one of clauses 45-92;
b) treating the at least one linear peptide to form at least one deprotected linear peptide, and
c) treating the at least one deprotected linear peptide to form the at least one cyclic peptide.

111. The method of clause 110, wherein the at least one deprotected linear peptide is of formula III

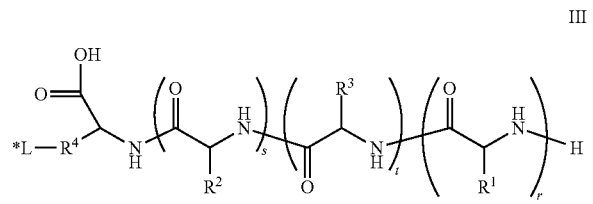

wherein each $R^1$, $R^2$, and $R^3$ is independently a natural amino acid side chain or a non-natural amino acid side chain;
$R^4$ is an amino acid side chain comprising a carboxylic acid, an alcohol, or an amine bonded to L;
L is a bivalent linking group;
each r and s is independently an integer from 1 to 50;
t is an integer from 0 to 50;
and * is a point of connection connecting the at least one cyclic peptide to the solid support.

112. The method of clause 110 or 111, wherein the C-terminal protecting group is OAll.

113. The method of any one of clauses 110 to 112, wherein treating the at least one linear peptide to form at least one deprotected linear peptide comprises contacting the at least one linear peptide with a palladium catalyst.

114. The method of clause 113, wherein the palladium catalyst is tetrakis(triphenylphosphine)palladium(0).

115. The method of any one of clauses 110 to 114, wherein treating the at least one deprotected linear peptide to form the at least one cyclic peptide comprises activating the carboxyl group of the C-terminus of the at least one deprotected linear peptide to react with the amino group of the N-terminus of the at least one deprotected linear peptide to form the peptide bond.

116. The method of any one of clauses 110 to 115, wherein treating the at least one deprotected linear peptide to form the at least one cyclic peptide comprises contacting the at least one deprotected linear peptide with HOBt and HBTU.

117. The method of any one of clauses 110 to 116, further comprising selecting the peptide tag sequence according to the method of any one of clauses 93 to 109.

118. A method of detecting peptide cyclization comprising
a) generating a peptide microarray according to the method of any one of clauses 110 to 117,
d) contacting the at least one cyclic peptide with the detectable target protein; and
e) detecting the presence of the detectable target protein that is bound to the at least one cyclic peptide.

119. The method of clause 118, wherein detecting the presence of the detectable target protein comprises spectrophotometry.

120. The method of clause 118 or 119, wherein detecting the presence of the detectable target protein comprises fluorescence spectroscopy.

121. The method of any one of clauses 118 to 120, further comprising removing the detectable target protein that is not bound to the at least one cyclic peptide prior to detecting the presence of the detectable target protein.

It is to be understood that generating cyclic peptide libraries on a microarray can be challenging when the precursor linear peptides have inefficient cyclization reactions that fail to go to completion, leading to mixtures of linear and cyclic peptides. Inefficient cyclization may be difficult to detect because the cyclization reaction can be sequence specific. In situations where cyclization does not go to completion, the resulting mixture comprises linear and cyclic peptides, where the ratio of cyclic to linear peptides is not constant or simple to predict based on methods known in the art. The lack of available methods to determine whether cyclization is successful creates challenges in quality control when generating cyclic peptide libraries. However, by verifying the extent to which cyclization is successful using the tags and methods disclosed herein, any inefficiency in cyclization can be taken into account, and peptide libraries can be used to produce more reliable data.

To make it possible to measure cyclization efficiency and detect successful cyclization, a peptide tag is included in cyclic peptides described herein. The peptide tag is fragmented across the N- and C-termini of a linear peptide such that, upon cyclization, the full peptide tag is formed. As such, while the peptide tag in more weakly detected or not detected in the linear peptide, upon cyclization the tag produces a stronger signal and after being contacted with a detectable target protein. Specifically, the peptide tag of the cyclic peptide is detected after binding to its corresponding detectable target protein, which may be a fluorescently-labelled protein. It is contemplated that such peptide tags may be incorporated into the various cyclic peptides and their linear precursors that are described herein.

In some embodiments, a method is provided for selecting an oligopeptide tag sequence that can be used as a peptide tag in a cyclic peptide and identifying a residue position for attaching the cyclic peptide to a microarray. Coupling a residue on the peptide tag to the microarray surface presents challenges in maintaining binding affinity and binding selectivity to a detectable target protein. Despite these challenges, the methods described herein allow for the design of an oligopeptide tag sequence that is coupled to a microarray and selectively binds to a detectable target protein. The methodology can be applied to design new peptide tags or further optimize peptides tags suitable for detection of peptide cyclization. Each amino acid in a peptide is substituted with other amino acids, such as but not limited to each of the remaining 19 amino acids, and the most favorable amino acid for increasing binding may be selected for various positions. The process may be repeated until the desired specificity at each position was achieved. A position having low specificity for binding is selected for substitution to an amino acid having a side chain that binds to a microarray. The side chain may be a carboxylic acid side chain such as a glutamate side chain.

In some embodiments and especially when cyclization is inefficient, a step can be performed to increase the proportion of cyclized peptides on a microarray relative to linear peptides on the peptide microarray. In this aspect, the peptide microarray comprises one or more linear peptides, along with cyclic peptides due to the inefficiency of cyclization. Thus, in this aspect, the cyclization method can further comprise the step of contacting the one or more linear peptides on the peptide microarray with a protease capable of digesting the one or more linear peptides. In this embodiment, the steps of the maturation/extension/cyclization method described herein can then be repeated after proteolytic digestion to increase the yield of cyclic peptides on the peptide microarray. It is to be understood that the peptide tags described herein may allow for detection of the extent of cyclization and determination of whether the yield of cyclized peptides should be increased.

In some embodiments, instead of increasing the yield of cyclization or purifying cyclic peptides from their linear precursors, the cyclic peptides are formed alongside a linear standard. As described in greater detail below, by generating linear peptides identical to the peptides that fail to cyclize, interactions of the linear peptides with a target protein are possible to measure. Therefore, differences between linear and cyclic peptides of the same sequence can be measured to identify peptides with high cyclic activity.

In one illustrative embodiment, the protease can be an aminoprotease, such as aminopeptidase m, cystinyl aminopeptidase, glutamyl aminopeptidase, leucyl aminopeptidase, or pyroglutamyl peptidase, or a mixture of aminoproteases. In another illustrative aspect, the protease can be a dipeptidase, such as dipeptidyl peptidase IV, a carboxypeptidase, a tripeptidylpeptidase, a metalloexopeptidase, or a combination thereof.

In the various embodiments described herein cyclic peptides are developed for binding to a target of interest, which may be, for example, a therapeutic target. As further described below, in such embodiments the cyclic peptides comprise both a tag sequence and an additional binding sequence for binding to the target of interest. The target of interest may be any molecule, including, but not limited to, a biomacromolecule such as a protein, a peptide, a nucleic acid (e.g., DNA or RNA), a polycarbohydrate, or a small molecule such as an organic compound or an organometallic complex, or any other molecule that contributes to a disease, such as the diseases listed below (e.g., a receptor for a therapeutic peptide, an enzyme inhibited or activated by a therapeutic peptide, or any other molecule wherein the activity of the molecule is altered by a therapeutic peptide). In one embodiment, the target of interest can be a molecule involved in a disease state and the cyclic peptide can be a therapeutic peptide.

In the embodiment where the cyclic peptide is a therapeutic peptide, the disease that is treated can be selected from the group consisting of cancer, an infectious disease, heart disease (e.g., atherosclerosis) and other cholesterol-related diseases, stroke, wounds, pain, an inflammatory disease, such as arthritis (e.g., rheumatoid arthritis), inflammatory bowel disease, psoriasis, diabetes mellitus, or an autoimmune disease, a respiratory disease, such as asthma or chronic obstructive pulmonary disease, diarrheal diseases, a genetic disease, a neurological disorder, such as Alzheimer's disease, muscular dystrophy, or Parkinson's disease, a mental disorder, or any other type of disease capable of being treated with a therapeutic peptide (e.g., a cyclic peptide).

In other embodiments, the disease can be a cancer selected from the group consisting of a carcinoma, a sarcoma, a lymphoma, a melanoma, a mesothelioma, a nasopharyngeal carcinoma, a leukemia, an adenocarcinoma, and a myeloma. In yet other embodiments, the disease can be a cancer selected from the group consisting of lung cancer, bone cancer, pancreatic cancer, skin cancer, cancer of the head or neck, melanoma, uterine cancer, ovarian cancer, endometrial cancer, rectal cancer, stomach cancer, colon cancer, breast cancer, cancer of the cervix, Hodgkin's Disease, cancer of the esophagus, non-small cell lung cancer, prostate cancer, leukemia, lymphoma, mesothelioma, cancer of the bladder, Burkitt's lymphoma, kidney cancer, and brain cancer, or any other type of cancer that can be treated with a therapeutic peptide (e.g., a cyclic peptide).

In one embodiment of the maturation/extension/cyclization method described herein, an isopeptide bond can be formed to cyclize peptides on the peptide microarray. In one aspect, the amino acids that can be linked can be a glutamine residue and a lysine residue in the same peptide, and the linkage can be formed using a transglutaminase.

In this embodiment, the glutamine-containing portion of the peptide can comprise a sequence motif of GDYALQGPG (SEQ ID NO: 1). In the embodiment where the sequence motif is GDYALQGPG (SEQ ID NO: 1), the glutamine-containing portion of the peptide can comprise a sequence selected from the group consisting of CGGDYALQGPG (SEQ ID NO:2), WGGDYALQGPG (SEQ ID NO:3), YGGDYALQGPG (SEQ ID NO:4), DGGDYALQGPG (SEQ ID NO:5), GDGDYALQGPG (SEQ ID NO:6), NGGDYALQGPG (SEQ ID NO:7), GCGDYALQGPG (SEQ ID NO:8), EGGDYALQGPG (SEQ ID NO:9), PGGDYALQGPG (SEQ ID NO:10), TGGDYALQGPG (SEQ ID NO:11), QGGDYALQGPG (SEQ ID NO:12), IGGDYALQGPG (SEQ ID NO:13), FGGDYALQGPG (SEQ ID NO:14), HGGDYALQGPG (SEQ ID NO:15), LGGDYALQGPG (SEQ ID NO:16), VGGDYALQGPG (SEQ ID NO:17), RGGDYALQGPG (SEQ ID NO:18), GWGDYALQGPG (SEQ ID NO:19), MGGDYALQGPG (SEQ ID NO:20), SGGDYALQGPG (SEQ ID NO:21), AGGDYALQGPG (SEQ ID NO:22), GYGDYALQGPG (SEQ ID NO:23), GEGDYALQGPG (SEQ ID NO:24), GPGDYALQGPG (SEQ ID NO:25), GHGDYALQGPG (SEQ ID NO:26), and GNGDYALQGPG (SEQ ID NO:27), or a combination thereof. In another embodiment, the glutamine-containing portion of the peptide can comprise the sequence DYALQ (SEQ ID NO: 28).

In another embodiment, the glutamine-containing portion of the peptide can comprise a sequence selected from the group consisting of GGGDYALQGGG (SEQ ID NO:29), WDGDYALQGGG (SEQ ID NO:30), GGGGDYALQGGGG (SEQ ID NO: 31), and GGGDYALQGGGG (SEQ ID NO: 32), or a combination thereof. In another embodiment, the glutamine-containing portion of the peptide can comprise the sequence GGGDYALQGGG (SEQ ID NO: 29).

In yet another embodiment, the glutamine-containing portion of the peptide can comprise a sequence motif of [YF][VA]LQG (SEQ ID NO: 33). In this embodiment, the glutamine-containing portion of the peptide can comprise a sequence selected from the group consisting of DYALQ (SEQ ID NO:34), DYVLQ (SEQ ID NO:35), NYALQ (SEQ ID NO:36), EYALQ (SEQ ID NO:37), PYALQ (SEQ ID NO:38), EYVLQ (SEQ ID NO:39), DFALQ (SEQ ID NO:40), FYALQ (SEQ ID NO:41), NYVLQ (SEQ ID NO:42), RYALQ (SEQ ID NO:43), YFALQ (SEQ ID NO:44), PYVLQ (SEQ ID NO:45), WYALQ (SEQ ID NO:46), SYALQ (SEQ ID NO:47), HYALQ (SEQ ID NO:48), EFALQ (SEQ ID NO:49), and NFVLQ (SEQ ID NO:50), or a combination thereof.

In still another illustrative aspect, the glutamine-containing portion of the peptide can comprise a sequence selected from the group consisting of DYFLQ (SEQ ID NO:51), EYVAQ (SEQ ID NO:52), DYVAQ (SEQ ID NO:53), DFYLQ (SEQ ID NO:54), EYFLQ (SEQ ID NO:55), or a combination thereof.

In yet another embodiment, the peptide can contain a lysine and the lysine-containing portion of the peptide can comprise a sequence motif of SK[LS]K (SEQ ID NO: 56) or [KR][ST]KL (SEQ ID NO: 57). In this embodiment, the lysine-containing portion of the peptide can comprise a sequence selected from the group consisting of ARSKL (SEQ ID NO:58), KSKLA (SEQ ID NO:59), TKSKL (SEQ ID NO:60), KLSKL (SEQ ID NO:61), RSKLG (SEQ ID NO:62), RGSKL (SEQ ID NO:63), RSKSK (SEQ ID NO:64), SKSKL (SEQ ID NO:65), PKTKL (SEQ ID NO:66), RSKLA (SEQ ID NO:67), GRSKL (SEQ ID NO:68), SKLSK (SEQ ID NO:69), FTKSK (SEQ ID NO:70), RLKSK (SEQ ID NO:71), KLGAK (SEQ ID NO:72), QRSKL (SEQ ID NO:73), LSKLK (SEQ ID NO:74), NRTKL (SEQ ID NO:75), QRTKL (SEQ ID NO:76), GGGRSKLAGGG (SEQ ID NO: 77), and GGGARSKLGGGG (SEQ ID NO: 78), or a combination thereof.

In another illustrative embodiment, the peptide can contain a lysine and the lysine-containing portion of the peptide can comprise a sequence selected from the group consisting of RGTKL (SEQ ID NO:196), FPKLK (SEQ ID NO:197), KLKYK (SEQ ID NO:198), RAKYK (SEQ ID NO:199), KTKYK (SEQ ID NO:200), and GYKLK (SEQ ID NO:201), or a combination thereof.

In still another embodiment, the peptide can comprise a transglutaminase glutamine substrate peptide and a transglutaminase lysine substrate peptide. In yet another embodiment, the transglutaminase glutamine and/or lysine substrate peptide can comprise a sequence of DYALQ (SEQ ID NO: 34) or can have a sequence motif comprising [FY][FYT]LQ (SEQ ID NO: 79), [YF]VAQ (SEQ ID NO: 80), K[YLS]K (SEQ ID NO: 81), or TKL (SEQ ID NO: 82).

In another embodiment, transglutaminase substrate peptides are contemplated having about 60%, about 70%, about 75%, about 80%, about 85%, about 90%, about 95%, about 96%, about 97%, about 98%, or about 99% homology with any of SEQ ID NOS: 4 to 82. Determination of percent identity or similarity between sequences can be done, for example, by using the GAP program (Genetics Computer Group, software; available via Accelrys on http://www.accelrys.com), and alignments can be done using, for example, the ClustalW algorithm (VNTI software, InforMax Inc.). A sequence database can be searched using the peptide sequence to be compared. Algorithms for database searching are typically based on the BLAST software (Altschul et al., 1990).

In one illustrative embodiment, linking a transglutaminase glutamine substrate peptide and a transglutaminase lysine substrate peptide to form an isopeptide bond that results in cyclization of the peptide can be performed using a transglutaminase. In another embodiment, a microbial transglutaminase (e.g., a *Streptoverticillium* sp. transglutaminase) or a mammalian transglutaminase can be used. In the embodiment where the enzyme is a mammalian transglutaminase, the mammalian transglutaminase can be, for example, selected from the group consisting of Human Factor XIII A transglutaminase, Human Factor XIII B transglutaminase, a Factor XIII transglutaminase, a keratinocyte transglutaminase, a tissue-type transglutaminase, an epidermal transglutaminase, a prostate transglutaminase, a neuronal transglutaminase, a human transglutaminase 5, and a human transglutaminase 7.

I. Peptide Tags

Referring to FIG. 24, in some embodiments, a fragmented peptide tag 10 is fragmented across the N- and C-termini of a linear peptide 12 such that, upon cyclization, a full peptide tag 14 is formed. The linear peptide 12 may be formed and cyclized according to the methods described herein. For example, the linear peptide 12 may be attached to a solid support 16 via the side chain of a first amino acid 18 (a C-terminus amino acid), where the remainder of the linear peptide 12 extends outward from the first amino acid to an N-terminus. The linear peptide 12 may be extended according to methods of peptide synthesis known in the art, such as solid-phase peptide synthesis utilizing Fmoc or Boc protecting groups. Although FIG. 24 shows the side chain of the first amino acid 18 (the C-terminus amino acid) attached to the solid support 16, it is contemplated that the side chain of another amino acid of the linear peptide 12 may be connected to the solid support instead of the first amino acid 18.

Still referring to FIG. 24, starting from the solid surface 16, the linear peptide 12 has a first fragment 20 (also referred to herein as a "first end portion") of the peptide tag, a variable region 22, and a second fragment 24 (also referred to herein as a "second end portion") of the protein tag. After cyclization occurs, the first 20 and second fragments 24 of the fragmented peptide tag 10 combine to form a full peptide tag 14 that binds to a target protein binding partner. Binding may be detected, for example, by contacting the full peptide tag 14 with a target protein, subsequently treating the full peptide tag 14 such that unbound target protein is removed, and detecting the remaining target protein that is bound to the full peptide tag 14. Prior to cyclization, the first 20 and second 24 fragments bind more weakly, if at all, to the target protein binding partner relative to binding after cyclization. The linear peptide 12 is designed such that the variable region 22 is flexible enough to allow for cyclization to occur. It is to be understood that the variable region 22 may comprise a sequence of amino acids capable of binding to a target such as a therapeutic target. For example, the variable region 22 may include a peptide sequence of interest as described herein. The peptide sequence of interest may be matured and extended to bind to a target of interest, other than the target protein of the peptide tag, according to the methods described herein.

Figure 7:
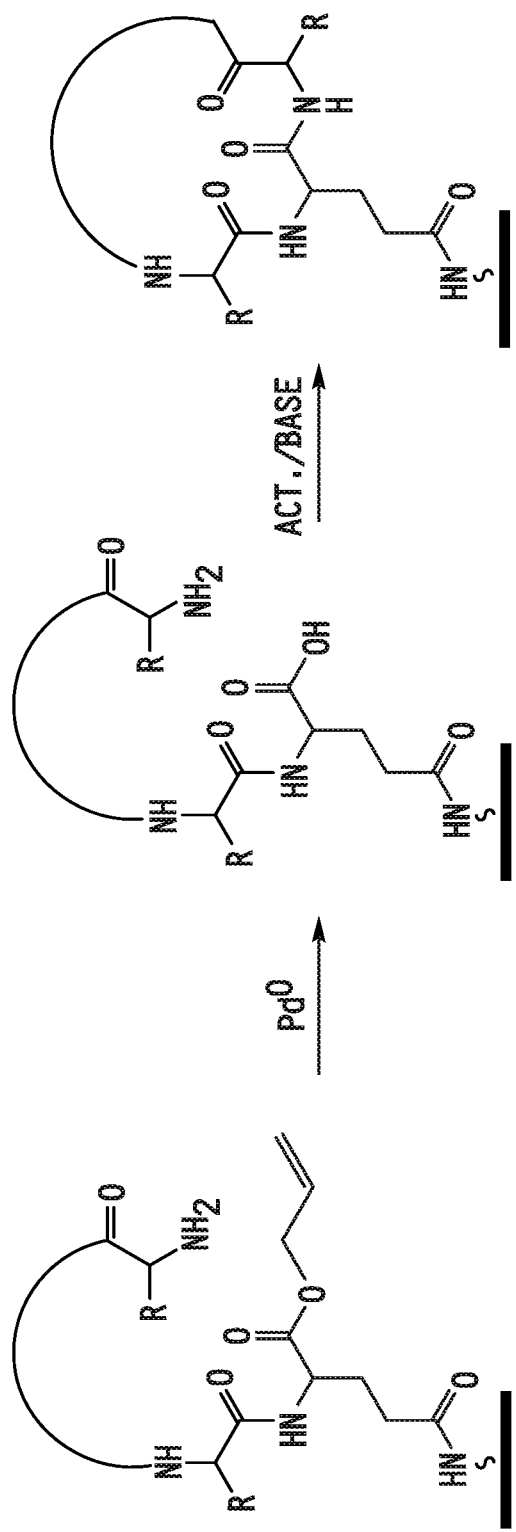
FIG. 7 is a schematic view depicting a reaction scheme for head-to-tail (amide bond formation) cyclization of peptide libraries on a surface.

Still referring to FIG. 24, after formation of the intermediate peptide on the solid support, the peptide is cyclized to form a cyclic peptide. Referring now to FIG. 7, the first amino acid (the C-terminus amino acid) may include a carboxyl-protecting group that is removed as a first step of cyclization. The N-terminus may be unprotected, i.e. a free amino group. After deprotection of the C-terminus, cyclization may be promoted by activating the C-terminus carboxyl group, such as by using an acid or base.

While the peptide tag is not active as a linear peptide, upon cyclization the peptide tag becomes activated. As used herein in reference to the peptide tag, being "activated" refers to experiencing an increase in binding strength to the target protein due to successful cyclization. The full peptide tag of the cyclized peptide can subsequently be detected by binding to its corresponding detectable protein, such as a fluorescently-labelled protein. As such, the detectable protein produces an increased signal when cyclization is successful that can be distinguished from a weaker signal that is detected when cyclization has not occurred such that the extent to which cyclization has taken place can be measured. It is contemplated that the protein tags may be incorporated into the various cyclic peptides described herein.

As used herein, "peptide tag" refers to a polypeptide that binds to a target protein, such as an antibody. In some embodiments, a peptide tag may have, for example fewer than 500 amino acids or fewer than 100 amino acids. The sequence of the peptide tag may be referred to herein as a "binder sequence." The binder sequence results in binding to a target protein that is selective compared to a peptide of the same length having a random sequence. For example, compared to a random peptide having the same length, a peptide tag may have a binding selectivity coefficient to its target protein that is at least about 2, at least about 10, at least about 100, from about 2 to about 1,000,000, from about 10 to about 1,000,000, or from about 100 to about 1,000,000. As used herein, a "binding selectivity coefficient" is the ratio of the two equilibrium constants for respective binding processes. It is to be understood that, after but not before cyclization, the peptide tag binds to its target protein with sufficient binding interaction to remain bound after washing. A peptide tag may be an epitope that is recognized by an antibody. A FLAG-tag that binds to an anti-FLAG antibody is an example of a peptide tag. Exemplary peptide tags include, but are not limited to peptide tags selected from the group consisting of AviTag (GLNDIFEAQKIEWHE (SEQ ID NO: 238)), Calmodulin-tag (KRRWKKNFIA-VSAANRFKKISSSGAL (SEQ ID NO: 239)), polyglutamate tag (EEEEEE (SEQ ID NO: 240)), E-tag (GAPVPYPDPLEPR (SEQ ID NO: 241)), FLAG-tag (DYKDDDDK (SEQ ID NO: 242)), HA-tag (YPYDVPDYA (SEQ ID NO: 243)), His-tag (i.e. HHHHHH (SEQ ID NO: 244)), Myc-tag (EQKLISEEDL (SEQ ID NO: 245)), S-tag (KETAAAKFERQHMDS (SEQ ID NO: 246)), SBP-tag (MDEKTTGWRGGHVVEG-LAGELEQLRARLEHHPQGQREP (SEQ ID NO: 247)), Softag 1 (SLAELLNAGLGGS (SEQ ID NO: 248)), Softag 3 (TQDPSRVG (SEQ ID NO: 249)), Strep-tag (i.e. WSHPQFEK (SEQ ID NO: 250)) TC tag (CCPGCC (SEQ ID NO: 251)), V5 tag (GKPIPNPLLGLDST (SEQ ID NO: 252)), VSV-tag (YTDIEMNRLGK (SEQ ID NO: 253)), and Xpress tag (DLYDDDDK (SEQ ID NO: 254)). It is further contemplated that any of these peptide tags may be modified based on the methods described herein.

As used herein, a "target protein" is a protein to which a peptide tag binds.

As used herein, "detectable protein" is a protein that can be detected according to analytical protein detection methods. For example, the presence of a detectable protein, relative to its absence, can be detected by spectroscopic methods such as fluorescence spectroscopy, UV spectroscopy, or visible spectroscopy. It is to be understood that detectable proteins include proteins having detectable labels attached thereto.

Although detectable target proteins are described in various embodiments, it is to be understood that in alternative embodiments other detectable targets may be used, such as detectable small molecules, so long as a peptide tag binds to such targets as described herein.

As used herein, "does not substantially interfere" refers to not preventing components of the subject disclosure from functioning as described herein in a manner consisting with the uses described herein.

In some embodiments, a method is provided for selecting an oligopeptide tag sequence that can be used as a protein tag in a cyclic peptide. The methodology can be applied to design new peptide tags or to further optimize existing peptides tags suitable for detection of peptide cyclization. A peptide of 3 to 100, 4 to 100, 5 to 100, 7 to 100, 3 to 50, 4 to 50, 5 to 50, 7 to 50, 3 to 25, 4 to 25, 5 to 25, 7 to 25, 3 to 15, 4 to 15, 5 to 15, or 5 to 20 amino acid residues is selected as a precursor peptide. In some embodiments, these amino acid residues are natural amino acids. In some embodiments, the precursor peptide is any of the peptides described herein, such as a precursor peptide selected from the group consisting of AviTag (GLNDIFEAQKIEWHE (SEQ ID NO: 238)), Calmodulin-tag (KRRWKKNFIA-VSAANRFKKISSSGAL (SEQ ID NO: 239)), polyglutamate tag (EEEEEE (SEQ ID NO: 240)), E-tag (GAPVPYPDPLEPR (SEQ ID NO: 241)), FLAG-tag (DYKDDDDK (SEQ ID NO: 242)), HA-tag (YPYDVPDYA (SEQ ID NO: 243)), His-tag (i.e. HHHHHH (SEQ ID NO: 244)), Myc-tag (EQKLISEEDL (SEQ ID NO: 245)), S-tag (KETAAAKFERQHMDS (SEQ ID NO: 246)), SBP-tag (MDEKTTGWRGGHVVEG-LAGELEQLRARLEHHPQGQREP (SEQ ID NO: 247)), Softag 1 (SLAELLNAGLGGS (SEQ ID NO: 248)), Softag 3 (TQDPSRVG (SEQ ID NO: 249)), Strep-tag (i.e. WSHPQFEK (SEQ ID NO: 250)) TC tag (CCPGCC (SEQ ID NO: 251)), V5 tag (GKPIPNPLLGLDST (SEQ ID NO: 252)), VSV-tag (YTDIEMNRLGK (SEQ ID NO: 253)), Xpress tag (DLYDDDDK (SEQ ID NO: 254)), and sequences having at least 80% identity with any of the foregoing. In the case of precursor peptides having natural amino acid residues, one or more amino acids in the precursor peptide are substituted with other amino acids, such as each of the remaining 19 amino acids, to form modified oligopeptides each having one or more modified residue positions. As used herein, a "modified residue position" is a residue position that has been changed compared to a precursor sequence by substitution, insertion, or deletion. After forming the modified oligopeptides, binding interaction with a detectable target protein is measured for each of the modified oligopeptides. In some embodiments, binding interaction may be measured by analytical techniques including but not limited to fluorescence spectroscopy. It is further contemplated that one or more amino acid positions may be substituted with one or more non-natural amino acids. Based on binding information determined for the modified oligopeptides, favorable amino acid substitutions for increasing binding may be selected for various sequence positions. Additionally, sequence positions are identified where an amino acid may be modified to the other amino acids while still maintaining comparable binding activity. These amino acids are considered to have "low specificity." In some embodiments, in sequence positions having low specificity, the highest binding interaction after substitution at the sequence position compared to the lowest binding interaction after substitution at the sequence positions is less than about 50 times greater, less than about 30 times greater, less than about 20 times greater, less than about 15 times greater, less than about 10 times greater, less than about 5 times greater, or less than about 2 times greater.

After identifying a given substitution that leads to a more desired binding interaction, such as an increased interaction, at a sequence position compared to the precursor peptide, that mutation may be incorporated into a subsequent precursor peptide, and the process may be repeated until the desired specificity at various positions is achieved. In some embodiments, multiple substitutions are identified and each incorporated into a subsequent precursor peptide. A peptide may be designed such that amino acid positions near the C-terminus and N-terminus have a high specificity and lead to an increase in binding activity. These positions may independently be the within 5 sequence positions, 4 sequence positions, 3 sequence positions, 2 sequence positions, or 1 sequence position of each of the C-terminus and the N-terminus. Additionally, a sequence position further from the C-terminus and the N-terminus having low specificity is identified. This position may be more than 5 sequence positions, 4 sequence positions, 3 sequence positions, 2 sequence positions, or 1 sequence position away from of each or the C-terminus and the N-terminus, independently. The oligopeptide may be modified such that at the position having low specificity the residue is substituted an amino acid having a side chain for binding to a microarray. The side chain may be a carboxylic acid side chain such as an aspartate or glutamate side chain, an alcohol side chain such as a serine or tyrosine side chain, or an amine such chain such as a lysine side chain.

It is to be understood that the peptide tags described in this section may be used in the peptides and microarrays described in Sections II-VII.

II. Peptides:

The peptides disclosed and described herein make up a class of molecules having a vast number of applications in the life science and healthcare fields. As disclosed and described herein, the peptides (or "peptide binders" (e.g., cyclic peptides)) described herein may be in a cyclic or constrained (macrocycle) form, or in linear form prior to cyclization.

As used herein, the terms "peptide," "oligopeptide" or "peptide binder" refer to organic compounds composed of amino acids, which may be arranged in either a linear chain (joined together by peptide bonds between the carboxyl and amino groups of adjacent amino acid residues) prior to cyclization, or in a cyclic form or in a constrained (e.g., "macrocycle" form). A macrocycle (or constrained peptide), as used herein, is used in its customary meaning for describing a cyclic small molecule such as a peptide of about 500 Daltons to about 2,000 Daltons.

The term "natural amino acid" refers to one of the 20 amino acids typically found in proteins and used for protein biosynthesis as well as other amino acids which can be incorporated into proteins during translation (including pyrrolysine and selenocysteine). The 20 natural amino acids include histidine, alanine, valine, glycine, leucine, isoleucine, aspartic acid, glutamic acid, serine, glutamine, asparagine, threonine, arginine, proline, phenylalanine, tyrosine, tryptophan, cysteine, methionine and lysine.

The term "non-natural amino acid" refers to an organic compound that is not among those encoded by the standard genetic code, or incorporated into proteins during translation. Therefore, non-natural amino acids include amino acids or analogs of amino acids, but are not limited to, the D-isostereomers of amino acids, the beta-amino-analogs of amino acids, citrulline, homocitrulline, homoarginine, hydroxyproline, homoproline, ornithine, 4-amino-phenylalanine, cyclohexylalanine, α-aminoisobutyric acid, N-methyl-alanine, N-methyl-glycine, norleucine, N-methyl-glutamic acid, tert-butylglycine, α-aminobutyric acid, tert-butylalanine, 2-aminoisobutyric acid, α-aminoisobutyric acid, 2-aminoindane-2-carboxylic acid, selenomethionine, dehydroalanine, lanthionine, γ-amino butyric acid, and derivatives thereof wherein the amine nitrogen has been mono- or di-alkylated.

According to embodiments of the instant disclosure, novel cyclic peptides are described which are immobilized on a solid support (e.g., a microarray). As described in greater detail below, the peptide binders (e.g., cyclic peptides) may enable discovery techniques such as profiling of antibodies, epitope identification, sample profiling, antibody isolation, protein identification as well as diagnostic and therapeutic applications. In some embodiments, the peptide binders can be extended and matured (for example, with natural or non-natural amino acids) prior to cyclization, for example, for preparing a potential drug candidate.

In one aspect of the present disclosure, linear and cyclic peptides in adjacent features or subarrays on the same array are generated without requiring purification. First, peptides are generated on a subarray for forming cyclic peptides. As used herein, the term "subarray" refers to a part or section of a microarray. A microarray may have one or more subarrays. In some embodiments, different molecules on the microarray may be located at different subarrays to facilitate comparison of the molecules. Each of the peptides has a free amino group at its N-terminus and a protected carboxyl group at its C-terminus. In some embodiments, the C-terminus carboxyl group is protected by an allyl or tert-butyl protecting group. As used herein, a "carboxyl group" may be protonated (a carboxylic acid) or deprotonated (a carboxylate). Identical peptides are also generated on a subarray for forming linear peptides, except the carboxyl groups of the peptides on the subarray for forming linear peptides have different protecting groups than the carboxyl groups of the peptides on the cyclic peptide subarray. In some embodiments, the carboxyl group is the C-terminus carboxyl group of the subject peptide, and the amino group is the N-terminus amino group of the subject peptide. During synthesis, the C-terminus and amino acid side chains may be protected.

As used herein, the term "protecting group" refers to any group commonly known in the art that alters the reactivity of a functional group, typically to ameliorate or mask the reactivity of the functional group. Protecting groups useful in connection with the present disclosure include, but are not limited to, carboxyl protecting groups, such as those described in Greene's Protective Groups in Organic Synthesis, Fourth Edition, Copyright © 2007 John Wiley & Sons, Inc., incorporated by reference herein. Exemplary carboxyl protecting groups useful in connection with the present disclosure include, but are not limited to, esters, such as alkyl, allyl, benzyl, phenyl, aryl, and silyl esters; oxazoles; ortho esters; and organometallic complexes, such as cobalt and tin complexes. A non-limiting list of carboxyl protecting groups includes heptyl, 2-N-(morpholino)ethyl, choline, (methoxyethoxy)ethyl, methoxyethyl, methyl, 9-fluorenylmethyl, methoxymethyl, methoxyethoxymethyl, methylthiomethyl, tetrahydropyranyl, tetrahydrofuranyl, 2-(trimethylsilyl)ethoxymethyl, benzyloxymethyl, triisopropylsiloxymethyl, pivaloyloxymethyl, phenylacetoxymethyl, triisopropylsilylmethyl, cyanomethyl, acetol, phenacyl, desyl, carboxamidomethyl, p-azobenzenecarboxamidomethyl, 6-bromo-7-hydroxycoumarin-4-ylmethyl, N-phthalimidomethyl, 2,2,2-trichloroethyl, 2-haloethyl, ω-chloroalkyl, 2-(trimethylsilyl) ethyl, (2-methyl-2-trimethylsilyl) ethyl, (2-phenyl-2-trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, (p-methoxyphenyl)ethyl, 1-methyl-1-phenylethyl, 2-(4-acetyl-2-nitrophenyl)ethyl, 1-[2-(2-hydroxyalkyl)phenyl] ethanone, 2-cyanoethyl, t-butyl, 3-methyl-3-pentyl, dicyclopropylmethyl, 2,4-dimethyl-3-pentyl, cyclopentyl, cyclohexyl, allyl, methallyl, 2-methyl-but-3-en-2-yl, 3-methylbut-2-enyl, 3-buten-1-yl, 4-(trimethylsilyl)-2-buten-1-yl, cinnamyl, α-methylcinnamyl, prop-2-ynyl (propargyl), phenyl, 2,6-dimethylphenyl, 2,6-diisopropylphenyl, 2,6-di-t-butyl-4-methylphenyl, 2,6-di-t-butyl-4-methoxyphenyl, p-(methylthio)phenyl, pentafluorophenyl, 2-(dimethylamino)-5-nitrophenyl, benzyl, triphenylmethyl, 2-chlorophenyldiphenylmethyl, 2,3,4,4',4'',5,6-heptafluorotriphenylmethyl, diphenylmethyl, bis (o-nitrophenyl) methyl, 9-anthrylmethyl, 2-(9, 10-dioxo) anthrylmethyl, 5-dibenzosuberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-Methoxybenzyl, 2,6-dimethoxybenzyl, 4-(methylsulfinyl) benzyl, 4-sulfobenzyl, 4-azidomethoxybenzyl, 4-{N-[1-(4,4-dimethyl-2,6-dioxocyclohexylidene)-3-methylbutyl] amino} benzyl, piperonyl, 4-picolyl, p-polymer-benzyl, 2-naphthylmethyl, 3-nitro-2-naphthylmethyl, 4-quinolylmethyl, 8-bromo-7-hydroxyquinoline-2-ylmethyl, 2-nitro-4,5-dimethoxybenzyl, 1,2,3,4-tetrahydro-1-naphthyl, trimethylsilyl, triethylsilyl, t-butyldimethylsilyl, t-butyldiphenylsilyl, t-propyldimethyl silyl, phenyldimethylsilyl, di-t-butylmethylsilyl, triisopropylsilyl, and tris(2,6-diphenylbenzyl)silyl.

Exemplary amino protecting groups include those described in Greene's Protective Groups in Organic Synthesis, Fourth Edition, Copyright © 2007 John Wiley & Sons, Inc., incorporated by reference herein. Exemplary amino protecting groups useful in connection with the present disclosure include, but are not limited to, carbamates, urea-type derivatives, amides, N-sulfenyl derivatives, and N-sulfonyl derivatives. A non-limiting list of amino protecting groups includes 9-fluorenylmethyl, 2,6-di-t-butyl-9-fluorenylmethyl, 2,7-bis (trimethylsilyl)fluorenylmethyl, 9-(2-sulfo)fluorenylmethyl, 9-(2,7-dibromo)fluorenylmethyl, 17-tetrabenzo [a,c,g,i]fluorenylmethyl, 2-chloro-3-indenylmethyl, benz[f]inden-3-ylmethyl, 1,1-dioxabenzo [b]thiophene-2-ylmethyl, 2-methylsulfonyl-3-phenyl-1-prop-2-enyloxy, 2,7-di-t-butyl-[9-(10,10-dioxo-10,10,10,10-tetrahydrothioxanthyl)] methyl, 2,2,2-trichloroethyl, 2-trimethylsilylethyl, (2-phenyl-2-trimethylsilyl)ethyl, 2-phenylethyl, 2-chloroethyl, 1,1-dimethyl-2-haloethyl, 1,1-dimethyl-2,2-dibromoethyl, 1,1-dimethyl-2,2,2-trichloroethyl, 2-(2'- and 4'-pyridyl)ethyl, 2,2-bis(4'-nitrophenyl) ethyl, 2-[(2-nitrophenyl)dithio]-1-phenylethyl, 2-(N,N-dicyclohexylcarboxamido) ethyl, t-butyl, 1-adamantyl, 2-adamantyl, 1-(1-adamantyl)-1-methylethyl, 1-methyl-1-(4-biphenylyl)ethyl, 1-(3,5-di-t-butylphenyl)-1-methylethyl, triisopropylsiloxyl, vinyl, allyl, prenyl, 1-isopropylallyl, cinnamyl, 4-nitrocinnamyl, 3-(3'-pyridyl)prop-2-enyl, hexadienyloxy, propargyloxy, but-2-ynylbisoxy, 8-quinolyl, N-hydroxypiperidinyl, alkyldithio, benzyl, 3,5-di-t-butylbenzyl, p-methoxybenzyl, p-methoxybenzyl, p-methoxybenzyl, p-chlorobenzyl, 2,4-dichlorobenzyl, 4-methylsulfinylbenzyl, 4-trifluoromethylbenzyl, fluorous benzyl, 2-naphthylmethyl, 9-anthrylmethyl, diphenylmethyl, 4-phenylacetoxybenzyl, 4-azidobenzyl, 4-azidomethoxybenzyl, m-chloro-p-acyloxybenzyl, p-(dihydroxyboryl) benzyl, 5-benzisoxazolylmethyl, 2-(trifluoromethyl)-6-chromonylmethyl, 2-methylthioethyl, 2-methylsulfonylethyl, 2-(p-toluenesulfonyl) ethyl, 2-(4-nitrophenylsulfonyl) ethyl, 2-(2,4-dinitrophenylsulfonyl)ethoxy, 2-(4-trifluoromethylphenyl sulfonyl) ethyl, [2-(1,3-dithianyl)]methyl, 2-phosphonioethyl, 2-[phenyl(methyl)sulfonio]ethyl, 1-methyl-1-(triphenylphosphonio) ethyl, 1,1-dimethyl-2-cyanoethyl, 2-dansylethyl, 2-(4-nitrophenyl)ethyl, 4-methylthiophenyl, 2,4-dimethylthiophenyl, m-nitrophenyl, 3,5-dimethoxybenzyl, 1-methyl-1-(3,5-dimethoxyphenyl)ethyl, α-methylnitropiperonyl, o-nitrobenzyl, 3,4-dimethoxy-6-nitrobenzyl, 3,4-di-substituted-6-nitrobenzyl, phenyl(o-nitrophenyl)methyl, 2-nitrophenylethyl, 6-nitroveratryl, 4-methoxyphenacyl, 3',5'-dimethoxybenzoin, 9-xanthenylmethyl, N-methyl-N-(o-nitrophenyl), N-(2-acetoxyethyl) amine, t-amyl, 1-methylcyclobutyl, 1-methylcyclohexyl, 1-methyl-1-cyclopropylmethyl, cyclobutyl, cyclopentyl, cyclohexyl, isobutyl, isobornyl, cyclopropylmethyl, p-decyloxybenzyl, diisopropylmethyl, 2,2-dimethylcarbonylvinyl, o-(N,N-dimethylcarboxamido)benzyl, 1,1-dimethyl-3-(N,N-dimethylcarboxamido)propyl, butynyl, 1,1-dimethylpropynyl, 2-iodoethyl, 1-methyl-1-(4'-pyridyl)ethyl, 1-methyl-1-(p-phenylazophenyl)ethyl, p-(p'-methoxyphenylazo) benzyl, p-(phenylazo) benzyl, 2,4,6-trimethylbenzyl, isonicotinyl, 4-(trimethylammonium)benzyl, p-cyanobenzyl, di(2-pyridyl)methyl, 2-furanylmethyl, phenyl, 2,4,6-tri-t-butylphenyl, 1-methyl-1-phenylethyl, S-benzyl thiocarbamate, urea, phenothiazinyl-(10)-carbonyl derivative, N'-p-toluenesulfonylaminocarbonyl, N'-phenylaminothiocarbonyl, 4-hydroxyphenylaminocarbonyl, 3-hydroxytryptaminocarbonyl, N'-phenylaminothiocarbonyl, formamide, acetamide, chloroacetamide, trichloroacetamide, trifluoroacetamide, phenylacetamide, 3-phenylpropanamide, pent-4-enamide, picolinamide, 3-pyridylcarboxamide, N-benzoylphenylalanyl derivative, benzamide, p-phenylbenzamide, o-nitrophenylacetamide, 2,2-dimethyl-2-(o-nitrophenyl)acetamide, o-nitrophenoxyacetamide, 3-(o-nitrophenyl)propanamide, 2-methyl-2-(o-nitrophenoxy)propanamide, 3-methyl-3-nitrobutanamide, o-nitrocinnamide, o-nitrobenzamide, 3-(4-t-butyl-2,6-dinitrophenyl)-2,2-dimethylpropanamide, o-(benzoyloxymethyl) benzamide, 2-(acetoxymethyl) benzamide, 2-[(t-butyldiphenylsiloxy)methyl]benzoyl, 3-(3',6'-dioxo-2',4',5-trimethylcyclohexa-1',4'-diene)-3,3-dimethylpropionamide, o-hydroxy-trans-cinnamide, 2-methyl-2-(o-phenylazophenoxy)propanamide, 4-chlorobutanamide, acetoacetamide, 3-(p-hydroxyphenyl)propanamide, (N'-dithiobenzyloxycarbonylamino) acetamide, N-acetylmethionine derivative, 4,5-diphenyl-3-oxazolin-2-one, N-phthalimide, N-dichlorophthalimide, N-tetrachlorophthalimide, N-4-nitrophthalimide, N-thiodiglycoloyl, N-dithiasuccinimide, N-2,3-diphenylmaleimide, N-2,3-dimethylmaleimide, N-2,5-dimethylpyrrole, N-2,5-bis(triisopropylsiloxy)pyrrole, N-1,1,4,4-tetramethyldisilylazacyclopentane adduct, N-1,1,3,3-tetramethyl-1,3-disilaisoindoline, N-diphenylsilyldiethylene group, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, 1,3,5-dioxazine, benzenesulfenamide, 2-nitrobenzenesulfenamide, 2,4-dinitrobenzenesulfenamide, pentachlorobenzenesulfenamide, 2-nitro-4-methoxybenzenesulfenamide, triphenylmethylsulfenamide, 1-(2,2,2-trifluoro-1,1-diphenyl)ethylsulfenamide, N-3-nitro-2-pyridinesulfenamide, methanesulfonamide, trifluoromethanesulfonamide, t-butylsulfonamide, benzylsulfonamide, 2-(trimethylsilyl) ethanesulfonamide, p-toluenesulfonamide, benzenesulfonamide, anisylsulfonamide, 2- or 4-nitrobenzenesulfonamide, 2,4-dinitrobenzenesulfonamide, 2-naphthlenesulfonamide, 4-(4',8'-dimethoxynaphthylmethyl) benzenesulfonamide, 2-(4-methylphenyl)-6-methoxy-4-methylsulfonamide, 9-anthracenesulfonamide, pyridine-2-sulfonamide, benzothiazole-2-sulfonamide, phenacylsulfonamide, 2,3,6-trimethyl-4-methoxybenzenesulfonamide, 2,4,6-trimethoxybenzenesulfonamide, 2,6-dimethyl-4-methoxybenzenesulfonamide, pentamethylbenzenesulfonamide, 2,3,5,6-tetramethyl-4-methoxybenzenesulfonamide, 4-methoxybenzenesulfonamide, 2,4,6-trimethylbenzenesulfonamide, 2,6-dimethoxy-4-methylbenzenesulfonamide, 3-methoxy-4-t-butylbenzenesulfonamide, 2,2,5,7,8-pentamethylchroman-6-sulfonamide.

After generating the microarray, the protected carboxyl groups of the peptides on the subarray for forming cyclic peptides are deprotected. As a result of deprotection, each of peptides on the subarray for forming cyclic peptides now has a free carboxyl group. Although the peptides on the subarray for forming cyclic peptides are deprotected in this step, the carboxyl groups of the peptides on the subarray for forming linear peptides are not removed. As such, peptides on the linear peptide subarray remain protected during this step.

Protecting groups can be removed according to a variety of methods known in the art (a.k.a. deprotection). Exemplary methods for deprotection of (or removal of) carboxyl protecting groups include, but are not limited to, those methods described in Greene's Protective Groups in Organic Synthesis, Fourth Edition, Copyright © 2007 John Wiley & Sons, Inc., incorporated by reference herein. Exemplary methods for the deprotection of carboxyl protecting groups useful in connection with the present disclosure include, but are not limited to hydrolysis, such as hydrolysis of a carboxylic ester by contacting a with a hydroxide base, such as NaOH, KOH, LiOH, CsOH, $Ca(OH)_2$, $Ba(OH)_2$, and the like, nucleophilic displacement of a carboxyl protecting group, such as by contacting with LiS-n-Pr, NaSePh, LiCl, KO-t-Bu, NaCN, NaTeH, $KO_2$, LiI, and PhSH. In some embodiments, and particularly in the case of allyl protecting groups, removing the protecting group may comprising adding a palladium source, such as Pd/C, Pd(0), Pd(II), and the like. One example of Pd(0) is $Pd(PPh_3)_4$. Examples of Pd(II) include $PdCl_2$ and $Pd(OAc)_2$. It is further contemplated that carboxyl protecting groups may be removed by adding an acid, such as trifluoroacetic acid (TFA), hydrochloric acid, p-toluenesulfonic acid, and the like.

Next, peptides on the subarray for forming cyclic peptides are exposed to conditions to promote the formation of amide bonds between their free amino and carboxyl groups. Due to this amide bond formation, the peptides on the subarray for forming cyclic peptides are cyclized to form cyclic peptides. During the cyclization step, some inefficiency is to be expected, and not all of the peptides cyclize. Peptides that do not cyclize remain in a deprotected linear form. Because the peptides on the subarray for forming linear peptides have protected carboxyl groups, amide bond formation does not occur during this step for these peptides, which remain in a protected linear form.

In some embodiments, linear peptides described herein are cyclized to form cyclic peptides by forming an amide bond between the C-terminus carboxyl group and the N-terminus amino group of linear peptides. Such reactions can be promoted by amide bond forming conditions commonly known in the art, including, but not limited to, conditions for activation of the C-terminus carboxyl group. Exemplary amide bond forming conditions useful in connection with the present disclosure include, but are not limited to, carbodiimides, such as dicyclohexylcarbodiimide, diisopropylcarbodiimide, and (N-(3-dimethylaminopropyl)-N'-ethylcarbodiimide.HCl; additives, such as 1-hydroxybenzotriazole, hydroxy-3,4-dihydro-4-oxo-1,2,3-benzotriazine, 2-(1H-benzotriazol-1-yl)-1,1,3,3-tetramethyluronium hexafluorophosphate, N-hydroxysuccinimide, 1-hydroxy-7-aza-1H-benzotriazole, ethyl 2-cyano-2-(hydroximino)acetate, and 4-(N,N-dimethylamino)pyridine; phosphonium reagents, such as benzotriazol-1-yloxy-tris (dimethylamino)-phosphonium hexafluorophosphate, benzotriazol-1-yloxy-tripyrrolidino-phosphonium hexafluorophosphate, bromo-tripyrrolidino-phosphonium hexafluorophosphate, 7-aza-benzotriazol-1-yloxy-tripyrrolidinophosphonium hexafluorophosphate, ethyl cyano(hydroxyimino)acetato-$O_2$)-tri-(1-pyrrolidinyl)-phosphonium hexafluorophosphate, and 3-(diethoxy-phosphoryloxy)-1,2,3-benzo[d]triazin-4(3H)-one; aminium/uronium-imonium reagents, such as 2-(1H-benzotriazol-1-yl)-N,N,N',N'-tetramethylaminium tetrafluoroborate/hexafluorophosphate, 2-(6-chloro-1H-benzotriazol-1-yl)-N,N,N',N'-tetramethylaminium hexafluorophosphate, (N-[(5-chloro-1H-benzotriazol-1-yl)-dimethylamino-morpholino]-uronium hexafluorophosphate N-oxide, 2-(7-aza-1H-benzotriazol-1-yl)-N,N,N',N'-tetramethylaminium hexafluorophosphate, (1-[1-(cyano-2-ethoxy-2-oxoethylideneaminooxy)-dimethylamino-morpholino]-uronium hexafluorophosphate, (2-(1-oxy-pyridin-2-yl)-1,1,3,3-tetramethylisothiouronium tetrafluoroborate, and tetramethylfluoroformamidinium hexafluorophosphate; and other coupling reagents, such as N-ethoxycarbonyl-2-ethoxy-1,2-dihydroquinoline, 2-Propanephosphonic acid anhydride, 4-(4,6-dimethoxy-1,3,5-triazin-2-yl)-4-methylmorpholinium salts, triphosgene, and 1,1'-carbonyldiimidazole.

After the cyclization step, the peptides on the subarray for forming linear peptides are deprotected. As a result of this deprotection step, peptides on the subarray for forming linear peptides are structurally identical to peptides on the subarray for forming cyclic peptides that fail to cyclize during the cyclization step. The binding properties of peptides on the linear peptide subarray and peptides on the cyclic peptide subarray can be compared to determine cyclic versus linear binding preferences against a given target. In doing so, it is possible to determine whether the linear sequence is contributing to binding in the cyclic feature. Several pairs of linear and cyclic peptide subarrays can be formed on a microarray to identify peptide sequences of interest.

Referring to FIGS. 9A and 9B, in some embodiments, a linear peptide library is synthesized on the microarray by attaching the subject peptides to the microarray through the side chain of a linker amino acid. Although glutamate is shown in FIGS. 9A and 9B, other amino acid side chains, such as an aspartate side chain, may couple to the microarray surface active group to attach the subject peptides. Other amino acid side chains, natural or unnatural, such as alcohol, amine, thiol, acyl, phosphonyl, sulfonyl, and other functional groups that can form a covalent bond with the active group on the microarray surface are contemplated herein. It is further contemplated that the C-terminus carboxyl group of the linker amino acid may be coupled to the reactive surface, and the side chain of the linker amino may be a carboxyl side chain groups capable of forming an amide bond an amino group. The carboxyl protecting groups can be any two different carboxyl protecting groups that allow for selective deprotection and cyclization of one set of peptides without allowing the second set of peptides to cyclize.

III. Microarrays:

In one embodiment, peptide microarrays are described which may be used in research and healthcare. For example, the peptide microarrays described herein may be utilized in the identification of biologically active motifs (e.g., the peptides on the microarrays (e.g., cyclic peptides) may imitate potential active motifs of ligands for screening the binding to corresponding receptors). In one aspect, the peptide microarrays disclosed herein may reflect specific sequences of disease-associated antigens (and thus be utilized for diagnostic or monitoring purposes, e.g., to detect antibodies from patient samples suggesting the presence of certain diseases). Another application of the peptide microarrays is the discovery of biochemical interactions, including the binding of proteins or DNA to peptides (e.g., cyclic peptides) immobilized on the peptide microarray, or for profiling cellular activity, enzymatic activity, cell adhesion, and the like.

Various methods for the production of peptide microarrays are known in the art. For example, spotting prefabricated peptides or in-situ synthesis by spotting reagents, e.g., on membranes, exemplify known methods. Other known methods used for generating peptide microarrays of higher density are the so-called photolithographic techniques, where the synthetic design of the desired biopolymers is controlled by suitable photolabile protecting groups (PLPG) releasing the linkage site for the respective next component (amino acid) upon exposure to electromagnetic radiation, such as light (Fodor et al., (1993) Nature 364:555-556; Fodor et al., (1991) Science 251:767-773). Two different photolithographic techniques are known in the state of the art. The first is a photolithographic mask, used to direct light to specific areas of the synthesis surface effecting localized deprotection of the PLPG (see, for example, FIG. 1). "Masked" methods include the synthesis of polymers utilizing a mount (e.g., a "mask") which engages a substrate and provides a reactor space between the substrate and the mount. Exemplary embodiments of such "masked" array synthesis are described in, for example, U.S. Pat. Nos. 5,143,854 and 5,445,934, the disclosures of which are hereby incorporated by reference. Potential drawbacks of this technique, however, include the need for a large number of masking steps resulting in a relatively low overall yield and high costs, e.g., the synthesis of a peptide of only six amino acids in length could require over 100 masks.

The second photolithographic technique is the so-called maskless photolithography, where light is directed to specific areas of the synthesis surface effecting localized deprotection of the PLPG by digital projection technologies, such as micromirror devices (Singh-Gasson et al., Nature Biotechn. 17 (1999) 974-978). Such "maskless" microarray synthesis thus eliminates the need for time-consuming and expensive production of exposure masks. It should be understood that the embodiments of the peptide microarrays, methods of generating peptide microarrays, and methods of identifying peptide binders (e.g., cyclic peptides) using microarrays disclosed herein may utilize any of the various peptide microarray synthesis techniques described above.

The use of PLPG (photolabile protecting groups), providing the basis for the photolithography based synthesis of peptide microarrays, is well known in the art. Commonly used PLPG for photolithography based biopolymer synthesis are for example α-methyl-6-nitropiperonyl-oxycarbonyl (MeNPOC) (Pease et al., Proc. Natl. Acad. Sci. USA (1994) 91:5022-5026), 2-(2-nitrophenyl)-propoxycarbonyl (NPPOC) (Hasan et al. (1997) Tetrahedron 53: 4247-4264), nitroveratryloxycarbonyl (NVOC) (Fodor et al. (1991) Science 251:767-773) and 2-nitrobenzyloxycarbonyl (NBOC) (Patchornik et al. (1970) 21:6333-6335).

Amino acids have been introduced in photolithographic solid-phase peptide synthesis of peptide microarrays, which were protected with NPPOC as a photolabile amino protecting group, wherein glass slides were used as a solid support (U.S. App. Pub. No. 2005/0101763 A1). The method using NPPOC protected amino acids has the disadvantage that the half-life upon irradiation with light of all (except one) protected amino acids is within the range of approximately 2 to 3 minutes under certain conditions. In contrast, under the same conditions, NPPOC-protected tyrosine exhibits a half-life of almost 10 minutes. As the velocity of the whole synthesis process depends on the slowest sub-process, this phenomenon increases the time of the synthesis process by a factor of 3 to 4. Concomitantly, the degree of damage by photogenerated radical ions to the growing peptides increases with increasing and excessive light dose requirement.

As used herein, the term "peptide microarray" refers to a two dimensional arrangement of features on the surface of a solid support. A single peptide microarray or, in some cases, multiple peptide microarrays (e.g., 3, 4, 5, or more peptide microarrays) can be located on one solid support. The size of the peptide microarrays depends on the number of peptide microarrays on one solid support. The higher the number of peptide microarrays per solid support, the smaller the peptide microarrays have to be to fit on the solid support. The arrays can be designed in any shape, but preferably they are designed as squares or rectangle. The ready to use product is the peptide microarray on the solid support (e.g., peptide microarray slide).

The term "peptide microarray" (or peptide chip or peptide epitope microarray) includes a population or collection of peptides displayed on a solid support, for example a glass, carbon composite or plastic array, slide or chip. Exemplary uses of peptide microarrays include the fields of biology, medicine and pharmacology, including the study of binding properties, functionality and kinetics of protein-protein interactions. Basic research use may include profiling of enzymes (e.g., kinase, phosphatase, protease, acetyltransferase, histone deacetylase) and mapping an antibody epitope to find key residues for protein binding. Other applications include seromarker discovery, profiling of changing humoral immune responses of individual patients during disease progression, monitoring of therapeutic interventions, patient stratification and development of diagnostic and therapeutic tools and vaccines.

The term "feature" refers to a defined area on the surface of a peptide microarray. The feature comprises biomolecules, such as peptides. One feature can contain biomolecules with different properties, such as different sequences or orientations, as compared to other features. The size of a feature is determined by two factors: i) the number of features on a peptide microarray, the higher the number of features on a peptide microarray, the smaller is each single feature, and ii) the number of individually addressable aluminum mirror elements which are used for the irradiation of one feature. The higher the number of mirror elements used for the irradiation of one feature, the bigger is each single feature. The number of features on a peptide microarray may be limited by the number of mirror elements (pixels) present in the micro mirror device. For example, a micro mirror device from Texas Instruments, Inc. currently contains about 12 million mirror elements (pixels), thus the number of features within such exemplary peptide microarray is therefore limited by this number. However, it should be understood that the micro mirror device from Texas Instruments, Inc. is provided only for exemplary purposes and higher density peptide microarrays are possible.

The term "solid support" refers to any solid material, having a surface area to which organic molecules can be attached through bond formation or absorbed through electronic or static interactions such as covalent bond or complex formation through a specific functional group. The solid support can be a combination of materials such as plastic on glass, carbon on glass, and the like. The functional surface can be simple organic molecules but can also comprise co-polymers, dendrimers, molecular brushes and the like.

The term "plastic" refers to synthetic materials, such as homo- or hetero-co-polymers of organic building blocks (monomer) with a functionalized surface such that organic molecules can be attached through covalent bond formation or absorbed through electronic or static interactions such as through bond formation through a functional group. Preferably the term "plastic" refers to polyolefin, which is a polymer derived by polymerization of an olefin (e.g., ethylene propylene diene monomer polymer, polyisobutylene).

Most preferably, the plastic is a polyolefin with defined optical properties, like TOPAS® or ZEONOR/EX®.

The term "functional group" refers to any of numerous combinations of atoms that form parts of chemical molecules, that undergo characteristic reactions themselves, and that influence the reactivity of the remainder of the molecule. Typical functional groups include, but are not limited to, hydroxyl, carboxyl, aldehyde, carbonyl, amino, azide, alkynyl, thiol and nitril. Potentially reactive functional groups include, for example, amines, carboxylic acids, alcohols, double bonds, and the like. Preferred functional groups are potentially reactive functional groups of amino acids such as amino groups or carboxyl groups. Functionalized peptides contain reactive functional groups.

As used herein, "substantially does not cyclize" means that less than 5% cyclize.

As understood by one of skill in the art, peptide microarrays comprise an assay principle whereby thousands (or in the case of the instant disclosure, millions) of peptides (in some embodiments presented in multiple copies) are linked or immobilized to the surface of a solid support (which in some embodiments comprises a glass, carbon composite or plastic chip or slide). According to embodiments of the instant disclosure, peptide microarrays may be incubated with a variety of different targets of interest including purified enzymes or antibodies, patient or animal sera, cell lysates, ligands for receptors, receptors, substrates for enzymes, and the like.

In some embodiments, the peptide microarray, after incubation with a target of interest, undergoes one or more washing steps, and then is exposed to a secondary antibody having a desired specificity (e.g. anti IgG human/mouse or anti phosphotyrosine or anti myc). Usually, the secondary antibody is tagged by a fluorescent label that can be detected by a fluorescence scanner. Other detection methods are chemiluminescence, colorimetry or autoradiography.

In some embodiments, after scanning the peptide microarray slides, the scanner records a 20-bit, 16-bit or 8-bit numeric image in tagged image file format (*.tif). The .tif-image enables interpretation and quantification of each fluorescent spot on the scanned peptide microarray slide. This quantitative data is the basis for performing statistical analysis on measured binding events or peptide modifications on the peptide microarray slide. For evaluation and interpretation of detected signals an allocation of the peptide spot (visible in the image) and the corresponding peptide sequence has to be performed.

In one embodiment, a peptide microarray can be a slide with peptides spotted onto it or assembled directly on the surface by in-situ synthesis. Peptides are ideally covalently linked through a chemoselective bond leading to peptides with the same orientation for interaction profiling. Alternative procedures include unspecific covalent binding and adhesive immobilization.

Figure 1:
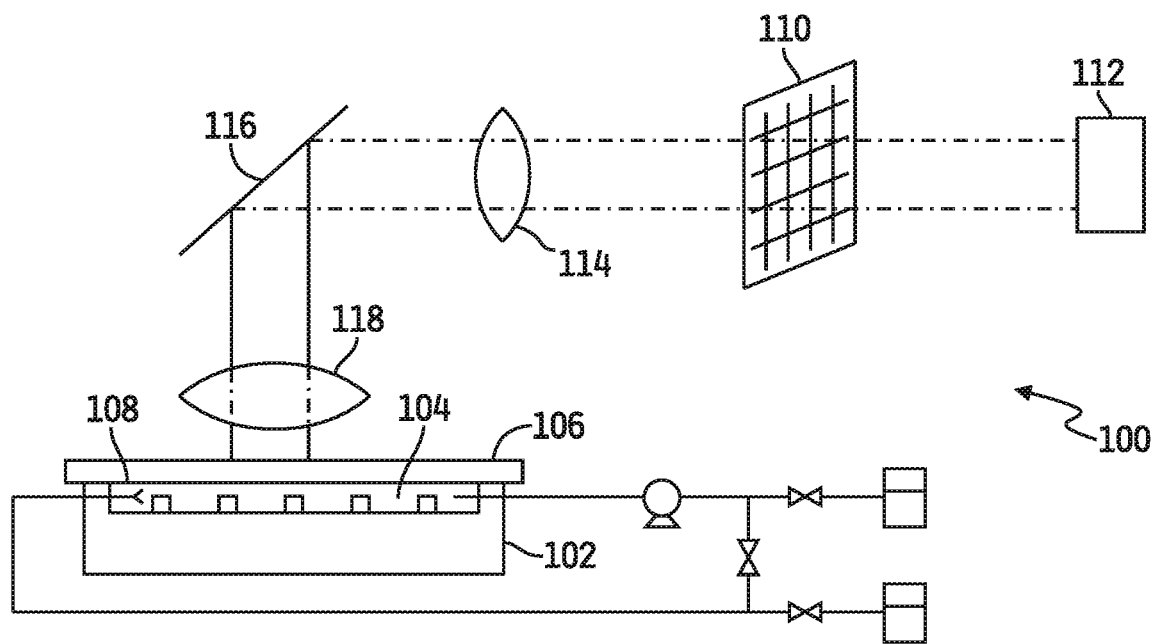
FIG. 1 is a schematic view of a microarray system for array synthesis by way of a photolithographic technique utilizing photolithographic mask (Prior art).
Figure 2:
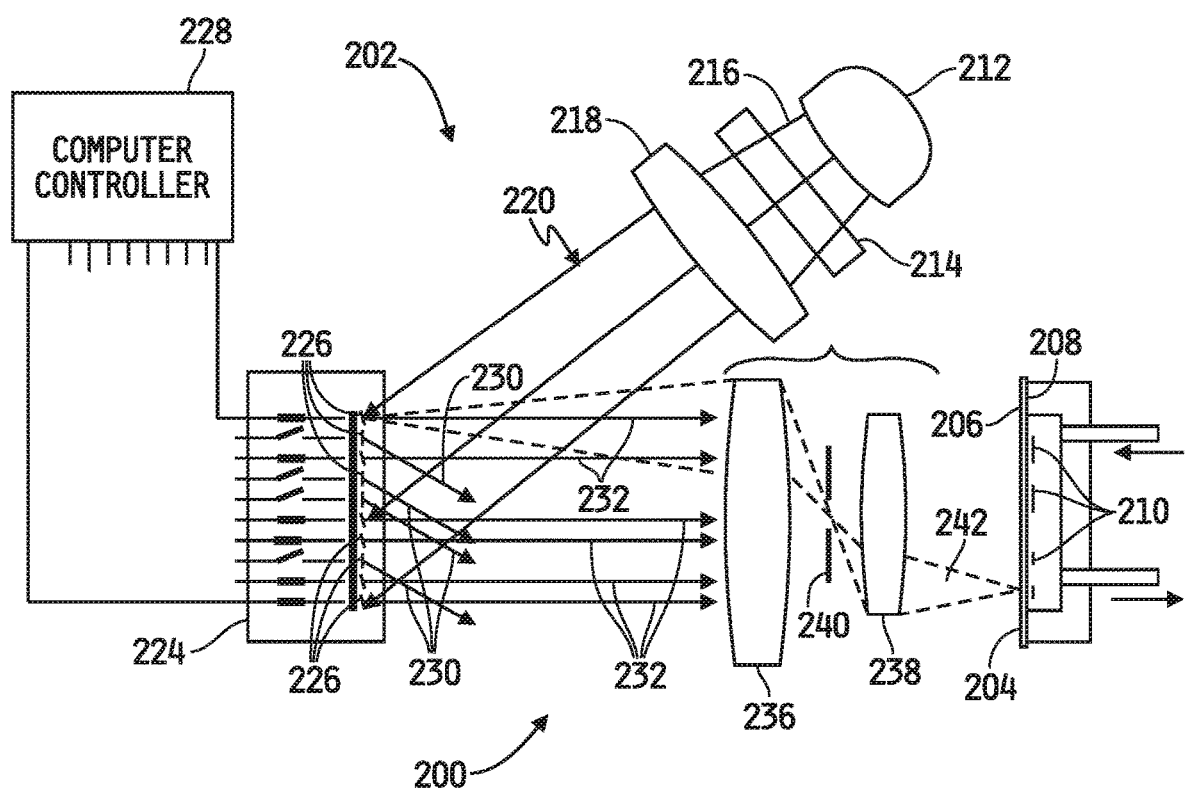
FIG. 2 is a schematic view of a microarray system for array synthesis by way of a photolithographic technique utilizing maskless photolithography (Prior art).

With reference to FIGS. 1 and 2, embodiments of various peptide microarray synthesizers (utilized in both masked and maskless photolithographic techniques, respectively) are presented. Specifically referring now to FIG. 1, an exemplary system 100 for performing masked photolithographic techniques (such as taught in U.S. Pat. No. 5,445,934) is shown, illustrating a system body 102 with a cavity 104 defined at a surface thereof. A substrate (solid support) 106, having a photoremovable protective group (for example, such as NVOC with or without an intervening linker molecule) along its bottom surface 108 is mounted above the cavity 104. The substrate (solid support) 106, for example, may be transparent to a wide spectrum of light, or in some embodiments is transparent only at a wavelength at which the protective group may be removed (such as UV in the case of NVOC). The substrate (solid support) 106 and the body 102 seal the cavity 104 (except for inlet and outlet ports) and may be mated, for example, by way of gasket(s) or a vacuum.

Lens 118, and in some embodiments, reflective mirror 116 are provided for focusing and directing light from light source 112 (such as a Xe(Hg) light source) onto substrate (solid support) 106. In the illustrated embodiment of FIG. 1 a second lens 114 is shown (and in some embodiments may be provided) for projecting a mask image onto the substrate (solid support) in combination with lens 118 (a.k.a., "projection printing"). Light (from light source 112), prior to contacting substrate (solid support) 106 contacts mask 110, whereby such light is permitted to reach only selected locations on substrate (solid support) 106. Mask 110 may be, for example, a glass slide having etched chrome thereon. In some embodiments, mask 110 may be provided with a grid of transparent locations and opaque locations, for example. As is understood by a person of skill in the art, with masked array synthesis, light passes freely through "transparent" regions of mask 110, but is reflected from, or absorbed by, other (e.g., "non-transparent") regions of mask 110. Thus, only selected regions of substrate (solid support) 106 are exposed to light.

Also, light valves (LCD's) may be used as an alternative to conventional masks (to selectively expose regions of the substrate); fiberoptic faceplates may be used (for contrast enhancement of the mask or as the sole means of restricting the region to which light is applied); and fly's-eye lenses, tapered fiberoptic faceplates, or the like, may also be used for contrast enhancement. Also, it should be understood that illumination of regions smaller than a wavelength of light may be accomplished with more elaborate techniques as known in the art (e.g., directing light at the substrate by way of molecular microcrystals on the tip of, for example, micropipettes). Exemplary devices are disclosed in Lieberman et al., "A Light Source Smaller than the Optical Wavelength," Science (1990) 247:59-61.

Now, specifically referring to FIG. 2, an exemplary "maskless" peptide microarray system (as described, for example, in U.S. Pat. No. 6,375,903) that may be utilized in accordance with the instant disclosure is provided for illustrating "maskless" peptide microarray synthesis. The illustrative system, shown generally as 200, is depicted including a two-dimensional array image former 202 and a substrate (solid support) 204 onto which the array image is projected. In the illustrative embodiment presented at FIG. 2, the substrate (solid support) has an exposed entrance surface 206 and an opposite active surface 208 on which a two-dimensional array of peptides 210 is to be fabricated. However, in some embodiments the substrate (solid support) 204 may have active surface 208 facing the image former 202 and enclosed within a reaction chamber flow cell having a transparent window (allowing light to be projected onto the active surface 208). (solid support) Embodiments may include opaque or porous substrates (solid support) 204 as well.

In some embodiments of maskless peptide microarrays according to this instant disclosure, an image former 202 may include a light source 212 (e.g., an ultraviolet or near ultraviolet source such as a mercury arc lamp), an optional filter 214 (to receive output beam 216 from source 212 and selectively pass only the desired wavelengths, e.g., 365 nm Hg line), and a condenser lens 218 (for forming a collimated beam 220). Other devices for filtering or monochromating the source light, e.g., diffraction gratings, dichroic mirrors, and prisms, may also be used rather than a transmission filter, and are generically referred to as "filters" herein.

As shown, beam 220 is projected a two-dimensional micromirror array device 224 having a two-dimensional array of individual micromirrors 226 which are each responsive to control signals (provided by computer controller 228) supplied to the array device 224 to tilt in one of at least two directions. In some embodiments, the micromirrors 226 are constructed so that: A.) in a first position beam 220 that strikes an individual micromirror 226 may be deflected in a direction oblique to beam 220 (as indicated by the arrows 230); and B.) in a second position, beam 220 striking such mirrors is reflected back parallel to beam 220, as indicated by the arrows 232. As should be understood, the light reflected from each of the mirrors 226 constitutes an individual beam 232. The beams 232 are incident upon projection optics 234 (comprising, for example, lenses 236, 238 and an adjustable iris 240). The projection optics 234 serve to form an image of the pattern of the micromirror array 224, as represented by the individual beams 232 (and the dark areas between these beams), on the active surface 208 of the substrate 204. As described above and throughout this disclosure, the substrate support 204 may be transparent, and may be, for example, formed of fused silica or soda lime glass or quartz, so that the light projected thereon (illustrated by the lines 242), passes through substrate 204 without substantial attenuation or diffusion.

An exemplary micromirror array 224 in accordance with the instant disclosure includes the Digital Micromirror Device (DMD) (available commercially from Texas Instruments, Inc.) which is capable of forming patterned beams of light by electronically addressing the micromirrors in the arrays. Such arrays are discussed, for example, in: Larry J. Hornbeck, "Digital Light Processing and MEMs: Reflecting the Digital Display Needs of the Networked Society," SPIE/EOS European Symposium on Lasers, Optics, and Vision for Productivity and Manufacturing I, Besancon, France, Jun. 10-14, 1996; and U.S. Pat. Nos. 5,096,279, 5,535,047, 5,583,688, 5,600,383 and 6.375,903. The micromirrors 226 of such devices are capable of reflecting the light of normal usable wavelengths, including ultraviolet and near ultraviolet light, in an efficient manner without damage to the mirrors themselves.

In some peptide microarray embodiments, the projection optics 234 may be of standard design. Lenses 236, 238 focus the light in beam 232 (passed through adjustable iris 240) onto the active surface 208 of substrate 204. The iris 240 aides in controlling the effective numerical aperture and in ensuring that unwanted light (particularly the off-axis beams 230) is not transmitted to substrate (solid support) 204. Resolutions of dimensions as small as a fraction of a micron are obtainable with such optics systems. Various alternate configurations (e.g., for example as preferred in manufacturing applications), as known in the art may also be utilized in accordance with the instant application.

It should be understood that although exemplary embodiments are provided herein, various approaches may be utilized in the fabrication of the peptides 210 on the substrate (solid support) 204, and include adaptations of microlithographic techniques. For example, in a "direct photofabrication approach," the substrate (solid support) 204 may be coated with a layer of a chemical capable of binding amino acids (e.g., an amine) which, for example, may be protected with a chemical group that is able to react with and be removed by light. Light therefore may be applied by the projection system 202, deprotecting the amine groups on the substrate 204 and making them available for binding the amino acids (which are flowed onto the active surface 208 of the substrate (solid support) 204 for binding to the selected sites using normal chemistry). This process is repeated multiple times, thereby binding another amino acid to a different set of locations. The process is simple, and if a combinatorial approach is used the number of permutations increases exponentially.

According to some embodiments of the instant disclosure, maskless array synthesis is utilized in the fabrication of the peptides 210 on substrate (solid support) 204. According to such embodiments, the maskless array synthesis employed allows ultra-high density peptide synthesis with synthesis up to 2.9M unique peptides. Each of 2.9M synthesis features/regions have up to $10^7$ reactive sites that could yield a full length peptide. Smaller peptide microarrays can also be designed. For example, a peptide microarray representing a comprehensive list of all possible 5-mer peptides using all natural amino acids excluding cysteine will have 2,476,099 peptides. A peptide microarray of 5-mer peptides by using all combinations of 18 natural amino acids excluding cysteine and methionine may also be used. Additionally, a peptide microarray can exclude other amino acids or aminoacid dimers. For example, the 18-mer array exemplified above may be designed to exclude any dimer or a longer repeat of the same amino acid, as well as any peptide containing HR, RH, HK, KH, RK, KR, HP, and PQ sequences to create a library of 1,360,732 unique peptides. Smaller peptide microarrays may have replicates of each peptide on the same peptide microarray to increase the confidence of the conclusions drawn from peptide microarray data.

In various embodiments, the peptide microarrays described herein can have at least $1.6\times10^5$ peptides, at least $2.0\times10^5$ peptides, at least $3.0\times10^5$ peptides, at least $4.0\times10^5$ peptides, at least $5.0\times10^5$ peptides, at least $6.0\times10^5$ peptides, at least $7.0\times10^5$ peptides, at least $8.0\times10^5$ peptides, at least $9.0\times10^5$ peptides, at least $1.0\times10^6$ peptides, at least $1.2\times10^6$ peptides, at least $1.4\times10^6$ peptides, at least $1.6\times10^6$ peptides, at least $1.8\times10^6$ peptides, at least $1.0\times10^7$ peptides, or at least $1.0\times10^8$ peptides attached to the solid support of the peptide microarray. In other embodiments, the peptide microarrays described herein can have about $1.6\times10^5$ peptides, about $2.0\times10^5$ peptides, about $3.0\times10^5$ peptides, about $4.0\times10^5$ peptides, about $5.0\times10^5$ peptides, about $6.0\times10^5$ peptides, about $7.0\times10^5$ peptides, about $8.0\times10^5$ peptides, about $9.0\times10^5$ peptides, about $1.0\times10^6$ peptides, about $1.2\times10^6$ peptides, about $1.4\times10^6$ peptides, about $1.6\times10^6$ peptides, about $1.8\times10^6$ peptides, about $1.0\times10^7$ peptides, or about $1.0\times10^8$ peptides attached to the solid support of the peptide microarray. As described herein, a peptide microarray comprising a particular number of peptides can mean a single peptide microarray on a single solid support, or the peptides can be divided and attached to more than one solid support to obtain the number of peptides described herein.

Peptide microarrays synthesized in accordance with such embodiments can be designed for peptide binder discovery in the cyclic form (as noted herein) and with and without modification such as N-methyl or other PTMs. Peptide microarrays cam also be designed for further extension of potential binders using a block-approach by performing iterative screens on the N-terminus and C-terminus of a potential hit (as is further described in detail herein). Once a hit of an ideal interaction has been discovered it can be further matured using a combination of maturation arrays (described further herein), that allow a combinatorial insertion, deletion and replacement analysis of various amino acids, both natural and non-natural. In one embodiment, the maturation and/or extension process can be followed by cyclization.

The peptide microarrays of the instant disclosure can be used in monoclonal antibody cross reactivity profiling, polyclonal sera profiling, epitope identification (for an antibody of interest), lupus immune reactivity profiling, gut profiling; cancer biomarker profiling, pseudo-monoclonal antibody isolation (from isolates of a polyclonal antibody), peptide to protein interaction characterization, affinity purification, and specific and sensitive binding analysis for diagnostic or therapeutic applications. In one embodiment, peptide binders identified and disclosed herein can be matured and/or extended (including with non-natural amino acids) and a cyclic peptide formed making such binder a potential drug candidate.

Figure 3:
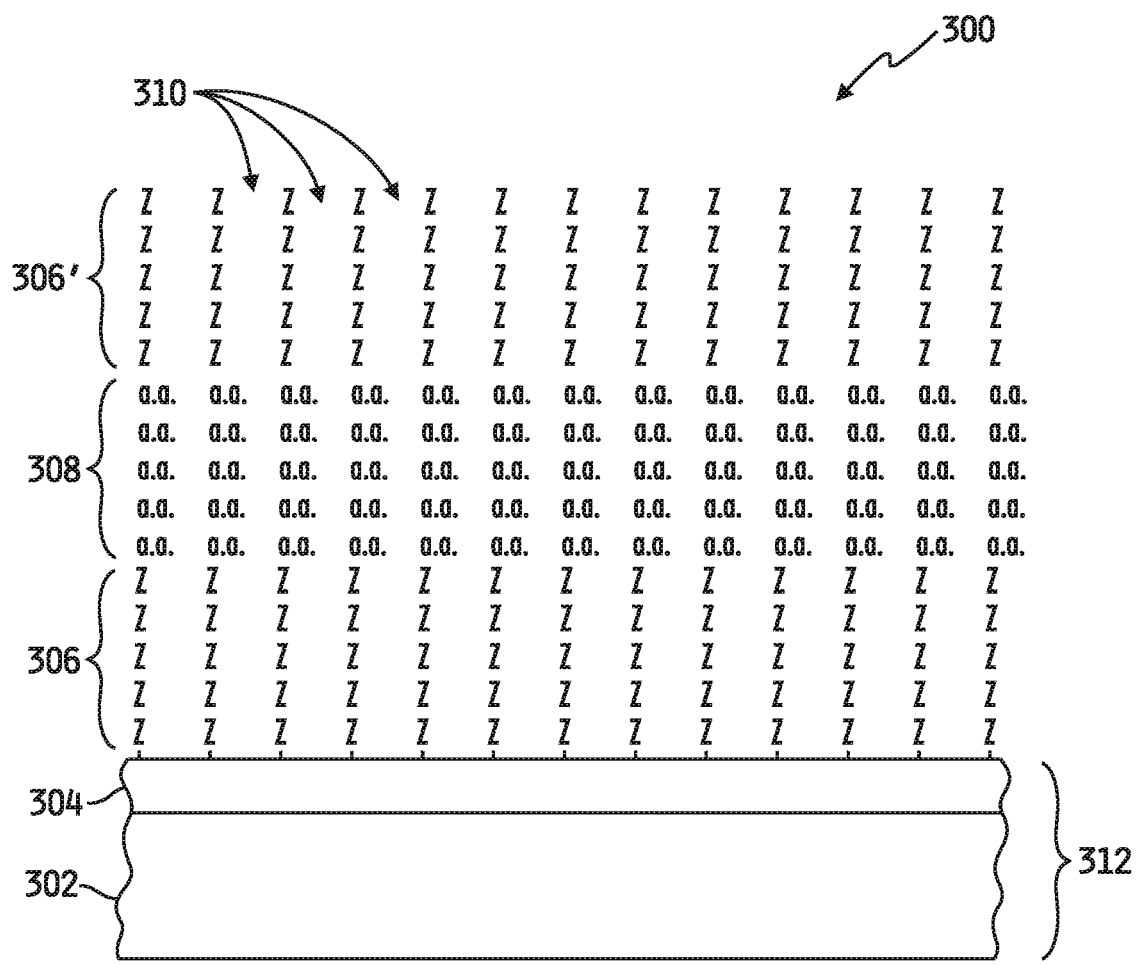
FIG. 3 is a schematic view illustrating arrays comprising peptide probes thereon in accordance with the present disclosure.

IV. Peptide Binder Discovery:

Discovery of novel peptide binders (e.g., cyclic peptides; see, for example, FIG. 4, the method generally represented as 400) may be accomplished, according to the instant disclosure. As explained herein, such novel peptide binders can be utilized in numerous applications, including but not limited to therapeutics, diagnostic applications and general laboratory applications. According to some specific embodiments of the instant disclosure, a peptide microarray may be designed comprising a population of hundreds, thousands, tens of thousands, hundreds of thousands and even millions of peptides. With reference to FIG. 3, in some embodiments, the population of peptides 310 can be configured such that the peptides represent an entire protein, gene, chromosome, molecule or even and entire organism (e.g., a human) of interest. In some embodiments, the peptides can be configured according to specific criteria, whereby specific amino acids or motifs are excluded. In other embodiments, the peptides can be configured such that each peptide comprises an identical length. For example, in some embodiments the population of peptides 310 immobilized on the peptide microarray 312 may all comprise 3-, 4-, 5-, 6-, 7-, 8-, 9-, 10-, 11-, 12-, 13-, 14-, 15-, 16-, 17-, 18-, 19-, or 20-mers 308, or more. In some embodiments, the peptides may also each comprise an N-terminal or a C-terminal sequence (for example, 306 and 306') where each peptide comprises both an N and a C terminal peptide sequence of a specific and identical length (e.g., 3-, 4-, 5-, 6-, 7- or even 8- or more peptides). In some embodiments, the N-terminal or C-terminal sequence (306, 306') is not present, and the peptides 310 immobilized on the peptide microarray 312 only comprise the 3-, 4-, 5-, 6-, 7-, 8-, 9-, 10-, 11-, 12-, 13-, 14-, 15-, 16-, 17-, 18-, 19-, or 20-mers 308. In some embodiments, the peptides 310 immobilized on the peptide microarray 312 comprise cyclic peptides that have been cyclized according to the methods described herein.

According to some embodiments, a peptide microarray 300 is designed including a population of up to 2.9 million peptides 310, configured such that the 2.9 million peptides represents a comprehensive list of all possible 5-mer peptides 308 of a genome, immobilized on a peptide microarray 312. In some such embodiments, the 5-mer peptides 308 (comprising the 2.9 million peptides of the peptide microarray) may exclude the amino acid cysteine (C) (in order to aide in controlling unusual folding of the peptide); or the amino acid methionine (M) (because M is considered a rare amino acid within the proteome); and/or all amino acid repeats of 2 or more of the same amino acid (in order to aide in controlling non-specific interactions such as charge and hydrophobic interactions); or amino acid motifs consisting of histidine (H)-proline (P)-glutamine (Q) sequence. In some illustrative embodiments, such as provided at FIG. 3, the 5-mer peptides 308 may exclude one, or more than one of the exclusions listed above. One embodiment of the invention includes a peptide microarray comprising a population of up to 2.9 million 5-mer peptides 310, representing the entire human genome, wherein the 5-mer peptides 308 do not include any of the amino acids C and M, do not include amino acid repeats of 2 or more amino acids and do not include the amino acid motif HPQ. Another embodiment of the invention includes a peptide microarray comprising up to 2.9 million 5-mer peptides, representing the protein content encoded by the entire human genome, wherein the 5-mer peptides do not include any of the amino acids C and M, do not include amino acid repeats of 2 or more amino acids. It should be understood, that the sequences of the peptides at specific locations on the peptide microarray is known. As referred to in this paragraph and in this disclosure, peptides on a peptide microarray can be cyclic peptides.

According to further embodiments, each 5-mer peptide 308 comprising the population of up to 2.9 million peptides 310 of the peptide microarray 300 may be synthesized with 5 cycles of wobble synthesis in each of the N-terminus and of the C-terminus (see, for example, 306 and 306' FIG. 3). As used herein "wobble synthesis" refers to synthesis (through any of the means disclosed herein) of a sequence of peptides (either constant or random; e.g., cyclic peptides) which are positioned at the N-terminus or C-terminus of the 5-mer peptide 308 of interest. As illustrated in FIG. 3, the specific amino acids comprising the wobble synthesis at either the N- or C-terminus are represented by a "Z." According to various embodiments, wobble synthesis may include any number of peptides at the N-terminus or C-terminus, for example 1, 2, 3, 4, 5, 6, 7, 8, 9, 10 or more, even for example 15 or 20 peptides (e.g., cyclic peptides). Furthermore, wobble synthesis may comprise an N-terminus and C-terminus having the same or differing number of wobble synthesized peptides (e.g., cyclic peptides).

According to various embodiments, the wobble peptide compositions 306, 306' are flexible in terms of amino acid composition and in term of amino acid ratios/concentrations. For example, the wobble peptide compositions may comprise a mixture of 2 or more amino-acids. An illustrative embodiment of such flexible wobble mix includes a wobble peptide composition 306, 306' of glycine (G) and serine (S) at a ratio of 3:1. Other examples of a flexible wobble mixture include equal concentrations (e.g., equal ratios) of amino acids G, S, adenine (A), valine (V), aspartic acid (D), proline (P), glutamic acid (E), leucine (L), threonine (T) and/or equal concentrations (e.g., equal ratios) of amino acids L, A, D, lysine (K), T, glutamine (Q), P, F, V, tyrosine (Y). Other examples include the wobble peptide compositions 306, 306'comprising any of the 20 known amino acids, in equal concentrations.

As disclosed herein, the wobble peptide synthesis of the various embodiments allow for generating a peptide on a peptide microarray having a combination of random and directed synthesis amino acids. For example, a peptide on a peptide microarray may comprise a combined 15-mer peptide having a peptide sequence in the following format: ZZZZZ-5-mer-ZZZZZ, where Z is an amino-acid from a particular wobble oligopeptide mixture.

In some embodiments, a feature may contain $10^7$ peptides. In some such embodiments, the population complexity for each feature may vary depending on the complexity of the wobble mixture. As disclosed herein, creating such complexity using wobble synthesis in a semi-directed synthesis enables the screening of peptide binders on the array, using peptides with diversity up to $10^{12}$ per array.

In one embodiment, with reference to FIG. 3, a peptide microarray 300 comprising a solid support 302 having a reactive surface 304 (e.g., a reactive amine layer for example) with a population of peptides 310 (such as a population of 5-mers representing the entire human proteome) immobilized thereto is provided. The exemplary 5-mer peptides comprising the population of peptides 310, according to such embodiment, does not include any of the amino acids C and M, does not include amino acid repeats of 2 or more amino acids and does not include the amino acid motif HPQ. According to such illustrative embodiment, such population of peptides 310 representing the entire human proteome would comprise 1,360,732 individual peptides comprising the population 310. In some embodiments, duplicates or repeats may be placed on the same peptide microarray. For example, a population 310 comprising a single duplicate would comprise 2,721,464 individual peptides. Additionally, the population of peptides 310 each comprise an N-terminal and C-terminal wobble synthesis oligopeptide 306, 306', which for example consists of five amino acids each consisting of the amino acid glycine and serine in a 3:1 ratio, respectively. Such peptides can be cyclized as described herein.

Figure 4:
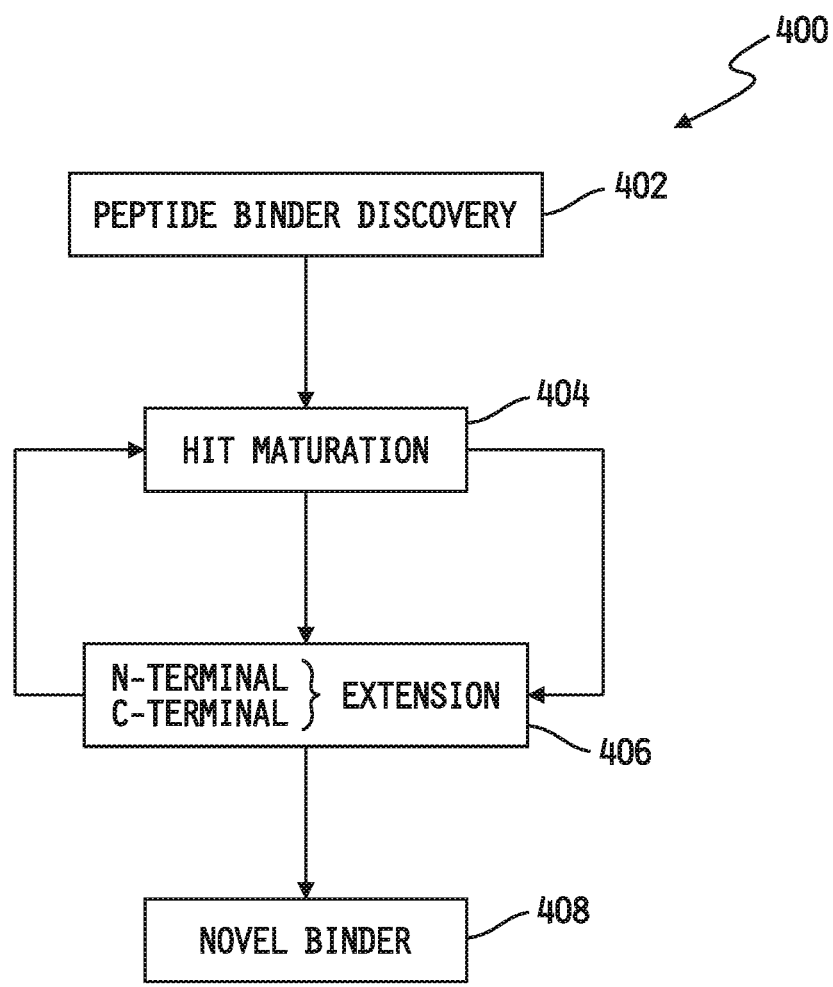
FIG. 4 is a schematic illustration of an embodiment of a process of the present disclosure.

Referring generally now to step 402 of process 400 of FIG. 4, in use an exemplary peptide microarray 300 (FIG. 3; such peptide microarray may comprise cyclic peptides as described herein) is exposed to a target of interest (as with standard peptide microarray practice), whereby the target of interest may bind at any of the population of peptides 310 (e.g., cyclic peptides), independent of the other peptides comprising the population 310. After exposure to the target of interest, binding of the target of interest to the peptide binders (e.g., cyclic peptides) is assayed, for example, by way of exposing the complex of the individual peptides (e.g., cyclic peptides) of the population 310 and target of interest to an antibody (specific for the target of interest) which has a reportable label (e.g., peroxidase) attached thereto. Because the peptide sequence of each 5-mer, at each location on the peptide microarray, is known, it is possible to chart/quantify/compare/contrast the sequences (and binding strengths) of the binding of the target of interest to specific 5-mer peptide sequences (e.g., cyclic peptides). One such method of comparing the protein binding to the peptides (e.g., cyclic peptides) comprising the population 310 is to review the binding in a principled analysis distribution-based clustering, such as described in, *Standardizing and Simplifying Analysis of Peptide Library Data*, Andrew D White et al, J Chem Inf Model, 2013, 53(2), pp 493-499, and illustrated herein. As is exemplified herein, the clustering of target of interest-5-mer binding (a.k.a., "hits") (shown in a principled analysis distribution-based clustering) indicates 5-mers having overlapping peptide sequences. As demonstrated in greater detail below, from the overlapping peptide sequences (of each cluster), a "core hit" peptide sequence or core binder sequence (e.g., a peptide sequence shared by the prominent target of interest-peptide binding events of the peptide microarray) can be identified, or at least hypothesized and constructed for further evaluation. (Note, it should be understood that a peptide microarray, as exemplified herein, may identify more than one "core hit" peptide sequence (i.e., core binder sequence). It should further be understood that it is possible for the "core hit" peptide sequence to comprise more amino acids than, for example, the 5-mer peptide binders comprising the population of peptides due to possible identification of overlapping and adjacent sequences during principled analysis distribution-based clustering).

V. Peptide Maturation:

Referring now to step 404 of process 400 graphically described in FIG. 4, upon identification of a core hit peptide sequence or core binder sequence (through the process of peptide binder discovery 402 disclosed, described and exemplified herein), a process of "peptide maturation" 404 whereby the core hit peptide sequence or core binder sequence is altered in various ways (through amino acid substitutions, deletions and insertions) at each position of the core hit peptide or core binder sequence in order to further optimize/verify the proper core hit sequence or core binder sequence. For example, according to some embodiments (for example, where the core hit peptide sequence (core binder sequence) comprises a given number of, such as 7, amino acids), a maturation array is produced. According to the instant disclosure, the maturation array may have, immobilized thereto, a population of core hit peptides (core binder sequence) whereby each amino acid in the core hit peptide (core binder sequence) has undergone an amino acid substitution at each position.

In order to further describe the process of hit maturation 404, an example/hypothetical core hit peptide or core binder sequence is described as consisting of a 5-mer peptide having the amino acid sequence -$M_1M_2M_3M_4M_5$- (SEQ ID NO: 202). According to the instant disclosure, hit maturation 404 may involve any of, or a combination of any or all of, amino acid substitutions, deletions and insertions at positions 1, 2, 3, 4 and 5. For example, in regard to the hypothetical core hit peptide or core binder sequence -$M_1M_2M_3M_4M_5$- (SEQ ID NO: 202), embodiments of the instant disclosure may include the amino acid M at position 1 being substituted with each of the other 19 amino acids (e.g., $A_1M_2M_3M_4M_5$- (SEQ ID NO: 203), $P_1M_2M_3M_4M_5$- (SEQ ID NO: 204), $V_1M_2M_3M_4M_5$- (SEQ ID NO: 205), $Q_1M_2M_3M_4M_5$- (SEQ ID NO: 206), etc.). Each position (2, 3, 4 and 5) would also have the amino acid M substituted with each of the other 19 amino acids (for example, with position 2 the substitutions would resemble, $M_1A_2M_3M_4M_5$- (SEQ ID NO: 207), $M_1Q_2M3M4M5$- (SEQ ID NO: 208), $M_1P_2M_3M_4M_5$- (SEQ ID NO: 209), $M_1N_2M_3M_4M_5$- (SEQ ID NO: 210), etc.). It should be understood that a peptide (immobilized on an array) is created comprising the substituted and/or deleted and/or inserted sequences of the core hit peptide or core binder sequence.

In some embodiments of hit maturation 404 according to the instant disclosure, a double amino acid substitution may be performed. A double amino acid substitution includes altering the amino acid at a given position (e.g., a M→P substitution, for example at position 1) and then substituting the amino acid at position 2 with each of the other 19 amino acids the amino acid at position 2. This process is repeated until all possible combinations of positions 1 and 2 are combined. By way of example, referring back to the hypothetical core hit peptide or core binder sequence having a 5-mer peptide with amino acid sequence -$M_1M_2M_3M_4M_5$- (SEQ ID NO: 202), a double amino acid substitution with regard to positions 1 and 2 may include, for example, a M→P substitution at position 1, and then a substitution of all 20 amino acids at position 2 (e.g., -$P_1A_2M_3M_4M_5$- (SEQ ID NO: 211), -$P_1F_2M_3M_4M_5$- (SEQ ID NO: 212), -$P_1V_2M_3M_4M_5$- (SEQ ID NO: 213), -$P_1E_2M_3M_4M_5$- (SEQ ID NO: 214), etc.), a M→V substitution at position 1, and then a substitution of all 20 amino acids at position 2 (e.g., -$V_1A_2M_3M_4M_5$- (SEQ ID NO: 215), -$V_1F_2M_3M_4M_5$- (SEQ ID NO: 216), -$P_1V_2M_3M_4M_5$- (SEQ ID NO: 217), -$V_1E_2M_3M_4M_5$- (SEQ ID NO: 218), etc.), M→A substitution at position 1, and then a substation of all 20 amino acids at position 2 (e.g., $A_1A_2M_3M_4M_5$- (SEQ ID NO: 219), -$A_1F_2M_3M_4M_5$- (SEQ ID NO: 220), -$A_1V_2M_3M_4M_5$- (SEQ ID NO: 221), -$A_1E_2M_3M_4M_5$- (SEQ ID NO: 222), etc.).

In some embodiments of hit maturation 404 according to the instant disclosure, an amino acid deletion for each amino acid position of the core hit peptide may be performed. An amino acid deletion includes preparing a peptide including the core hit peptide sequence or core binder sequence, but deleting a single amino acid from the core hit peptide sequence or core binder sequence (such that a peptide is created in which the amino acid at each peptide is deleted). By way of example, referring back to the hypothetical core hit peptide or core binder sequence having a 5-mer peptide with amino acid sequence -$M_1M_2M_3M_4M_5$- (SEQ ID NO: 202), an amino acid deletion would include preparing a series of peptides having the following sequences -$M_2M_3M_4M_5$- (SEQ ID NO: 223); -$M_1M_3M_4M_5$- (SEQ ID NO: 223); -$M_1M_2M_4M_5$- (SEQ ID NO: 223); -$M_1M_2M_3M_5$- (SEQ ID NO: 223); and -$M_1M_2M_3M_4$- (SEQ ID NO: 223). It should be noted that, following an amino acid deletion of the hypothetical 5-mer, 5 new 4-mers are created. According to some embodiments of the instant disclosure an amino acid substitution or a double amino acid substation scan can be performed for each new 4-mer generated.

Similar to the amino acid deletion scan discussed above, some embodiments of hit maturation 404 disclosed herein may include an amino acid insertion scan, whereby each of the 20 amino acids is inserted before and after every position of the core hit peptide or core binder sequence. By way of example, referring back to the hypothetical core hit peptide or core binder sequence having a 5-mer peptide with amino acid sequence -$M_1M_2M_3M_4M_5$- (SEQ ID NO: 202), an amino acid insertion scan would include the following sequences, -$XM_1M_2M_3M_4M_5$- (SEQ ID NO: 224); -$M_1XM_2M_3M_4M_5$- (SEQ ID NO: 225); -$M_1M_2XM_3M_4M_5$- (SEQ ID NO: 226); -$M_1M_2M_3XM_4M_5$- (SEQ ID NO: 227); -$M_1M_2M_3M_4XM_5$- (SEQ ID NO: 228); and -$M_1M_2M_3M_4M_5X$- (SEQ ID NO: 229) (where X represents an individual amino, selected from the 20 known amino acids or a specific, defined subset of amino acids, whereby a peptide replicate will be created for each of the 20 or defined subset of amino acids).

It should also be understood that the amino acid-substituted peptides, double amino acid-substituted peptides, amino acid deletion scan peptides and amino acid insertion scan peptides described above may also include one, or both of, a N-terminal and C-terminal wobble amino acid sequence (similar to as described at 306, 306' of FIG. 3, for example). As with the N-terminal and C-terminal wobble amino acid sequences described in FIG. 3, the N-terminal and C-terminal wobble amino acid sequences may comprise as few as 1 amino acid or as many as 15 or 20 amino acids, and the N-terminal wobble amino acid sequence may be the same length as, longer than or shorter than the C-terminal wobble amino acid sequence. Further, the N-terminal and C-terminal wobble amino acid sequences may comprise any defined group of amino acids at any given ratios (for example, glycine and serine in a 3:1 ratio).

In a specific exemplified embodiment of hit maturation 404 described below, a core hit peptide or core binder sequence of 7 amino acids (e.g., a 7-mer) undergoes exhaustive single and double amino acid screens, and includes both N-terminal and C-terminal wobble amino acid sequences which comprise three amino acids (all glycine).

Once the various substitution, deletion and insertion variations of the core hit peptide or core binder sequence are prepared (for example, in immobilized fashion on a solid support such as a peptide microarray), the strength of binding of the purified, concentrated target of interest is assayed.

VI. Peptide Extension (N-Terminal and C-Terminal):

It is possible that motifs identified in 5-mer array experiments represent only short versions of optimal peptide binders. A strategy is described herein of identifying longer motifs by extending sequences selected from 5-mer arrays experiments by one or more amino acids from one or both N- and C-terminus. Starting from a selected peptide and adding one or more amino acids on each terminus, one can create an extension library for further selection. For example, starting from a single peptide and using all 20 natural amino acids, one can create an extension library of 160,000 unique peptides. In some embodiments, each of the extended peptides is synthesized in replicates.

Referring now to step 406 of process 400 graphically described in FIG. 4, upon maturation of the core hit peptide or core binder sequence (such that a more optimal amino acid sequence of the core hit peptide or core binder sequence is identified for binding the target of interest), the N-terminal and/or C-terminal positions undergo an extension step, whereby the length of the matured core hit peptide (also referred to as the mature core peptide binder sequence) 512 is further extended for increasing the specificity and affinity for the target of interest.

Figure 5:
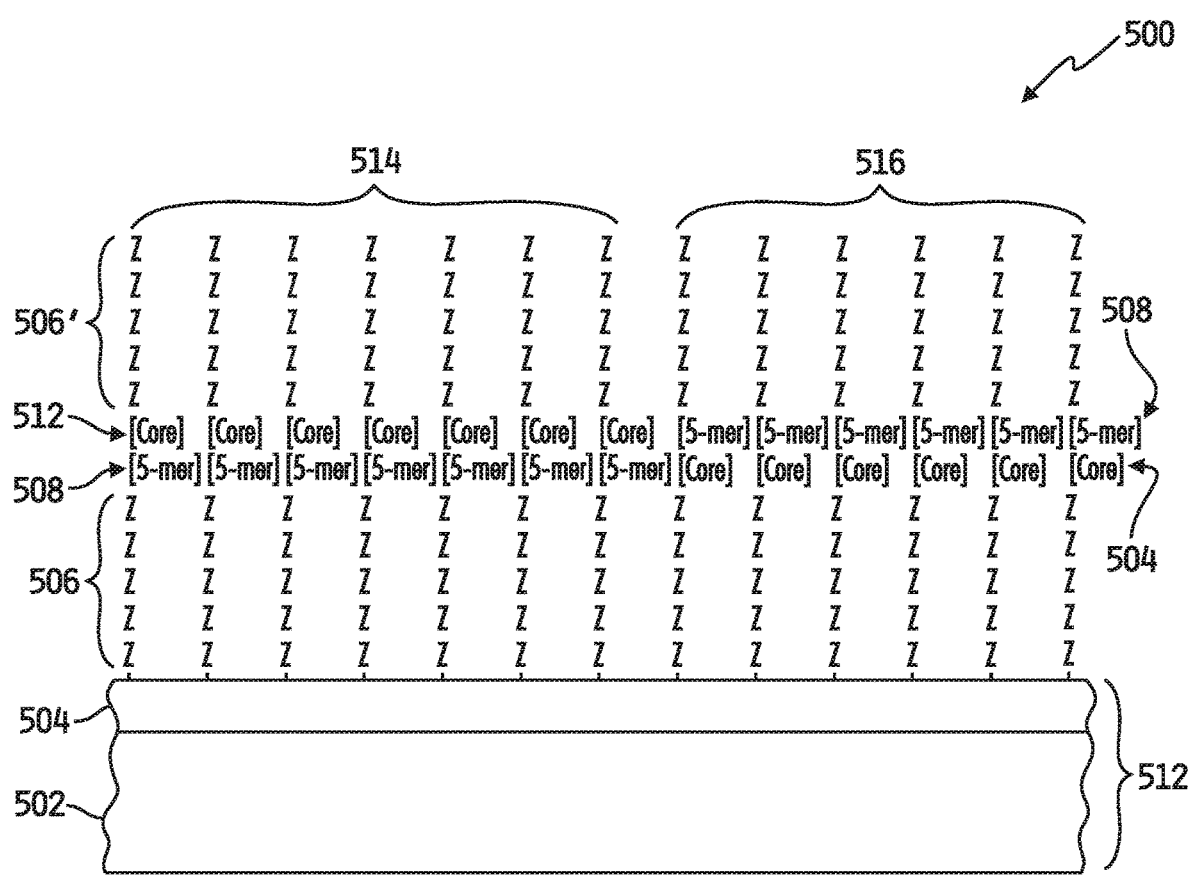
FIG. 5 is a schematic view illustrating another embodiment of an array comprising peptide probes thereon in accordance with the present disclosure.

According to various embodiments of N-terminal extension of the instant disclosure, and with reference to FIG. 5, once the matured core hit peptide sequence (also referred to as the mature core peptide binder sequence) 512 is identified through the maturation process (404 of FIG. 4), each specific peptide (represented as a population of 5-mers, 308 of FIG. 3) from the peptide binder discovery step (302, FIG. 3), is added (or synthesized onto) the N-terminal end of a matured core hit peptide 512. In this manner, the most C-terminal amino acid of each peptide 308 (of the population), exemplified as a population of 5-mers in FIG. 3, is added (or synthesized) directly adjacent to the most N-terminal amino acid of the matured core hit peptide 512.

Likewise, according to various embodiments of C-terminal extension of the instant disclosure, and with reference to FIG. 5, once the matured core hit peptide 512 is identified through the maturation process (404 of FIG. 4), each specific peptide of the population (represented as a population of 5-mers, 308 of FIG. 3) from the peptide binder discovery step (302, FIG. 3), is added (or synthesized onto) the C-terminal end of a matured core hit peptide 512. In this manner, the most N-terminus amino acid of each peptide sequence 308, exemplified as a population of 5-mers in FIG. 3, is added (or synthesized) directly adjacent to the most C-terminal amino acid of the matured core hit peptide 512.

According to some embodiments of the instant disclosure (FIG. 5) one of, or both of, the matured core hit peptides used in C-terminal extension and N-terminal extension may also include one, or both of, a N-terminal and C-terminal wobble amino acid sequence (similar to as described at 306, 306' of FIG. 3). As with the N-terminal and C-terminal wobble amino acid sequences described in FIG. 3, the N-terminal and C-terminal wobble amino acid sequences may comprise as few as 1 amino acid or as many as 15 or 20 amino acids (or more), and the N-terminal wobble amino acid sequence may be the same length as, longer than, or shorter than the C-terminal wobble amino acid sequence. Further, the N-terminal and C-terminal wobble amino acid sequences may comprise any defined group of amino acids at any given ratios (for example, glycine and serine in a 3:1 ratio).

By way of example, on FIG. 5, a peptide extension array 500 is shown, having a population of peptides for N-terminal extension 514 and a population of peptides for C-terminal extension 516. Each population of peptides 514, 516 may contain the full population of peptides 310 from peptide microarray 300 (used in the step of peptide binder discovery 404). As further illustrated, each peptide of both populations of peptides 514, 516 may contain the same matured core hit peptide 512, each with a different peptide 508 (of the population of peptides from the peptide binder discovery step 302, FIG. 3). Also shown in FIG. 5, each peptide of the populations 514, 516 includes N-terminal and C-terminal wobble amino acid sequences.

In one embodiment, an extension array 500 (including populations 514 and 516) is exposed to a concentrated, purified target of interest (as in peptide binder discovery, step 401 of process 400), whereby the target of interest may bind at any peptide (e.g., cyclic peptides) of either population 514, 516, independent of the other peptides comprising the populations 514, 516. After exposure to the target of interest, binding of the target of interest to the peptide of the populations (e.g., cyclic peptides) 514, 516 is assayed, for example, by way of exposing the complex of the individual peptides of the populations (e.g., cyclic peptides) 514, 516 and the target of interest to an antibody (specific for the target of interest) which has a reportable label (e.g., peroxidase) attached thereto (it should also be understood the target of interest may be directly labelled with a reporter molecule). Because the peptide 508 (of each 5-mer) for each location on the array, is known (e.g., a cyclic peptide), it is possible to chart/quantify/compare/contrast the sequences (and binding strengths) of the binding of the target of interest to the specific peptide (e.g., cyclic peptide) comprising the matured core hit peptide 512 with the respective peptide 508 (e.g., cyclic peptide). An exemplary method of comparing the target of interest binding to the matured core hit peptide 512-peptide 508 combination (comprising either population 514 or 516) is to review the binding strength in a principled analysis distribution-based clustering, such as described in, *Standardizing and Simplifying Analysis of Peptide Library Data*, Andrew D White et al, J Chem Inf Model, 2013, 53(2), pp 493-499, and illustrated herein (for example at Graphs 3 and 4). As is exemplified herein, clustering of protein binding to the respective peptides (e.g., cyclic peptides) (of populations 514, 516) shown in a principled analysis distribution-based clustering indicates peptide 5-mers 508 having overlapping peptide sequences. As demonstrated in greater detail below, from the overlapping peptide sequences (of each cluster), a mature, extended core peptide binder sequence can be identified, or at least hypothesized and constructed for further evaluation. In some embodiments of the instant application, a mature, extended core peptide binder sequence undergoes a maturation process (as described and exemplified herein and illustrated at step 404 of FIG. 4).

Additional rounds of optimization of extended peptide binders are also possible. For example, a third round of binder optimization may include extension of the sequences identified in the extension array experiments with glycine (G) amino acid. Other optimizations may include creating double substitution/deletion libraries that include all possible single and double substitution/deletion variants of the reference sequence, i.e., the peptide binder optimized and selected in any of the previous steps. In one embodiment, after or during any of the maturation and/or extension processes described herein the peptides can be cyclized.

VII. Specificity Analysis of Mature, Extended Core Peptide Binder Sequence:

Following identification of a mature, extended core peptide binder sequence a specificity analysis may be performed by any method of measuring peptide affinity and specificity available in the art. One example of a specificity analysis includes a "Biacore™" system analysis which is used for characterizing molecules in terms of the molecule's interaction with a target of interest, the kinetic rates (of "on," binding, and "off," disassociation) and affinity (binding strength). Biacore™ is a trademark of General Electric Company and is available via the company website.

Figure 6:
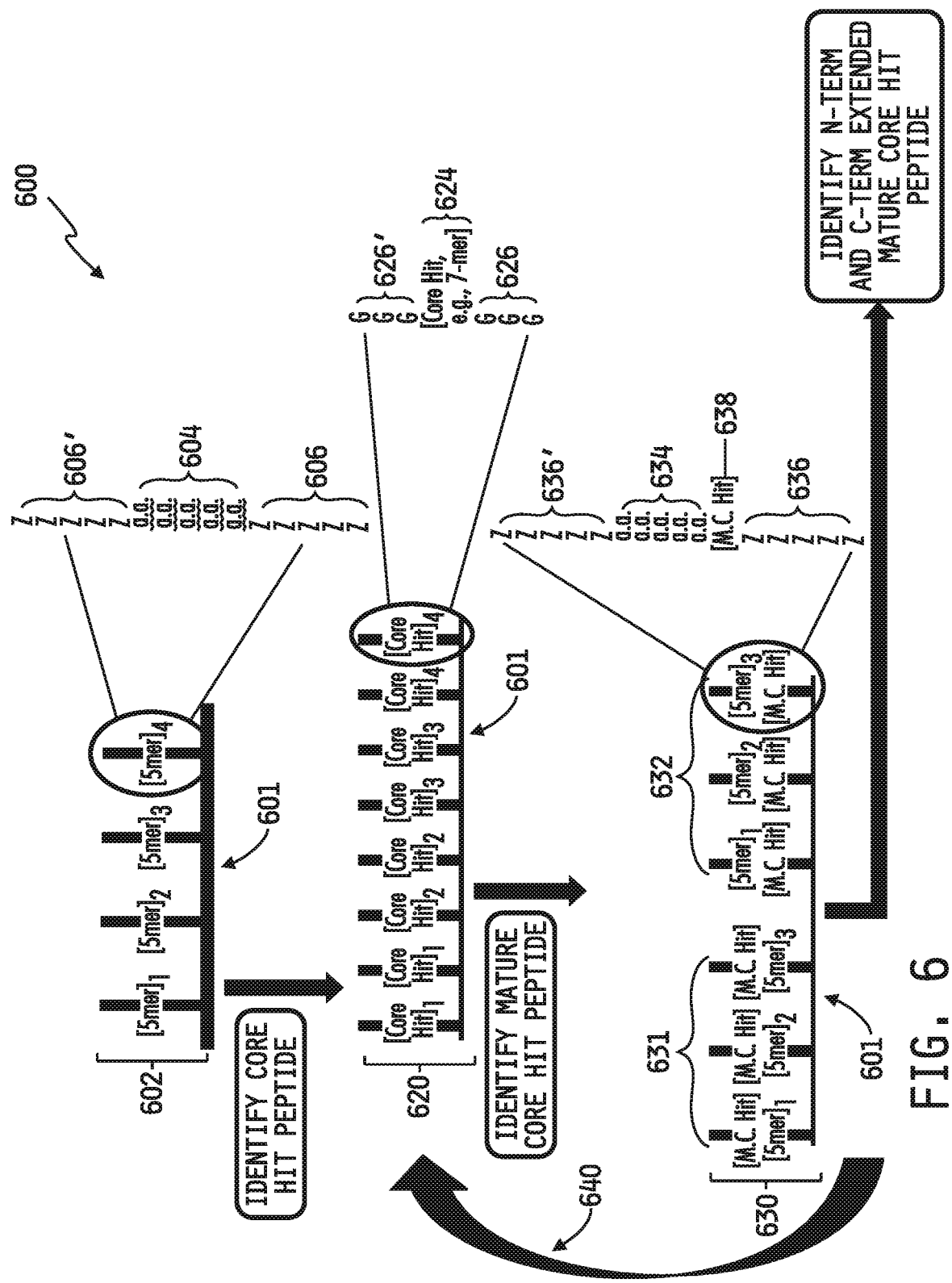
FIG. 6 is a schematic view depicting an embodiment of the process of FIG. 4.

FIG. 6 is a brief schematic overview of the method of novel peptide binder identification (e.g., process 400 of FIG. 4). As shown, the peptide binder discovery 602 is performed by preparing (e.g., through maskless array synthesis) a population of peptides on a peptide microarray 601. As illustrated, each peptide includes 5 "cycles" of N-terminal wobble synthesis 606' and C-terminal wobble synthesis 606 (e.g., both N- and C-terminal wobble synthesis comprises five amino acids). It should be understood that the wobble synthesis of the C- and N-terminal may comprise any composition as noted above (for example, only amino acids G and S, in a 3:1 [G:S] ratio). Each peptide is also shown as comprising a 5-mer peptide binder 604, which as noted above may comprise up to 2.9 million different peptide sequences such that an entire human proteome is represented. Further, it should be noted that the different peptide binders 604 may be synthesized according to specific "rules" (for example, no C or M amino acids, no repeats of the same amino acid in consecutive order, and no HPQ amino acid motifs). As described above, a target of interest (for example, in purified and concentrated form) is exposed to the peptide binders 604, and binding is scored (e.g., by way of a principled clustering analysis), whereby a "core hit peptide" sequence or core binder sequence is identified based on overlapping binding motifs.

Upon identification of a core hit peptide sequence or core binder sequence, an exhaustive maturation process 620 may be undertaken. In some embodiments, the core hit peptide or core binder sequence (exemplified as a 7-mer, 624) is synthesized on a peptide microarray 601 with both N- and C-terminal wobble (shown at step 620 as 3 cycles of N- and C-terminal wobble of only G amino acid, although the wobble amino acid may vary as noted above). In some embodiments of exhaustive maturation, a peptide is synthesized on the peptide microarray 601 wherein every amino acid position of the core hit peptide or core binder sequence 624 is substituted with each of the other 19 amino acids or a double amino acid substitution (as described above) is synthesized on the peptide microarray 601 or an amino acid deletion scan is synthesized on the peptide microarray 601, or an amino acid insertion scan is synthesized on the peptide microarray 601. In some cases, all of the above maturation processes are performed (and the repeated as described above for the new peptides generated as a result of the amino acid deletion and insertion scans). Upon synthesis of the maturation array 620 comprising the various peptides (inclusive of the substitutions, deletions and insertions described herein), the target of interest is exposed to the modified core hit peptides or core binder sequence 624 synthesized on the maturation array 620, and strength of binding is assayed, whereby a "matured core hit peptide" (mature core peptide binder sequence) is identified.

After identification of a "matured core hit peptide" sequence (mature core peptide binder sequence), one of, or both of N- and C-terminal extension may be performed (shown at 630 as including both N-terminal extension 632 and C-terminal extension 631). N-terminal and C-terminal extension involve the synthesis of matured core hit peptides (mature core peptide binder sequence) having the population of (e.g., 5-mer) peptide binders 604 synthesized at the N-terminal or C-terminal respectively. As shown at 631, C-terminal extension involves five rounds of wobble synthesis (as described above) 636 and the population of 5-mer peptide binders 634 being synthesized C-terminally of the matured core hit peptide 638, then another 5 cycles of wobble synthesis 636' N-terminally. Similarly, as shown at 632, N-terminal extension involves five rounds of wobble synthesis (as described above) 636 being synthesized C-terminally of the matured core hit peptide (mature core peptide binder sequence) 638, then the population of 5-mer peptide binders 634 and another 5 cycles of wobble synthesis 636' synthesized N-terminally (of the matured core hit peptide (mature core peptide binder sequence) 638). Upon synthesis of the extension array 630 comprising the various extension peptides (inclusive of C-terminal and N-terminal extension peptides), the target of interest is exposed to the C-terminal and N-terminal extension peptide populations 631, 632 synthesized on the extension array 630, and binding is scored (e.g., by way of a principled clustering analysis), whereby a C-terminally, N-terminally mature, extended core peptide binder sequence is identified. As represented by arrow 640, according to some embodiments, after the mature, extended core peptide binder sequence is identified, the maturation process 620 for the mature, extended core peptide binder sequence may be repeated (in any way as described above), and then the extension process repeated for any altered peptide resulting therefrom. In one embodiment, after or during any of the maturation and/or extension processes described herein the peptides can be cyclized as described herein.

Example 1

FLAG Sequence Maturation

A fragmented peptide tag was designed to be specific for the anti-FLAG antibody near the N-terminus and C-terminus of the peptide tag, while having low specificity in the middle of the sequence to assist with attachment to a microarray surface through an amino acid side chain. To design such a tag, the FLAG tag was matured to possess specificity on the both ends of the tag. A maturation of the FLAG (GDYKDDDDKGG (SEQ ID NO: 232)) tag was performed with the tag in linear form. Each amino acid in the 11 mer peptide was individually substituted with each of the remaining 19 amino acids. As further described below, the process was repeated with modified sequences until the desired specificity at each position was achieved.

Example 2

FLAG-Based Sequence Maturation Binding Assay

Figure 25:
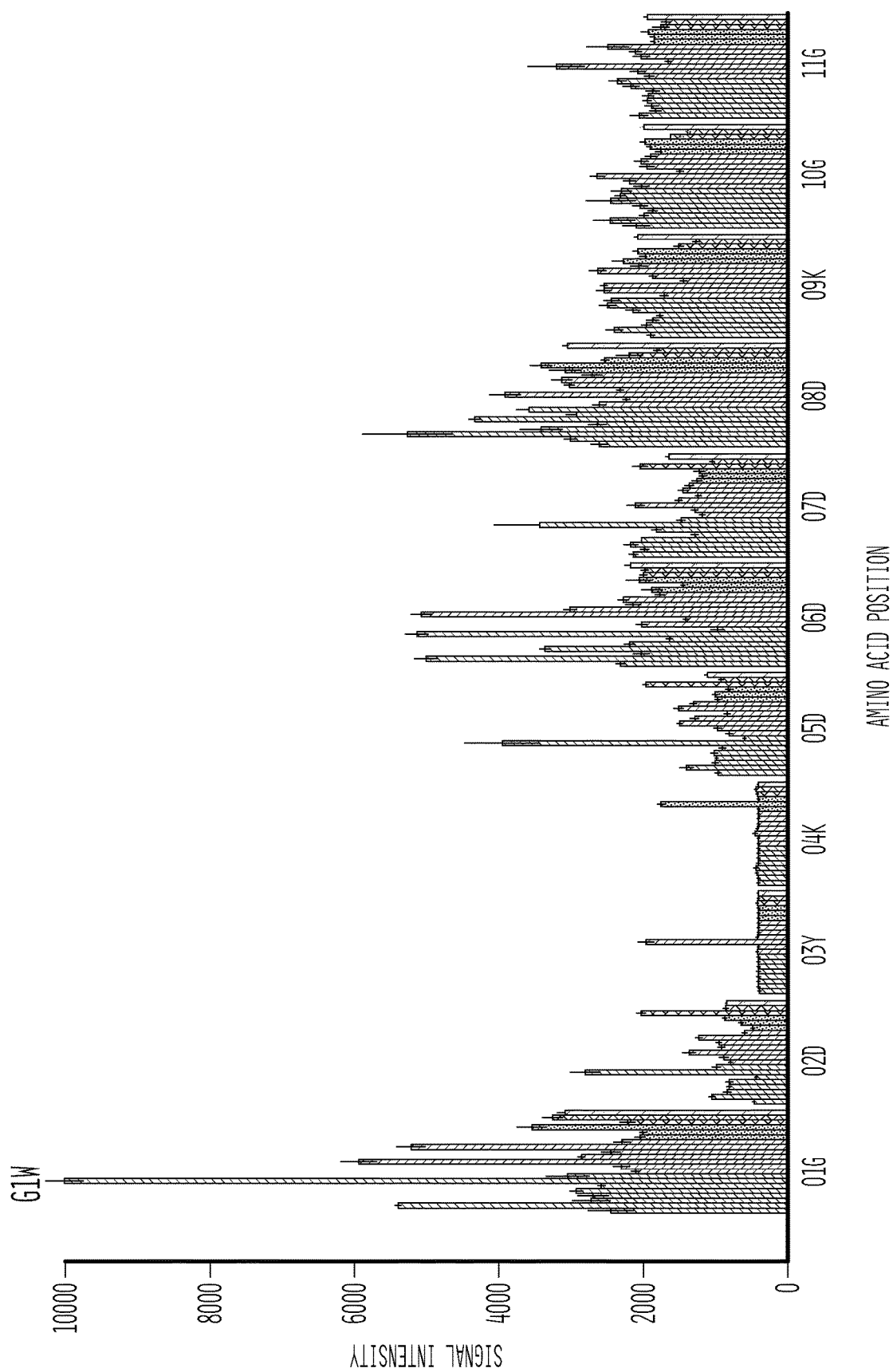
FIG. 25 is a maturation plot showing signal intensity of peptides formed by single mutations of the FLAG sequence (GDYKDDDDKGG (SEQ ID NO: 232)).

Referring to FIG. 25, the initial FLAG sequence (GDYKDDDDKGG (SEQ ID NO: 232)) was modified at each of positions 1-11 individually with each of the remaining 19 natural amino acids, and signal intensity (y-axis) was measured. Mutation of position 1 of the sequence to tryptophan (G1W) led to the strongest increase in signal intensity.

Figure 26:
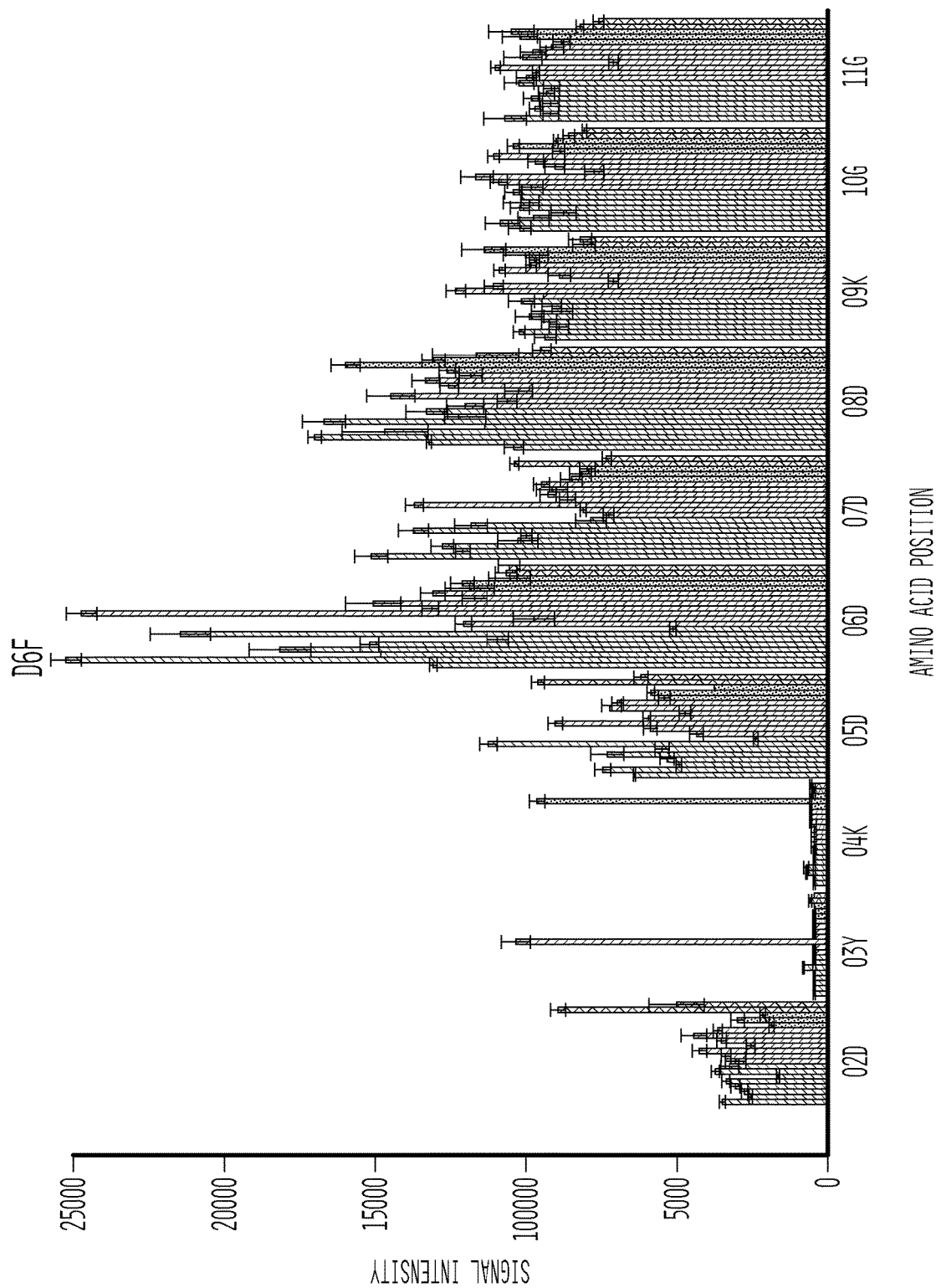
FIG. 26 is a maturation plot showing signal intensity of peptides formed by single mutations of the G1W-FLAG sequence (WDYKDDDDKGG (SEQ ID NO: 234)).

Referring to FIG. 26, the G1W-FLAG tag (WDYKDDDDKGG (SEQ ID NO: 234)) was modified at each of positions 2-11 individually with each of the remaining 19 natural amino acids, and signal intensity (y-axis) was measured. Mutation of position 6 of the sequence to phenylalanine (D6F) led to the strongest increase in signal intensity.

Figure 27:
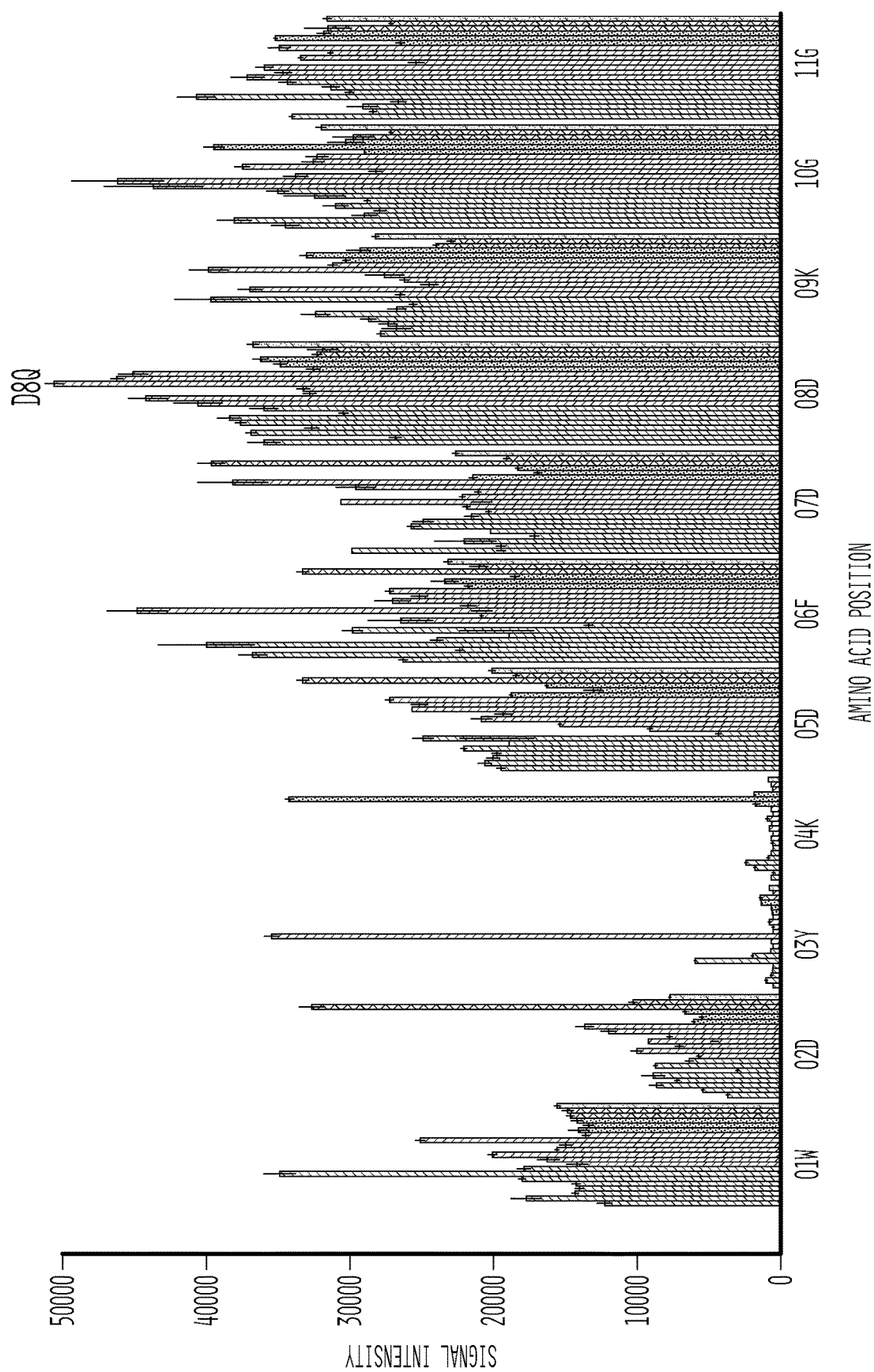
FIG. 27 is a maturation plot showing signal intensity of peptides formed by single mutations of the G1W, D6F-FLAG sequence (WDYKDFDDKGG (SEQ ID NO: 235)).

Referring to FIG. 27, the G1W, D6F-FLAG tag (WDYKDFDDKGG (SEQ ID NO: 235)) was modified at each of positions 1-11 individually with each of the remaining 19 natural amino acids, and signal intensity (y-axis) was measured. Mutation of position 8 of the sequence to glutamine (D6F) led to the strongest increase in signal intensity.

Figure 28:
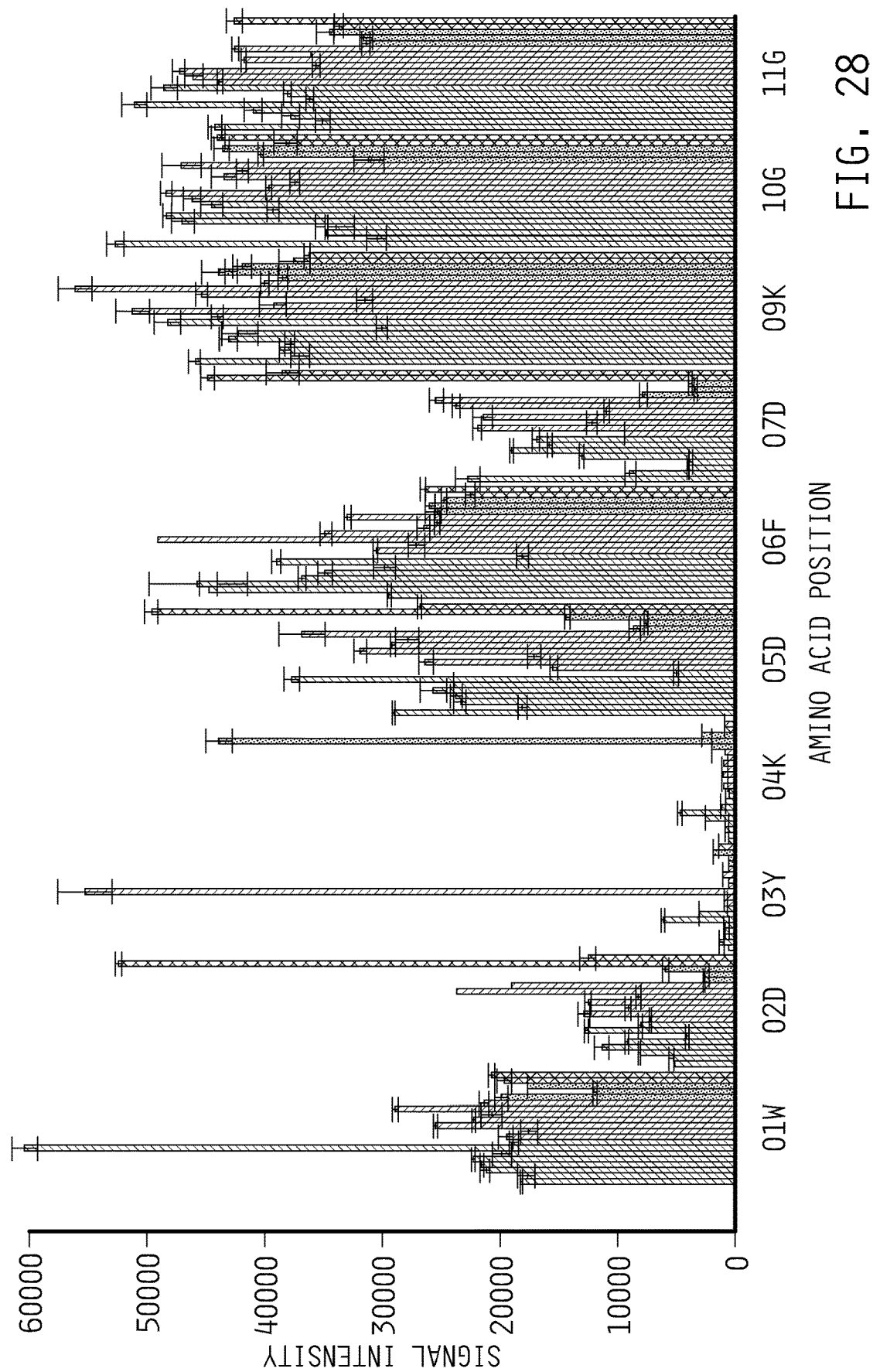
FIG. 28 is a maturation plot showing signal intensity of peptides formed by single mutations of the G1W, D6F, D8Q-FLAG sequence (WDYKDFDQKGG (SEQ ID NO: 236)).

Referring to FIG. 28, the matured G1W, D6F, D8Q-FLAG tag (WDYKDFDQKGG (SEQ ID NO: 236)) was modified at each of positions 1-7 and 9-11 individually with each of the remaining 19 natural amino acids, and signal intensity (y-axis) was measured. The matured FLAG tag showed specificity for the anti-FLAG antibody on the N-terminus (position 1-4) and the C-terminus (position 7-8) of the peptide. The matured FLAG tag also had a position of low specificity (position 6) where a cyclization amino acid was inserted for attaching the fragmented sequence to a microarray, as described in Example 5.

Example 3

Myc-Based Sequence Maturation

A fragmented protein tag was designed to be specific for the anti-Myc antibody near the N-terminus and C-terminus of the peptide tag, while having low specificity in the middle of the sequence to assist with attachment to a microarray surface through an amino acid side chain. It is to be understood that in some embodiments the amino acid attached to the microarray surface can be near either end of the peptide tag and not necessary closer to the middle of the peptide tag. To design such a tag, the Myc tag was matured to possess specificity on the both ends of the tag. A maturation of the Myc (EQKLISEEDLG (SEQ ID NO: 233)) tag was performed with the tag in the linear form. Each amino acid in the 11 mer peptide was substituted with each of the remaining 19 amino acids. As further described below, the process was repeated until the desired specificity at each position was achieved.

Example 4

Myc Sequence Maturation Binding Assay

Figure 29:
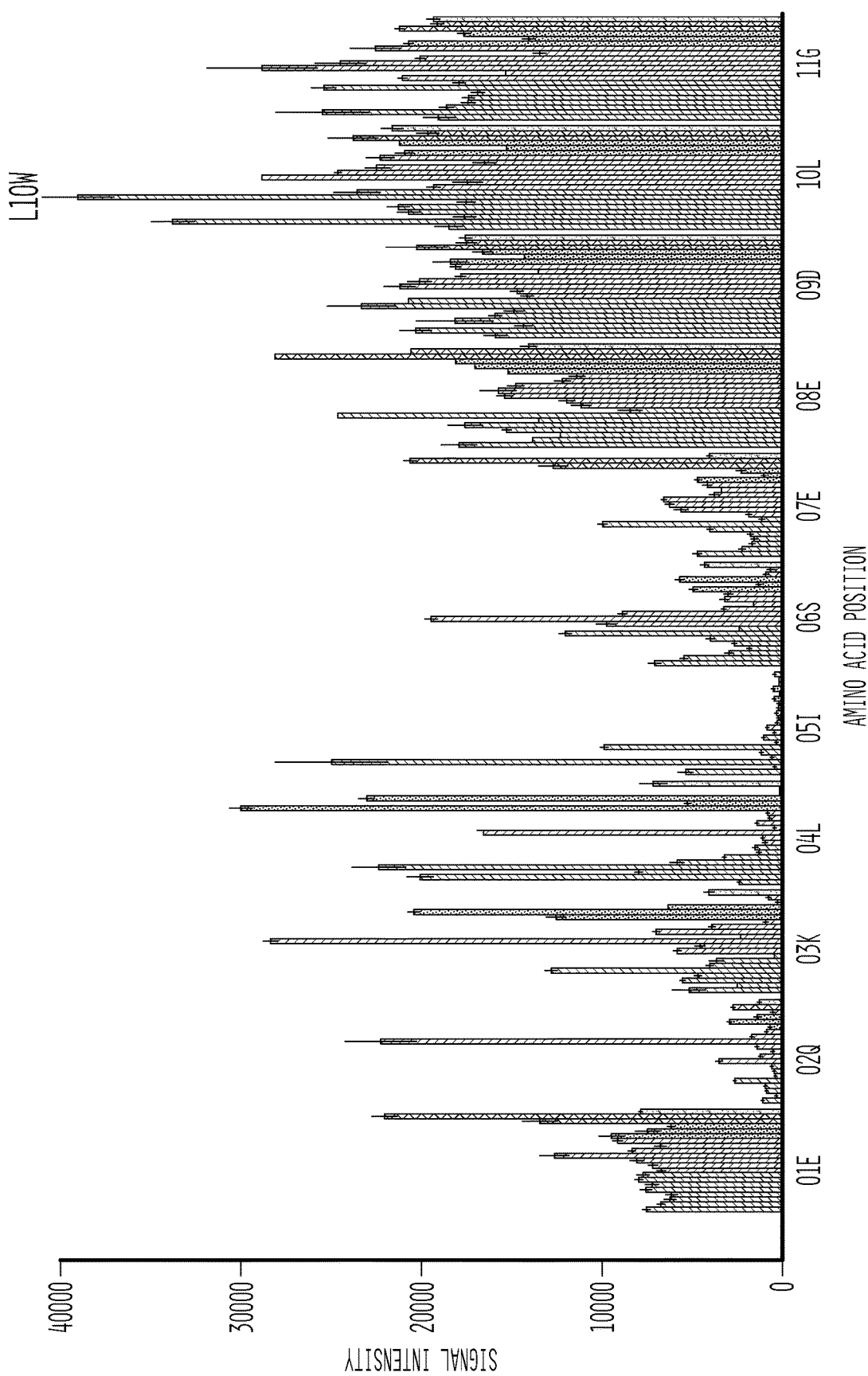
FIG. 29 is a maturation plot showing signal intensity of peptides formed by single mutations of the Myc sequence (EQKLISEEDLG (SEQ ID NO: 233)).

Referring to FIG. 29, the initial Myc sequence (EQKLISEEDLG (SEQ ID NO: 233)) was modified at positions 1-11 and signal intensity (y-axis) was measured. Mutation of position 10 of the sequence to tryptophan (L10W) led to the strongest increase in signal intensity.

Figure 30:
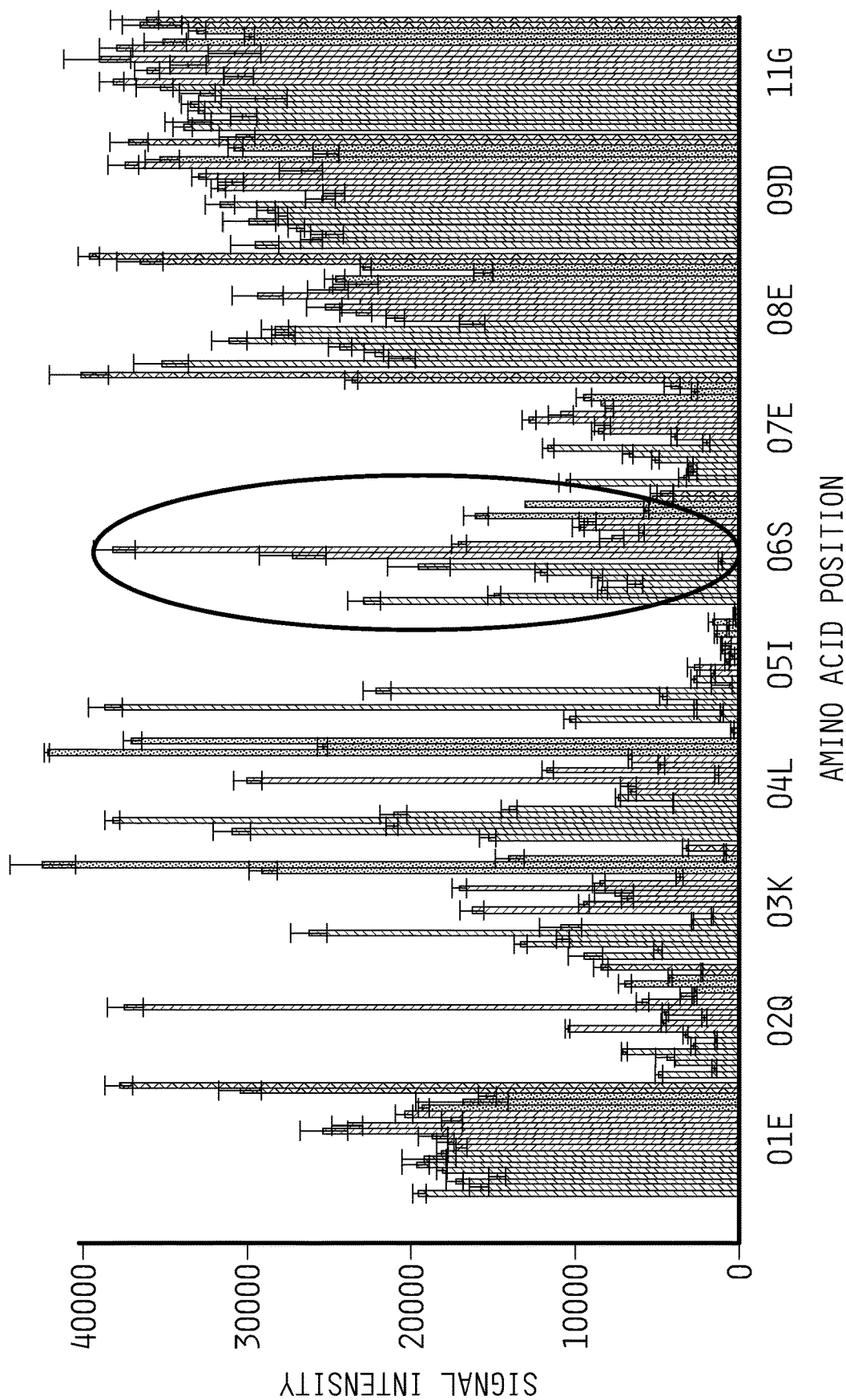
FIG. 30 is a maturation plot showing signal intensity of peptides formed by single mutations of the L10W-Myc sequence (EQKLISEEDWG (SEQ ID NO: 237)).

Referring to FIG. 30, the matured L10W-Myc tag (EQKLISEEDWG (SEQ ID NO: 237)) was modified at each of positions 1-9 and 11 individually with each of the remaining 19 natural amino acids, and signal intensity (y-axis) was measured. Here, the Myc tag had strong specificity on the N-terminus (position 1-5) and moderate specificity on the C-terminus. As mutation of position 7 appeared to limit antibody binding, position 6 was chosen for the cyclization amino acid so that specificity is achieved on the N- and C-terminus.

Example 5

Cyclization Tag Assays

With the matured linear protein tags at hand, the linear peptides were formed on a microarray where the tags were fragmented across the N- and C-terminus of the peptide such that upon cyclization, the complete protein tag is formed. The peptides were split around the low specificity position identified according to Examples 2 and 4 (position 6, for both tags), and that position was substituted with allyl-E (see FIG. 1). A flexible linker (Z) was inserted between the two peptide tag fragments to increase flexibility. Z was a 3:1 mixture of Gly:Ser. The linear peptide sequences are shown in Table 1 for the FLAG- and Myc-based sequenced in the row titled "Cyclization tag." In addition to the cyclization tags, two controls were compared to each tag. The matured linear sequences identified according to Examples 2 and 4 (shown in Table 1 in the row titled "Linear control") were formed on the microarray and tested as positive controls. The fragmented tag without the presence of the cyclization amino acid, allyl-E, was added to serve as a negative control, as shown in the row titled "fragmented control." For the fragmented control, allyl-E was substituted by a glycine such that the sequence was unable to undergo cyclization and, thus, served as surrogate for a failed cyclization reaction.

TABLE 1

Cyclization tags and controls

| Label | FLAG tag Sequence | Myc tag Sequence |
|---|---|---|
| Cyclization tag | DQKGGZZZZWDYKD{allyl-E} (SEQ ID NO: 255) | EEDWGZZZZEQKLI{allyl-E} (SEQ ID NO: 256) |
| Fragmented control | DQKGGZZZZWDYKDG (SEQ ID NO: 257) | EEDWGZZZZEQKLIG (SEQ ID NO: 258) |
| Linear control | WDYKDFDQKGG (SEQ ID NO: 236) | EQKLISEEDWG (SEQ ID NO: 237) |

Arrays containing the six sequences shown in Table 1 were synthesized and cyclization was performed via amide bond formation between the N- and C-terminus according to Example 8. After cyclization, the side chains were deprotected.

The array was bound with anti-FLAG and anti-Myc antibodies labeled with the Cy3 and Cy5 fluorophores, respectively, as described in Example 6.

Figures 32A, 32B, 32C:
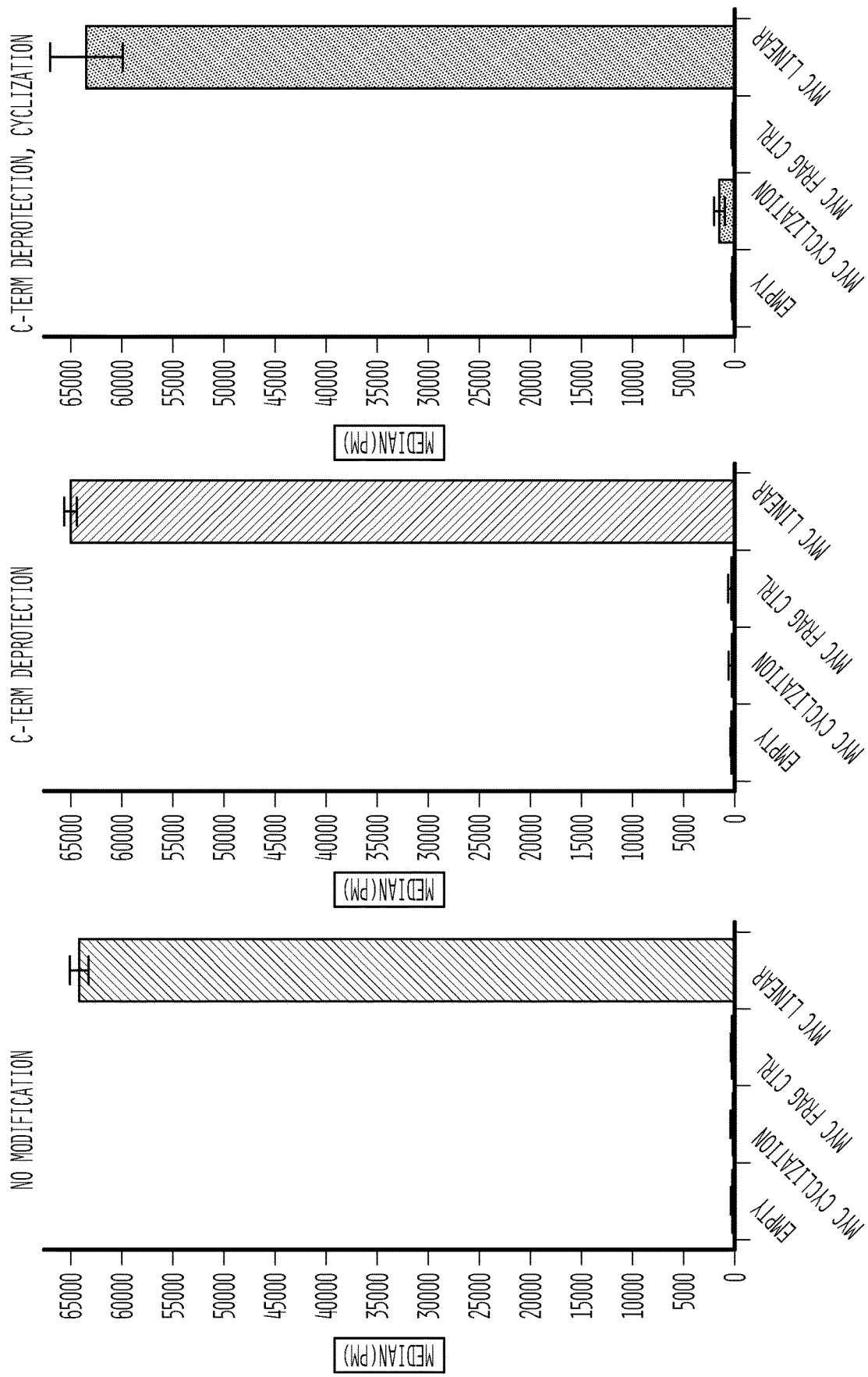
FIG. 32A is a chart showing signal intensity of anti-Myc protein applied to an empty control, a cyclization tag before deprotection and cyclization, a fragmented control, and a linear control.
FIG. 32B is a chart showing signal intensity of anti-Myc protein applied to an empty control, a cyclization tag after deprotection and before cyclization, a fragmented control, and a linear control.
FIG. 32C is a chart showing signal intensity of anti-Myc protein applied to an empty control, a cyclization tag after cyclization, a fragmented control, and a linear control.

For the FLAG sequences, the resulting median fluorescence was measured according to Example 7 and is shown for an empty control and each flag label in FIG. 31A (before deprotection of alkyl-E), FIG. 32B (after deprotection of alkyl-E but before cyclization), and FIG. 32C (after cyclization). For the Myc sequences, the resulting median fluorescence is shown below for an empty control and each flag label in FIG. 32A (before deprotection of alkyl-E), FIG. 32B (after deprotection of alkyl-E but before cyclization), and FIG. 32C (after cyclization).

For both the FLAG and Myc tags, the median fluorescence for the cyclization tags was higher than that of the fragmented control peptides. Thus, these sequences can be incorporated into standard array synthesis as cyclization quality control features.

Example 6

Anti-FLAG and Anti-Myc Binding to Peptide Microarray

Slides were bound with 2.8 ug Cy3 anti-FLAG mouse mAB (Sigma) and 2.25 ug Cy5 anti-Myc mouse mAB (Cell Signaling) in 30 mL binding buffer for 3 hours at room temperature. Binding buffer contained 1% alkali soluble casein and 0.05% tween-20 in 1×TBS, pH 7.4. After 30 minutes, slides were washed in 20 mM Tris-HCl, pH 7.8, 0.2 M NaCl, 1% SDS for 30 s followed by a 1 min wash in water and dried by spinning in microcentrifuge equipped with array holder.

Example 7

Fluorescence Scans/Data Analysis

Cy3 and Cy5 fluorescence intensity of the arrays was measured with MS200 scanner (Roche NimbleGen) at resolution 2 um, wavelength 532 nm or 635 nm, gain 25% and laser intensity 100%. Fluorescent signal intensities were extracted using image extraction software (Roche/NimbleGen). Data pre-processing, normalization and statistical tests were done in R. Data visualization and analysis were performed with Spotfire 6.5.0 (Tibco, Boston, Mass.) software platform.

Example 8

Cyclization Between N- and C-Terminus of Peptide Library

Peptide arrays were generated using maskless light-directed peptide array synthesis where all reactive amino acid side chains are protected with acid labile groups based on the methods of US 20120238477 A1, incorporated by reference herein. In this example, the microarray surface was comprised of a glass slide coated with a three-dimensional amine layer. The peptide library framework (C- to N-terminus) included a linker molecule (6-aminohexanoic acid, for example), Glu(OtBu) or Glu(OAll), and a variable peptide sequence described in the Library Design (below). Glu (OtBu) and Glu(OAll) were linked to the linker molecule through the gamma carboxylic acid of the side chain of glutamate where the C-terminus is protected with a t-Butyl ester or an allyl ester, respectively. Exemplary peptide library frameworks are shown in FIG. 7. In some embodiments, the variable peptide sequence consists of three to 15 amino acids. The N-terminus of the peptide library was a free amine. In order to cyclize the linear peptide library, the array was first treated with tetrakis(triphenylphosphine)palladium(0) (2 mM) in THF for 3 hours at room temperature to remove the OAll group from the C-terminus of the peptide library. To remove any residual palladium from the array, the slide was washed with 5% DIPEA and 5% sodium diethyldithiocarbamate in DMF for 5 minutes. The slide was washed with water for 1 minute and spun to dryness before cyclization. The array was then cyclized by coupling the N- to the C-terminus using a standard coupling procedure: slide was treated with activator (HOBt and HBTU, 20 mM each) and base (DIPEA, 2 M) for 3 hours at room temperature. The cyclized array was then side chain deprotected in trifluoroacetic acid (47.5 mL), triisopropylsilane (0.25 mL), and water (2.25 mL) for 30 min at room temperature. Following side chain deprotection, the slide was washed twice in methanol for 30 sec, four times in water for 10 seconds, 1×TBS with 0.05% tween-20 for 2 min, and then in 1×TBS for 1 minute. Finally, the slide was spun to dryness.

Example 9

Glutamate Deprotection

Figures 8A, 8B:
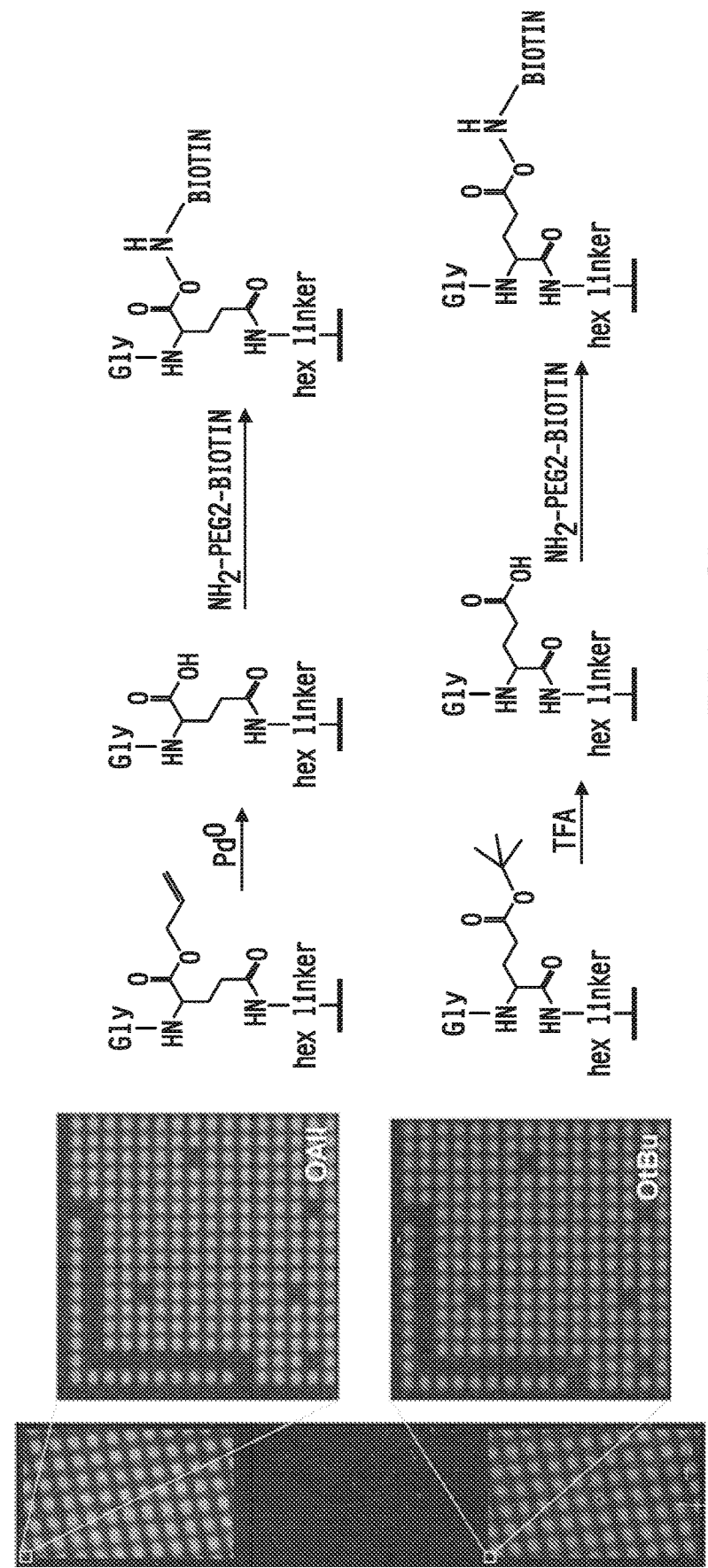
FIG. 8A is a slide image of subarrays of peptides each having a glutamate linker amino acid where (bottom) a linear library of peptides is formed from OtBu-protected variants of the glutamate linker amino acid after deprotection and biotin labelling, and (top) a cyclic library of peptides is formed from OAll-protected variants of the glutamate linker amino acid after deprotection and biotin labelling.
FIG. 8B is a schematic view depicting (bottom) deprotection of OtBu-protected variants of glutamate, followed by biotin labelling and (top) deprotection of OAll-protected variants of glutamate, followed by biotin labelling.

The microarray surface was comprised of a glass slide coated with a three-dimensional amine layer. Referring to FIG. 8B, to the amine substrate was coupled (C- to N-terminus) a 6-aminohexanoic acid linker molecule, a variable glutamate derivative, and glycine. The N-terminus of the peptide was free. The glutamate derivative included either a glutamate with OAll protection on the C-terminus (where the gamma carboxylic acid of the side chain is reacted to the linker, top subarray) or a glutamate with OtBu protection on the side chain carboxylic acid (the C-terminus is reacted with the linker, bottom subarray). The OtBu group was then removed by immersing the slide in a solution of trifluoroacetic acid (47.5 mL), triisopropylsilane (0.25 mL), and water (2.25 mL) for 30 min at room temperature. To remove all traces of TFA, the slide was washed twice in methanol for 30 sec, four times in water for 10 seconds, 1×TBS with 0.05% tween-20 for 2 min, and then 1×TBS for 1 minute. Finally, the slide was spun to dryness. Then, the slide was treated with tetrakis(triphenylphosphine)palladium(0) (2 mM) in THF for 3 hours at room temperature to remove the OAll groups. To remove any residual palladium from the array, the slide was washed with 5% DIPEA and 5% sodium diethyldithiocarbamate in DMF for 5 minutes. The slide was washed with water for 1 minute and spun to dryness. Following glutamate deprotection, the slide was reacted with 50 mM amine-PEG2-biotin activated with 100 mM EDC in 0.1 M MES buffer for 2 hours at room temperature. The slide was washed with wash 1 and water before being stained with streptavidin-Cy5, as detailed below.

As shown in FIG. 8A, the amine-PEG2-biotin labeled slide was the scanned for fluorescence. Both the top and bottom subarrays show consistent fluorescent intensity (2,500 and 2,000 fluorescent units for top and bottom subarrays, respectively), indicating successful removal of both the OtBu and OAll protecting groups.

Example 10

Cyclic/Linear Peptide Library Synthesis

The peptide libraries described herein were generated according to the method described in FIG. 9. Peptide libraries were generated on the same microarray slide, which included a linear peptide subarray and a cyclic peptide subarray. Each of the peptides in both subarrays included a C-terminus glutamate and a free N-terminus amino group. Each glutamate side chain was attached to the array surface via a 6-aminohexanoic acid linker molecule, as described in Example 9. Each peptide the linear peptide subarray was protected at its C-terminus by an OtBu protecting group. Each peptide in the cyclic peptide subarray was protected at its C-terminus by an OAll protecting group. Otherwise, the peptides in each subarray were identical. All side chains were protected with acid labile groups based on a two stage deprotection of the C-terminus for all peptides.

Still referring to FIG. 9, first, a C-terminus deprotection step was performed to remove the OAll protecting groups from the peptides of the cyclic peptide subarray by treating the slide with palladium(0) according to the procedure described in Example 9. The resulting deprotected peptides had free C-terminus carboxyl groups. The deprotection selectively resulted in the removal of OAll protecting groups from the cyclic peptide subarray, and did not remove the OtBu protecting groups from the peptides in the linear peptide subarray or the side chain protecting groups.

Next, a cyclization step was performed to cyclize the deprotected peptides in the cyclic peptide subarray. To perform the cyclization step, the side was treated according to the conditions described in Example 8, leading to head-to-tail cyclization via amide bond formation.

After the cyclization step, a C-terminus deprotection step was performed to remove the OtBu protecting groups from the peptides of the cyclic peptide subarray by treating the slide with TFA according to the procedure described in Example 9. The resulting deprotected peptides had free C-terminus carboxyl groups.

The resulting slide included a linear peptide subarray of linear peptides and a cyclic peptide subarray of cyclized peptides and some linear peptides. Based on this method, the linear peptides in the two subarrays were structurally identical. By generating a linear peptide subarray having linear peptides identical to the peptides that failed to cyclize on the cyclic peptide subarray, the interaction of the linear peptides with the target protein was possible to detect.

Example 11

Peptide Synthesis

Cyclic and linear peptides were supplied by GenScript (Piscataway, N.J.) at >95% purity. To best replicate the linkage between U and the array surface, the peptides were ordered with the side chain of glutamate (U) amidated, hence, making the amino acid a glutamine (Q). 5 mM stock solutions were prepared in water using the peptide weight provided by GenScript.

Example 12

Streptavidin Binding to Peptide Microarray

Slides were bound with 150 mg streptavidin-Cy5 in 30 mL binding buffer for 30 minutes at room temperature.

Binding buffer contained 1% alkali soluble casein and 0.05% tween-20 in 1×TBS, pH 7.4. After 30 minutes, slides were washed twice in 1×TBS buffer for 1 minute, water for 30 seconds, and spun to dryness.

Example 13

Fluorescence Scans/Data Analysis

Cy5 fluorescence intensity of the arrays was measured with MS200 scanner (Roche NimbleGen) at resolution 2 um, wavelength 635 nm, gain 25% and laser intensity 100%. Cy5 signal intensities were extracted using Image Extraction Software (Roche NimbleGen). Data pre-processing, normalization and statistical tests were done in R. Data visualization and analysis were performed with Spotfire 6.5.0 (Tibco, Boston, Mass.) software platform.

Example 14

Surface Plasmon Resonance

Surface plasmon resonance (SPR) experiments were performed on a BIAcore X100 (GE Healthcare). The running buffer was HBS-EP+. To prepare a streptavidin coated chip, 100 ug/mL streptavidin in Acetate 5.0 immobilization buffer was coupled to flow cell 2 of a CM5 chip using the Amine Coupling Kit (GE Healthcare. The chip was then conditioned by flowing a solution containing 0.2 M NaCl and 10 mM NaOH in water over the prepared chip for 60 seconds. The binding affinities of the cyclic and linear peptides were measured against the prepared streptavidin chip using a multiple cycle experiment with base regeneration between each step. Here, seven prepared concentrations of peptide in HBS-EP+ buffer were flowed over the streptavidin chip for 30 seconds and then allowed to dissociate for 60 seconds. Following each peptide concentration, the streptavidin chip was regenerated by flowing 0.2 M NaCl and 10 mM NaOH in water over the chip for 30 seconds followed by a stabilization period of 120 seconds. Kinetic parameters were determined using BIAcore X100 Evaluation Software Version 2.0.1.

Example 15

Random 4mer Library Design

Cyclic and linear peptides were generated according to the methods described in Examples 8-10. All peptides in the library were of the format XXXXU, each X was an independently selected amino acid selected from a specific set of L- and D-amino acids, and U was a glutamate protected on the C-terminus with either an allyl ester (cyclic features) or t-butyl ester (linear features), as described in Example 10. The amino acids included in this design were L-Ser, L-Thr, L-Asn, L-Gln, L-Gly, L-Pro, L-Ala, L-Ile, L-Phe, L-Trp, L-Tyr, L-Val, D-Ala, D-Asn, D-Leu, D-Phe, D-Pro, D-Ser, D-Trp, and D-Tyr. As used herein, lowercase "p" in an amino acid sequence refers to D-proline.

Figure 10:
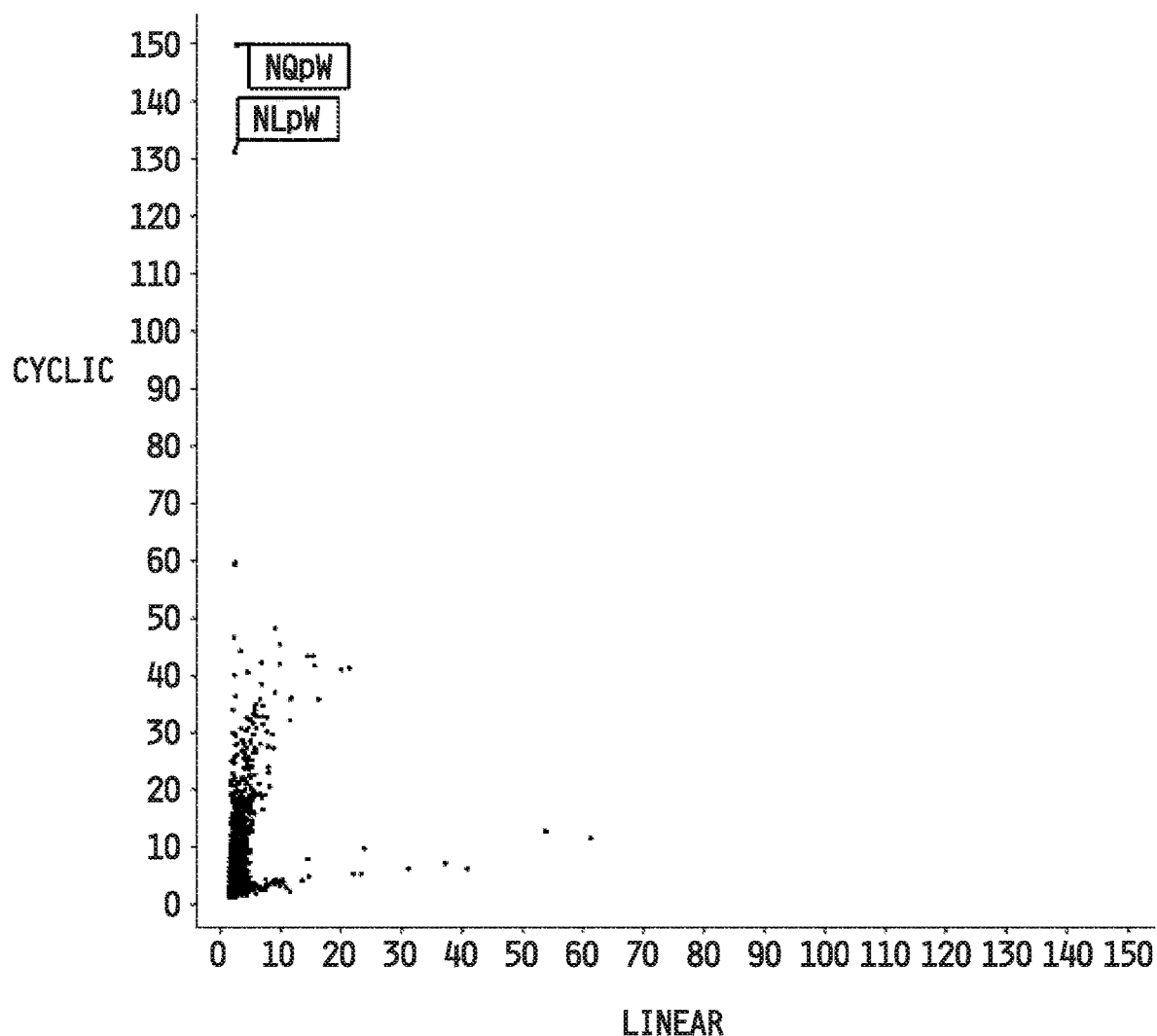
FIG. 10 is a chart showing cyclic versus linear fluorescent intensity for a peptide library of the format XXXXU bound to streptavidin-Cy5.

A streptavidin binding assay for peptides of the format XXXXU was performed according to the methods of Examples 12 and 13. Results are shown in FIG. 10, which is a chart showing cyclic versus linear fluorescent intensity for a peptide library of the format XXXXU bound to streptavidin-Cy5. Each point on the chart represents a unique peptide sequence. All points that fall off of the correlation line represent differential binding between the cyclic and linear conformations of the same sequence. The cylic NQpWU (SEQ ID NO: 83) peptide was identified as having the highest cyclic fluorescent intensity.

Example 16

NQpWQ (SEQ ID NO: 84) SPR Results

Figure 11:
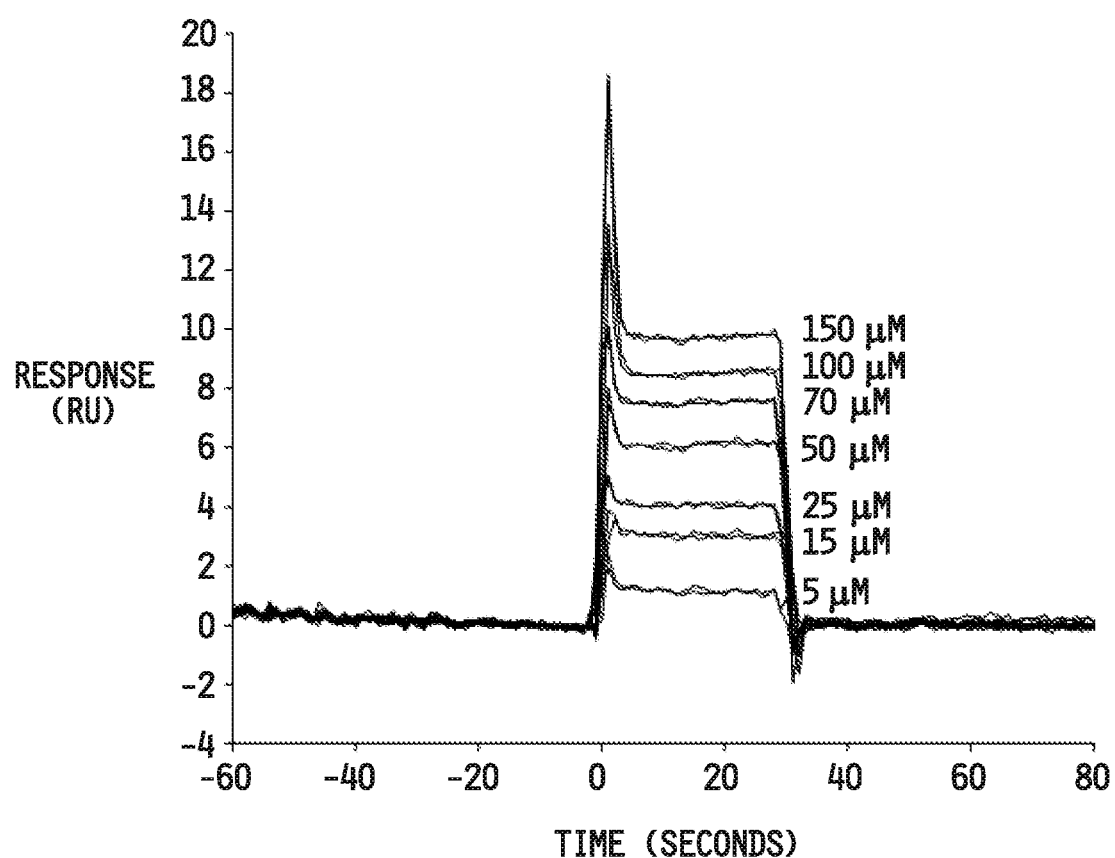
FIG. 11 is a chart showing surface plasmon resonance (SPR) binding curves of a head-to-tail cylic NQpWQ (SEQ ID NO: 84) peptide to a streptavidin coated CM5 BIAcore chip.
Figure 12:
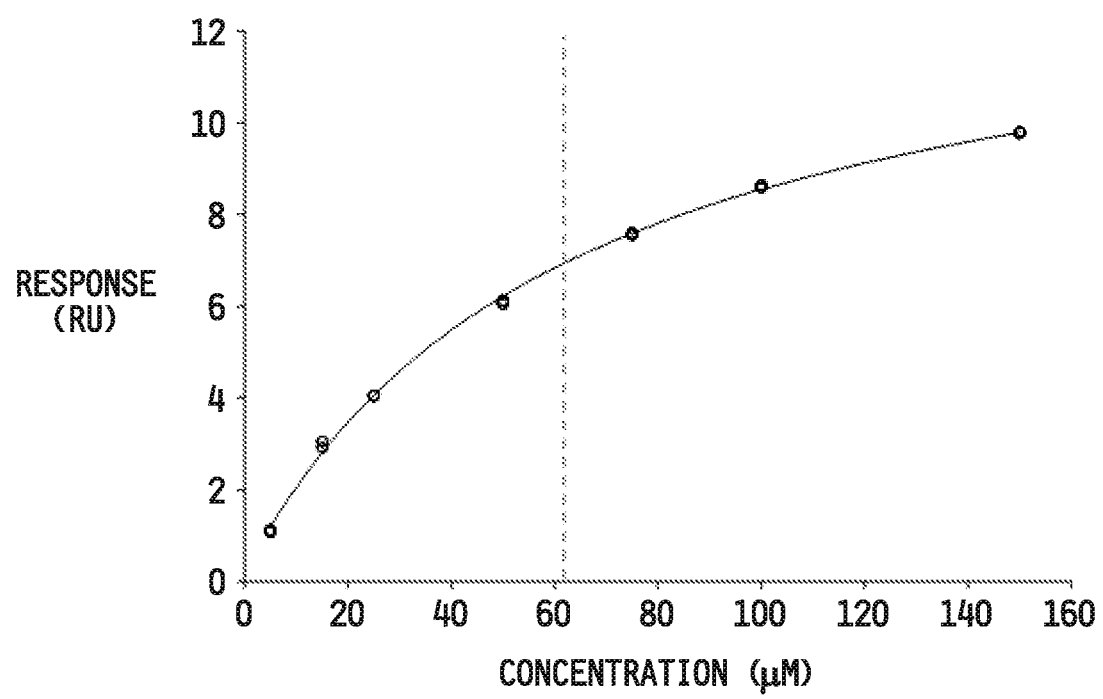
FIG. 12 is a chart showing surface plasmon resonance (SPR) binding of a head-to-tail cylic NQpWQ (SEQ ID NO: 84) peptide to a streptavidin coated CM5 BIAcore chip versus peptide concentration. The dashed line indicates the binding constant.

The head-to-tail cyclic NQpWQ (SEQ ID NO: 84) peptide (obtained according to Example 11) was the subject of a surface plasmon resonance (SPR) binding study according to Example 14. FIG. 11 shows surface plasmon resonance (SPR) binding curves of the head-to-tail cylic NQpWQ (SEQ ID NO: 84) peptide to a streptavidin coated CM5 BIAcore chip. FIG. 12 shows surface plasmon resonance (SPR) binding of the head-to-tail cylic NQpWQ (SEQ ID NO: 84) peptide to a streptavidin coated CM5 BIAcore chip versus peptide concentration. The dashed line indicates the binding constant.

The linear $NH_2$-NQpWQ-COOH (SEQ ID NO: 85) peptide (obtained according to Example 11) was also the subject to an SPR study. While the cylic NQpWQ (SEQ ID NO: 84) peptide had a binding constant ($K_D$) of 61.3 μM, the linear $NH_2$-NQpWQ-COOH (SEQ ID NO: 85) peptide showed no measureable binding activity ($K_D$>2000 μM). The difference in activity between the cyclic NQpWQ (SEQ ID NO: 84) peptide and the linear $NH_2$-NQpWQ-COOH (SEQ ID NO: 85) peptide, each prepared according to Example 11, agrees with the difference in activity between the subarrays of linear and cyclized NQpWU (SEQ ID NO: 83) peptides separately generated on the microarray according to Example 10. This result shows that the cyclization step according to Example 10 was successful.

Example 17

HPQ-Specific Design Library Design

Cyclic and linear peptides were generated according to the methods described in Examples 8-10. All peptides in the library were of the format JXXHPQXXJU (SEQ ID NO: 86), where J was a mixture of all 20 standard amino acids, each X was an independently selected amino acid, and U was a glutamate protected on the C-terminus with either an allyl ester (cyclic features) or t-butyl ester (linear features), as described in Example 10.

Figure 13:
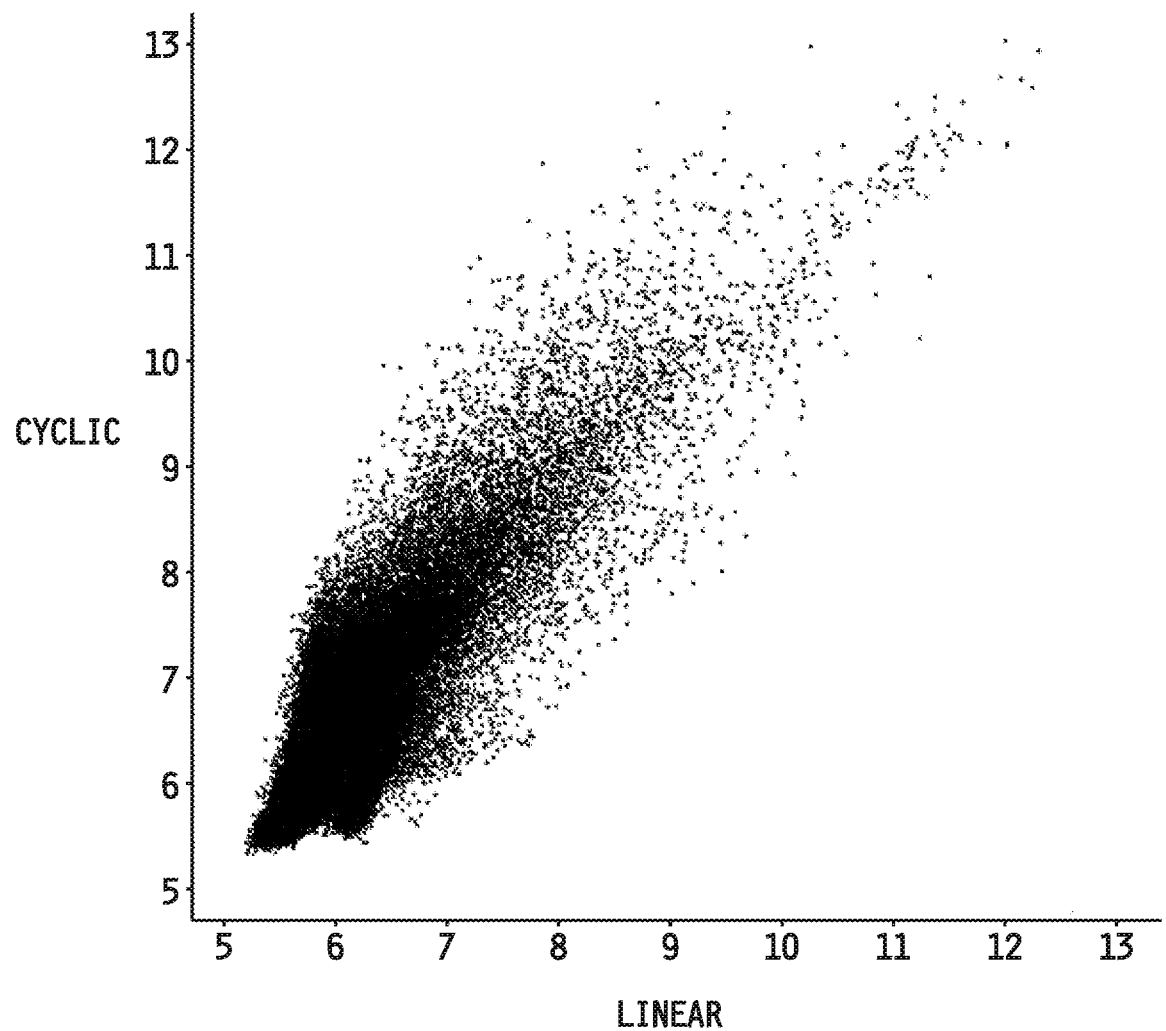
FIG. 13 is a chart showing cyclic versus linear fluorescent intensity for a peptide library of the format JXXHPQXXJU (SEQ ID NO: 86) bound to streptavidin-Cy5.

A streptavidin binding assay for peptides of the format JXXHPQXXJU (SEQ ID NO: 86) was performed according to the methods of Examples 12 and 13. Results are shown in FIG. 13, which is a chart showing cyclic versus linear fluorescent intensity for a peptide library of the format JXXHPQXXJU (SEQ ID NO: 86) bound to streptavidin-Cy5. Each point on the chart represents a unique peptide sequence. All points that fall off of the correlation line represent differential binding between the cyclic and linear conformations of the same sequence.

Figure 14:
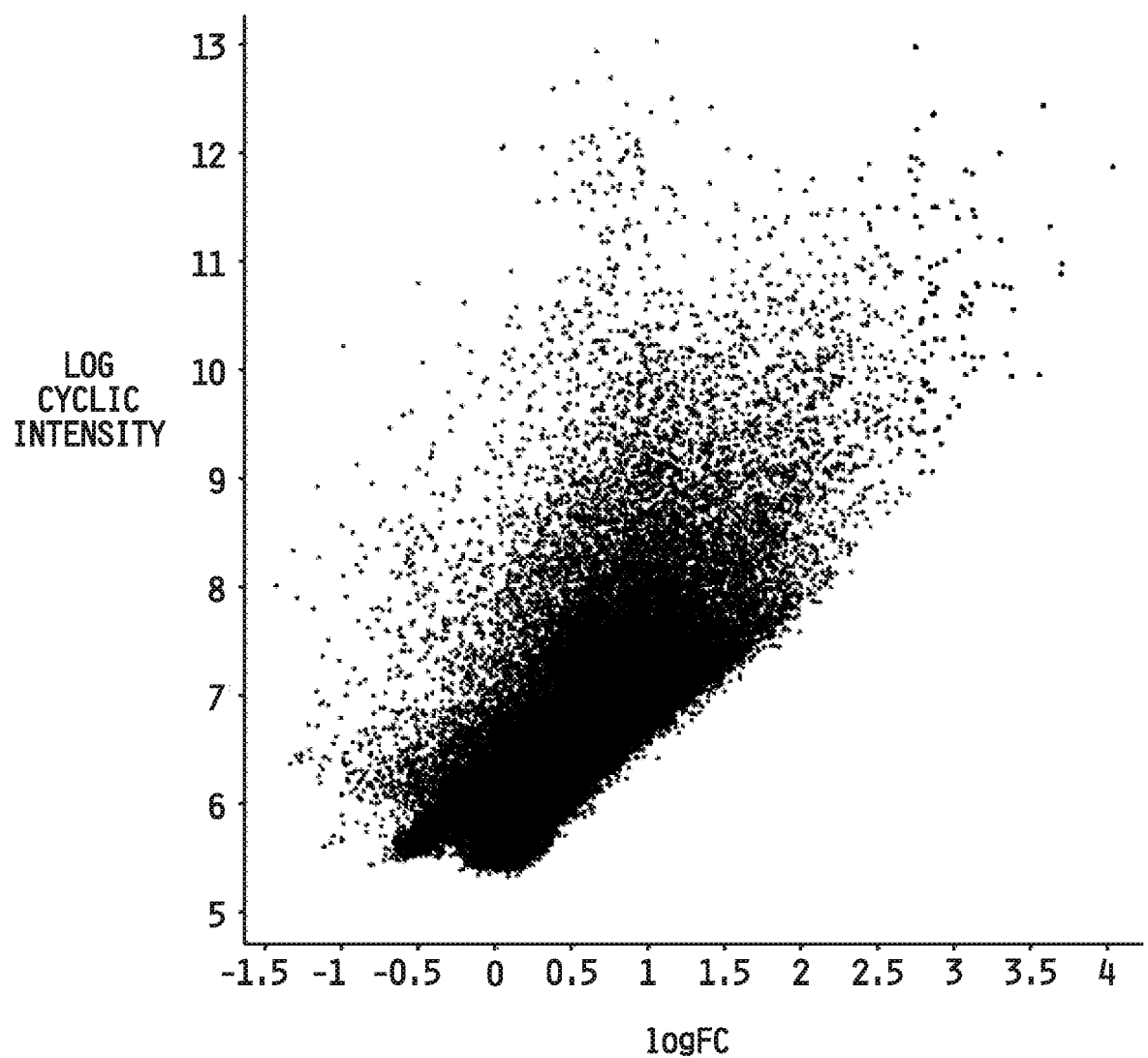
FIG. 14 is a chart showing cyclic fluorescent intensity versus log fold change (log FC) between cyclic and linear fluorescent intensity for a peptide library of the format JXXHPQXXJU (SEQ ID NO: 86) bound to streptavidin-Cy5. The darker points indicate the top 100 JXXHPQXXJU (SEQ ID NO: 86) cyclic peptides.

The data can also be represented for each sequence as a log fold (log FC) change between cyclic and linear fluorescent intensity. As used herein, "log FC" is the log fold change between cyclic and linear fluorescent intensity where a positive log FC indicates a preference for binding to a cyclic peptide and a negative log FC indicates a preference for binding to a linear peptide. The fluorescent intensity data for the peptide library of the format JXXHPQXXJU (SEQ ID NO: 86) are plotted as cyclic fluorescent intensity versus log FC in the chart shown as FIG. 14. Peptides that show no change between cyclic and linear features either have failed to cyclize or did not show a conformational preference. The top 100 hits for this initial HPQ-specific design are shown in Table 1.

TABLE 1

Top 100 streptavidin binding peptides for HPQ-specific design of Example 17.

| | | | |
|---|---|---|---|
| JYDHPQNGJ (SEQ ID NO: 87) | JWDHPQSGJ (SEQ ID NO: 88) | JNQHPQAGJ (SEQ ID NO: 89) | JYEHPQVGJ (SEQ ID NO: 90) |
| JNDHPQNGJ (SEQ ID NO: 91) | JFGHPQGGJ (SEQ ID NO: 92) | JGDHPQNGJ (SEQ ID NO: 93) | JYEHPQKGJ (SEQ ID NO: 94) |
| JYDHPQGGJ (SEQ ID NO: 95) | JWDHPQVGJ (SEQ ID NO: 96) | JWEHPQAGJ (SEQ ID NO: 97) | JNQHPQVGJ (SEQ ID NO: 98) |
| JWDHPQNGJ (SEQ ID NO: 99) | JNGHPQGGJ (SEQ ID NO: 100) | JSGHPQGGJ (SEQ ID NO: 101) | JGQHPQVGJ (SEQ ID NO: 102) |
| JWQHPQVGJ (SEQ ID NO: 103) | JCDHPQNGJ (SEQ ID NO: 104) | JHDHPQGGJ (SEQ ID NO: 105) | JHQHPQVGJ (SEQ ID NO: 106) |
| JFDHPQNGJ (SEQ ID NO: 107) | JWQHPQNGJ (SEQ ID NO: 108) | JWAHPQGGJ (SEQ ID NO: 109) | JSDHPQGGJ (SEQ ID NO: 110) |
| JWDHPQGGJ (SEQ ID NO: 111) | JTDHPQNGJ (SEQ ID NO: 112) | JNQHPQGGJ (SEQ ID NO: 113) | JHQHPQFGJ (SEQ ID NO: 114) |
| JWDHPQAGJ (SEQ ID NO: 115) | JYEHPQGGJ (SEQ ID NO: 116) | JYDHPQVGJ (SEQ ID NO: 117) | JNDHPQVGJ (SEQ ID NO: 118) |
| JWEHPQGGJ (SEQ ID NO: 119) | JYDHPQNNJ (SEQ ID NO: 120) | JWQHPQKGJ (SEQ ID NO: 121) | JHDHPQAGJ (SEQ ID NO: 122) |
| JWDHPQKGJ (SEQ ID NO: 123) | JWGHPQNGJ (SEQ ID NO: 124) | JYDHPQKGJ (SEQ ID NO: 125) | JCGHPQGGJ (SEQ ID NO: 126) |
| JWDHPQRGJ (SEQ ID NO: 127) | JWQHPQFGJ (SEQ ID NO: 128) | JRDHPQAGJ (SEQ ID NO: 129) | JFDHPQVGJ (SEQ ID NO: 130) |
| JGGHPQGGJ (SEQ ID NO: 131) | JADHPQNGJ (SEQ ID NO: 132) | JWGHPQAGJ (SEQ ID NO: 133) | JFDHPQKGJ (SEQ ID NO: 134) |
| JWQHPQGGJ (SEQ ID NO: 135) | JQDHPQNGJ (SEQ ID NO: 136) | JWQHPQRGJ (SEQ ID NO: 137) | JPHHPQSGJ (SEQ ID NO: 138) |
| JHDHPQNGJ (SEQ ID NO: 139) | JNDHPQGGJ (SEQ ID NO: 140) | JHQHPQGGJ (SEQ ID NO: 141) | JNEHPQGGJ (SEQ ID NO: 142) |
| JLDHPQNGJ (SEQ ID NO: 143) | JYQHPQAGJ (SEQ ID NO: 144) | JFGHPQGPJ (SEQ ID NO: 145) | JFEHPQVGJ (SEQ ID NO: 146) |
| JWEHPQKGJ (SEQ ID NO: 147) | JFQHPQGGJ (SEQ ID NO: 148) | JFEHPQGGJ (SEQ ID NO: 149) | JTDHPQGGJ (SEQ ID NO: 150) |
| JYDHPQAGJ (SEQ ID NO: 151) | JWGHPQGPJ (SEQ ID NO: 152) | JFQHPQVGJ (SEQ ID NO: 153) | JSQHPQGGJ (SEQ ID NO: 154) |
| JWQHPQAGJ (SEQ ID NO: 155) | JFDHPQAGJ (SEQ ID NO: 156) | JQGHPQGGJ (SEQ ID NO: 157) | JWDHPQHSJ (SEQ ID NO: 158) |
| JYGHPQGGJ (SEQ ID NO: 159) | JWEHPQRGJ (SEQ ID NO: 160) | JWEHPQNGJ (SEQ ID NO: 161) | JHEHPQFGJ (SEQ ID NO: 162) |
| JRDHPQNGJ (SEQ ID NO: 163) | JWEHPQVGJ (SEQ ID NO: 164) | JQWHPQGGJ (SEQ ID NO: 165) | JYDHPQAPJ (SEQ ID NO: 166) |
| JWGHPQGGJ (SEQ ID NO: 167) | JHQHPQAGJ (SEQ ID NO: 168) | JNDHPQAGJ (SEQ ID NO: 169) | JGGHPQGPJ (SEQ ID NO: 170) |
| JNDHPQNNJ (SEQ ID NO: 171) | JFQHPQAGJ (SEQ ID NO: 172) | JYQHPQVGJ (SEQ ID NO: 173) | JHEHPQGGJ (SEQ ID NO: 174) |
| JYQHPQGGJ (SEQ ID NO: 175) | JWDHPQHGJ (SEQ ID NO: 176) | JFDHPQRGJ (SEQ ID NO: 177) | JHDHPQRGJ (SEQ ID NO: 178) |
| JSDHPQNGJ (SEQ ID NO: 179) | JYDHPQRGJ (SEQ ID NO: 180) | JDDHPQNGJ (SEQ ID NO: 181) | JWNHPQVGJ (SEQ ID NO: 182) |
| JFDHPQGGJ (SEQ ID NO: 183) | JYDHPQSGJ (SEQ ID NO: 184) | JNQHPQNGJ (SEQ ID NO: 185) | JPYHPQSGJ (SEQ ID NO: 186) |

Example 18

Extension of HPQ-Specific Design

Figure 15:
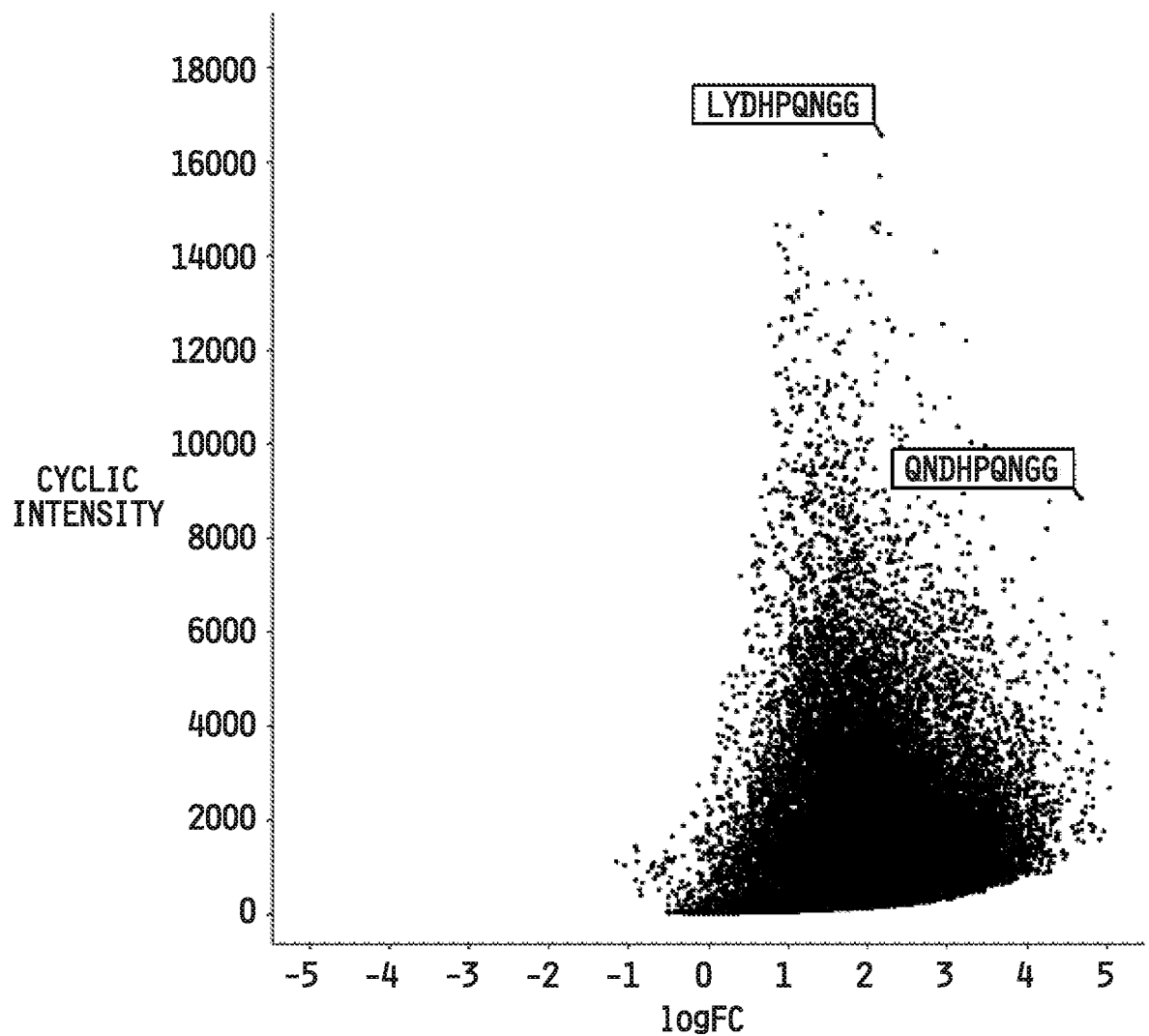
FIG. 15 is a chart showing cyclic fluorescent intensity versus log fold change (log FC) between cyclic and linear fluorescent intensity for a peptide library of the format JXXHPQXXJU (SEQ ID NO: 86) bound to streptavidin-Cy5, where each XXHPQXX (SEQ ID NO: 187) corresponds to one of the top 100 cyclic peptides of the chart shown in FIG. 14, and J is random.

To determine which combinations of J's flanking the XXHPQXX (SEQ ID NO: 187) sequence would yield the highest binding to streptavidin, sequences having all possible combinations of the standard 20 L-amino acids in the J positions were synthesized for the sequences shown in Table 1. A streptavidin binding assay for peptides of Table 1 was performed according to the methods of Examples 12 and 13. Results are shown in FIG. 15, which is a chart showing cyclic fluorescent intensity versus log FC. The cylic LYDHPQNGGU (SEQ ID NO: 188) peptide was identified as having the highest cyclic intensity, and the cyclic QNDHPQNGGU (SEQ ID NO: 189) peptide was identified as a peptide having high cyclic intensity and a high log FC.

Example 19

LYDHPQNGGQ (SEQ ID NO: 190) SPR Results

Figure 16:
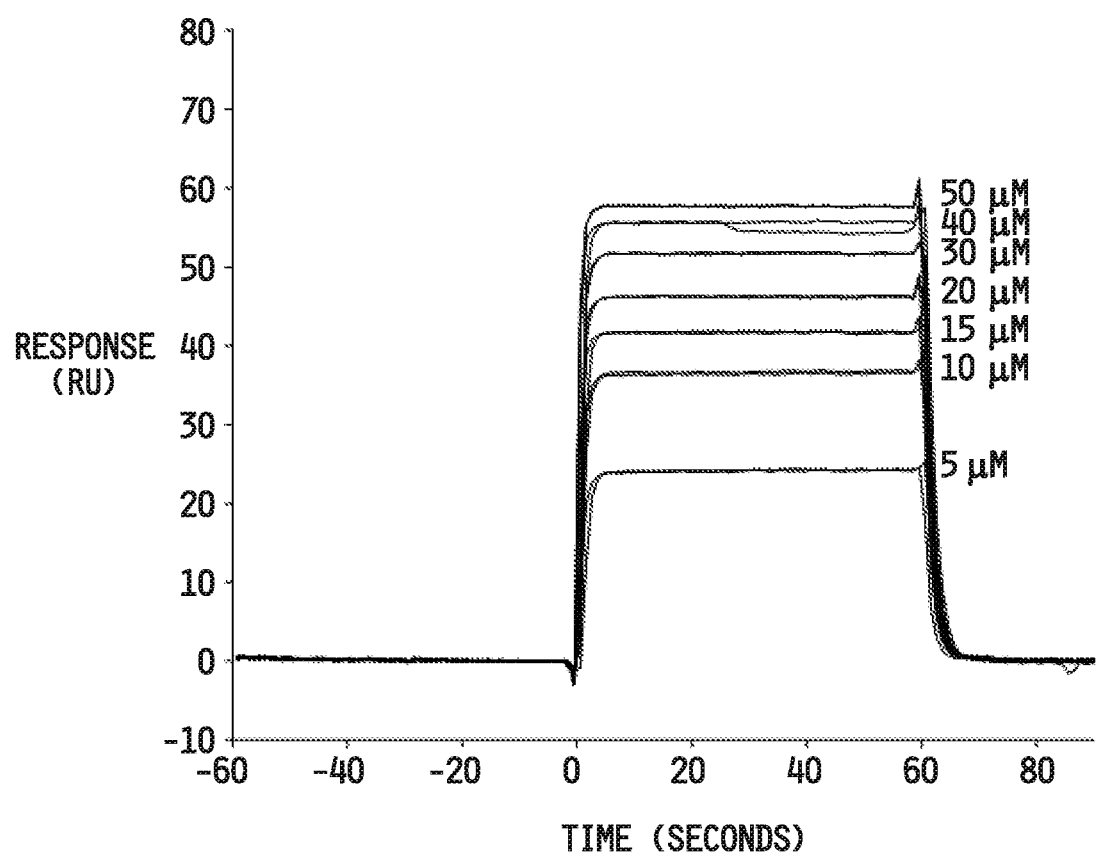
FIG. 16 is a chart showing surface plasmon resonance (SPR) binding curves of a head-to-tail cylic LYDHPQNGGQ (SEQ ID NO: 190) peptide to a streptavidin coated CM5 BIAcore chip at various peptide concentrations.
Figure 17:
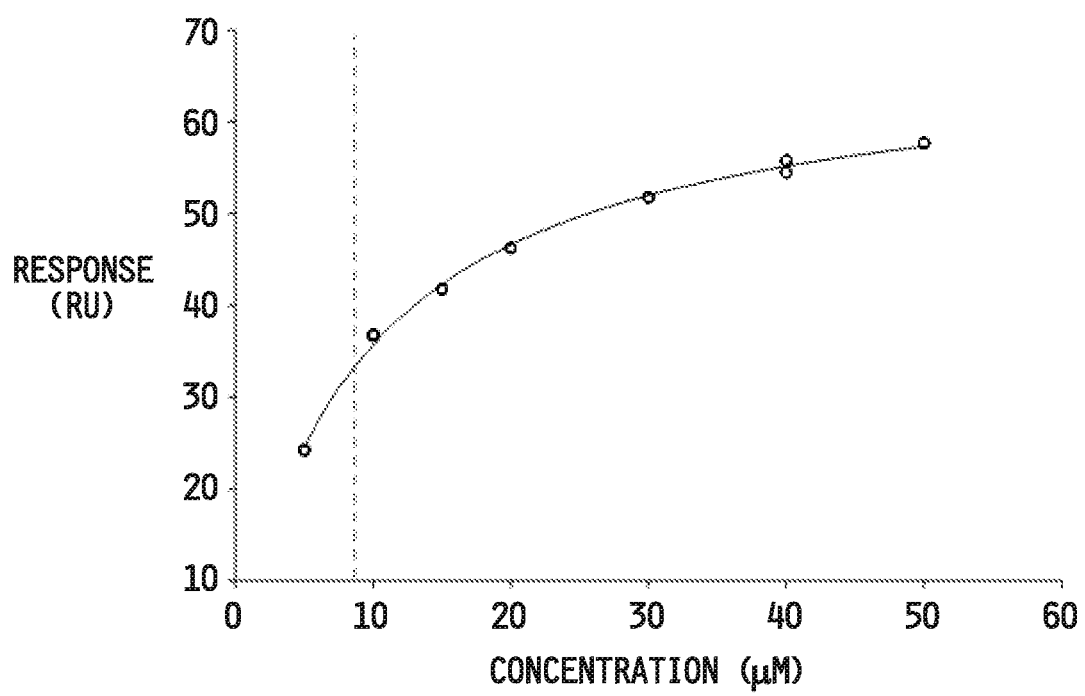
FIG. 17 is a chart showing surface plasmon resonance (SPR) binding of a head-to-tail cylic LYDHPQNGGQ (SEQ ID NO: 190) peptide to a streptavidin coated CM5 BIAcore chip versus peptide concentration. The dashed line indicates the binding constant.

The head-to-tail cyclic LYDHPQNGGQ (SEQ ID NO: 190) peptide (obtained according to Example 11) was the subject of a surface plasmon resonance (SPR) binding study according to Example 14. FIG. 16 shows surface plasmon resonance (SPR) binding curves of the head-to-tail cylic LYDHPQNGGQ (SEQ ID NO: 190) peptide to a streptavidin coated CM5 BIAcore chip. FIG. 17 shows surface plasmon resonance (SPR) binding of the head-to-tail cylic LYDHPQNGGQ (SEQ ID NO: 190) peptide to a streptavidin coated CM5 BIAcore chip versus peptide concentration. The dashed line indicates the binding constant.

Figure 18:
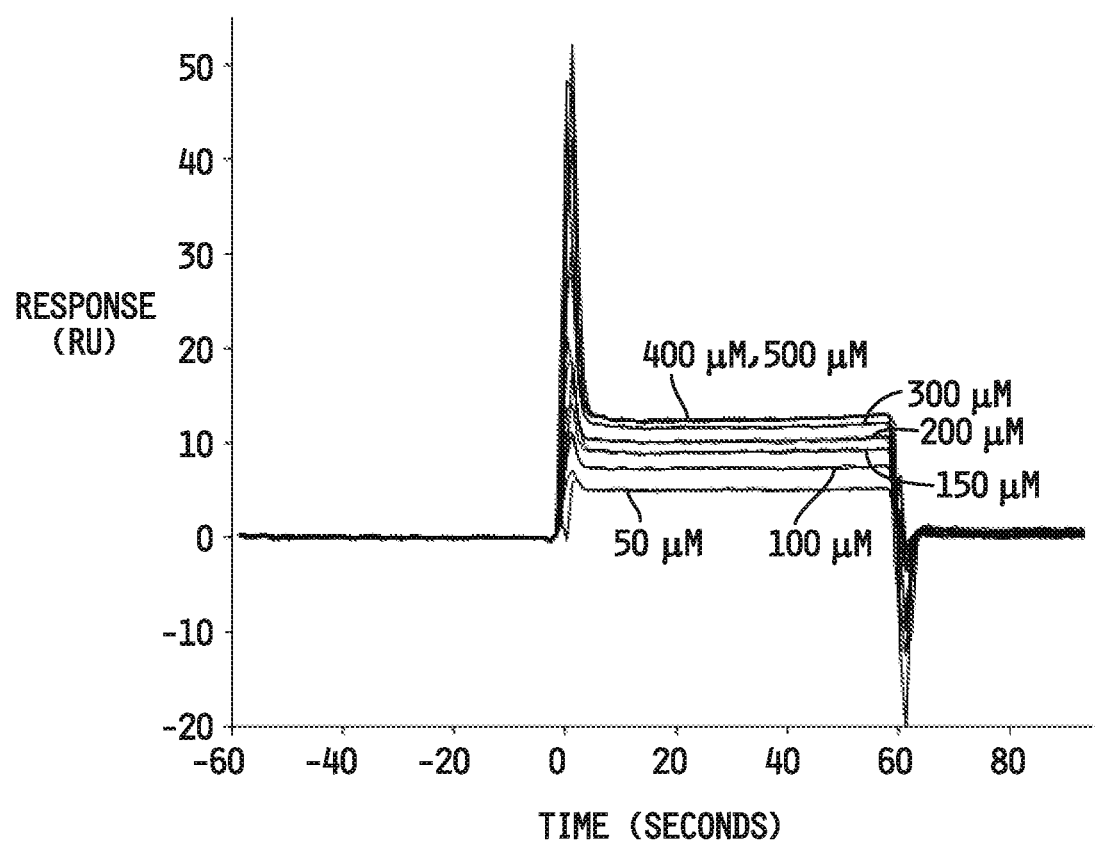
FIG. 18 is a chart showing surface plasmon resonance (SPR) binding curves of a linear $NH_2$-LYDHPQNGGQ-COOH (SEQ ID NO: 191) peptide to a streptavidin coated CM5 BIAcore chip at various peptide concentrations.
Figure 19:
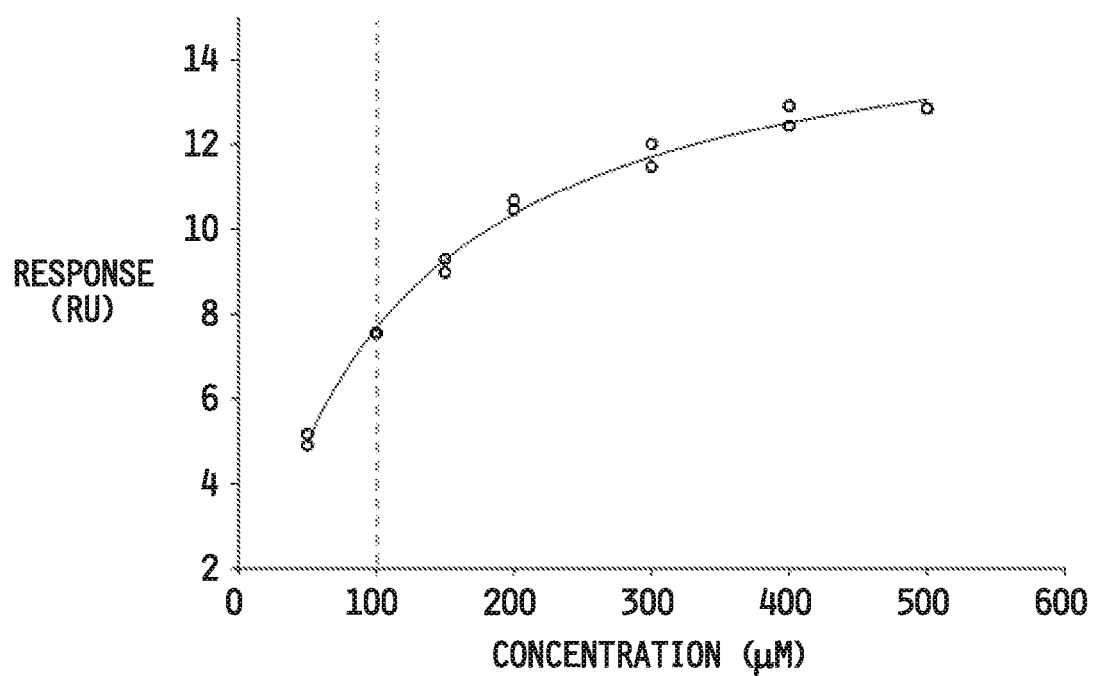
FIG. 19 is a chart showing surface plasmon resonance (SPR) binding of a linear $NH_2$-LYDHPQNGGQ-COOH (SEQ ID NO: 191) peptide to a streptavidin coated CM5 BIAcore chip versus peptide concentration. The dashed line indicates the binding constant.

The linear NH$_2$-LYDHPQNGGQ-COOH (SEQ ID NO: 191) peptide (obtained according to Example 11) was also the subject to an SPR study. FIG. 18 shows surface plasmon resonance (SPR) binding curves of the linear NH$_2$-LYDHPQNGGQ-COOH (SEQ ID NO: 191) peptide to a streptavidin coated CM5 BIAcore chip. FIG. 19 shows surface plasmon resonance (SPR) binding of the linear NH$_2$-LYDHPQNGGQ-COOH (SEQ ID NO: 191) peptide to a streptavidin coated CM5 BIAcore chip versus peptide concentration. The dashed line indicates the binding constant.

While the cylic LYDHPQNGGQ (SEQ ID NO: 190) peptide had a binding constant ($K_D$) of 9.4 µM, the linear NH$_2$-LYDHPQNGGQ-COOH (SEQ ID NO: 191) peptide had a binding constant ($K_D$) of 100 µM. The difference in activity between the cyclic LYDHPQNGGQ (SEQ ID NO: 190) peptide and the linear NH$_2$-LYDHPQNGGQ-COOH (SEQ ID NO: 191) peptide, each prepared according to Example 11, agrees with the difference in activity between the subarrays of linear and cyclized LYDHPQNGGU (SEQ ID NO: 188) peptides separately generated on the microarray according to Example 10. This result shows that the cyclization step according to Example 10 was successful.

Example 20

QNDHPQNGGQ (SEQ ID NO: 192) SPR Results

Figure 20:
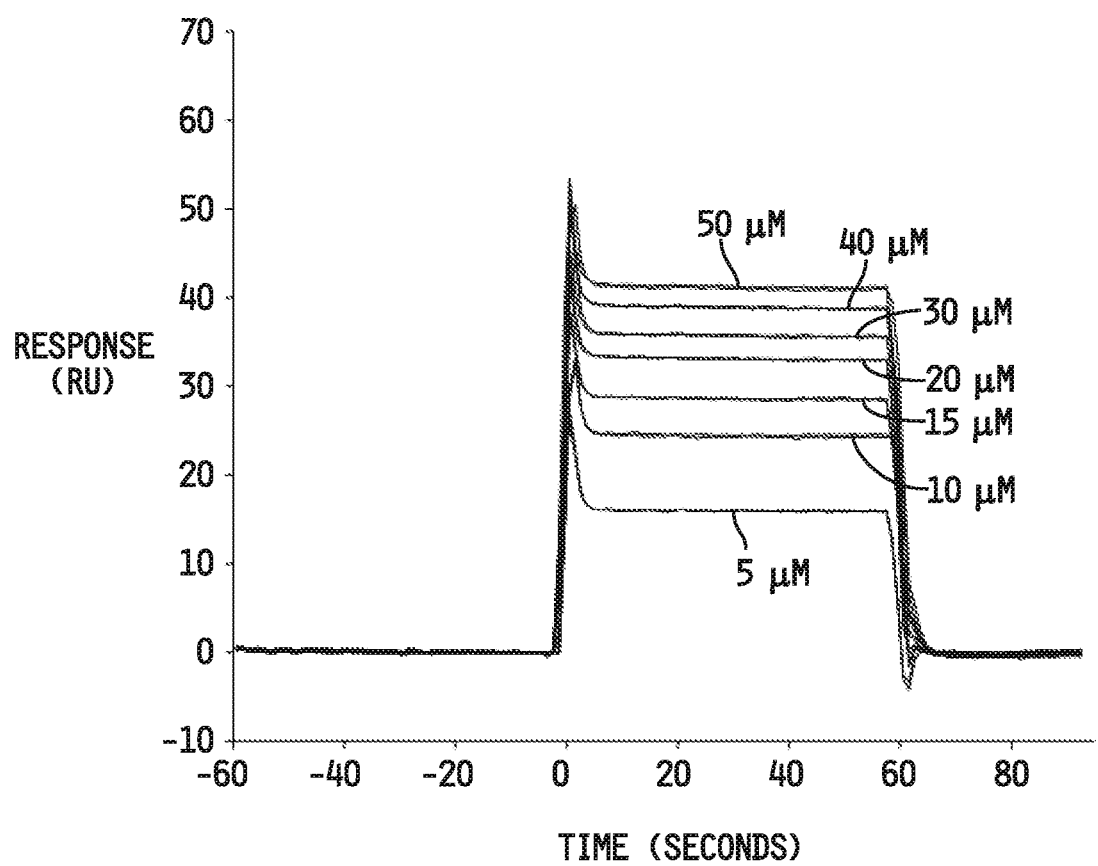
FIG. 20 is a chart showing surface plasmon resonance (SPR) binding curves of a head-to-tail cylic QNDHPQNGGQ (SEQ ID NO: 192) peptide to a streptavidin coated CM5 BIAcore chip at various peptide concentrations.
Figure 21:
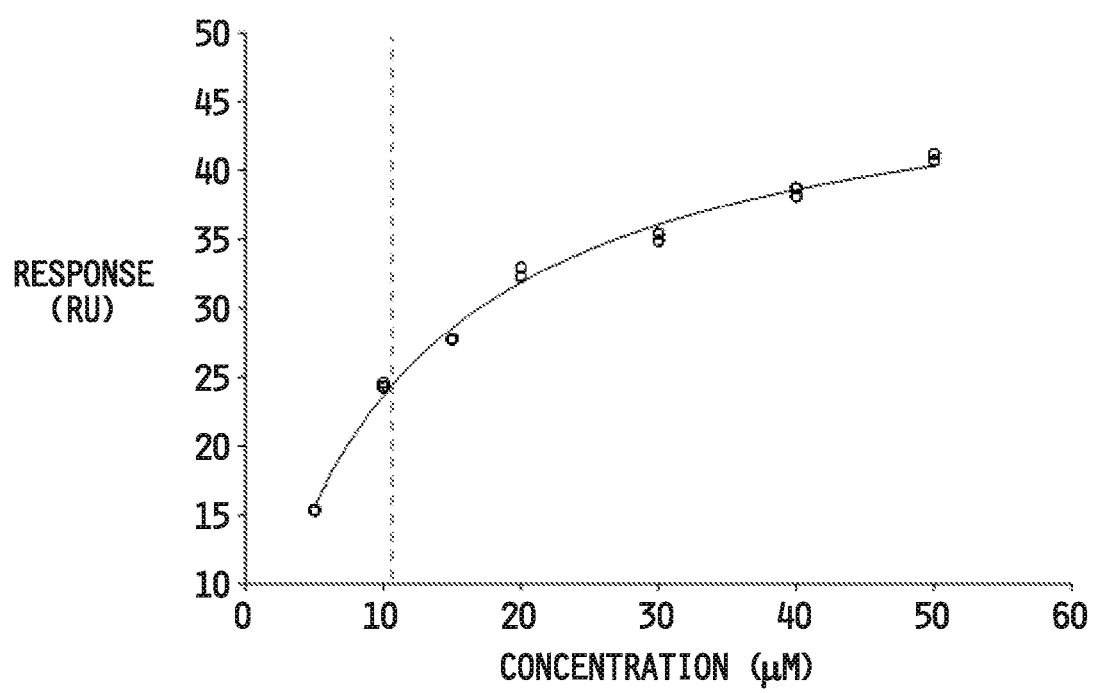
FIG. 21 is a chart showing surface plasmon resonance (SPR) binding of a head-to-tail cylic QNDHPQNGGQ (SEQ ID NO: 192) peptide to a streptavidin coated CM5 BIAcore chip versus peptide concentration. The dashed line indicates the binding constant.

The head-to-tail cyclic QNDHPQNGGQ (SEQ ID NO: 192) peptide (obtained according to Example 11) was the subject of a surface plasmon resonance (SPR) binding study according to Example 14. FIG. 20 shows surface plasmon resonance (SPR) binding curves of the head-to-tail cylic QNDHPQNGGQ (SEQ ID NO: 192) peptide to a streptavidin coated CM5 BIAcore chip. FIG. 21 shows surface plasmon resonance (SPR) binding of the head-to-tail cylic QNDHPQNGGQ (SEQ ID NO: 192) peptide to a streptavidin coated CM5 BIAcore chip versus peptide concentration. The dashed line indicates the binding constant.

Figure 22:
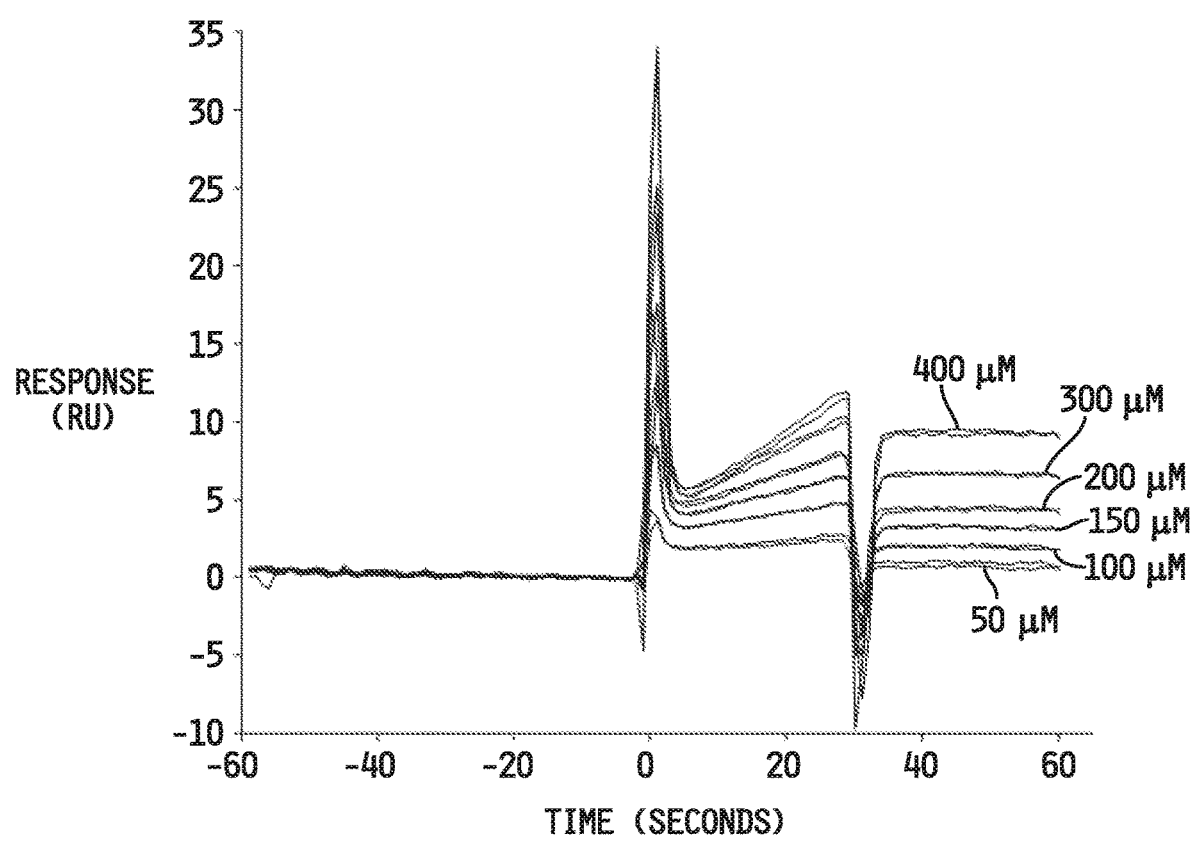
FIG. 22 is a chart showing surface plasmon resonance (SPR) binding curves of a linear $NH_2$-QNDHPQNGGQ-COOH (SEQ ID NO: 193) peptide to a streptavidin coated CM5 BIAcore chip at various peptide concentrations.
Figure 23:
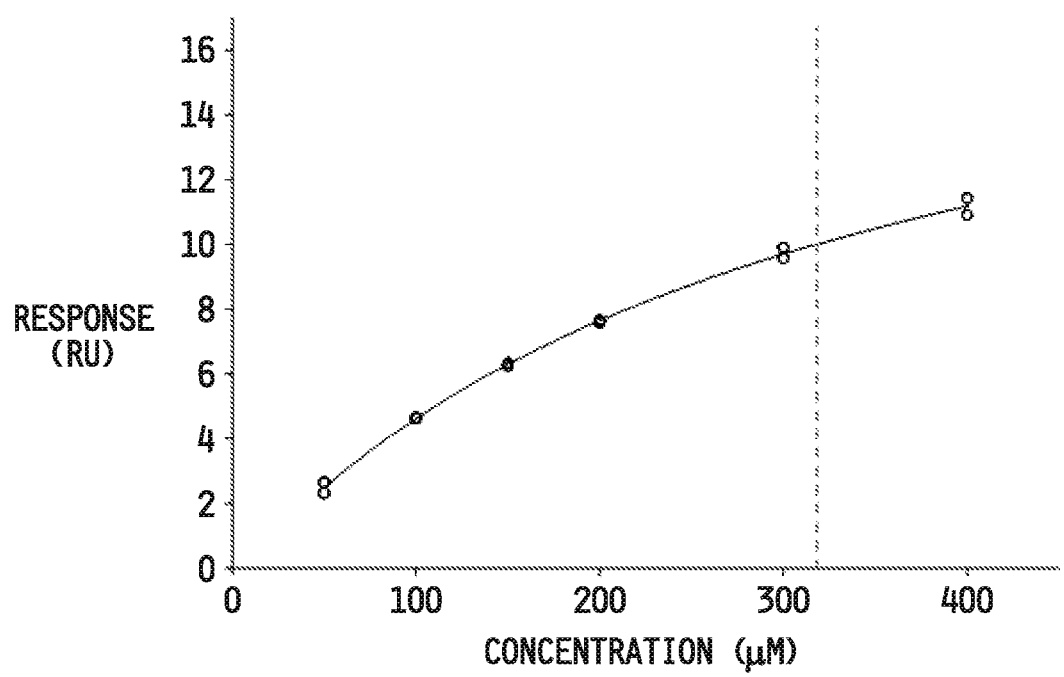
FIG. 23 is a chart showing surface plasmon resonance (SPR) binding of a linear $NH_2$-QNDHPQNGGQ-COOH (SEQ ID NO: 193) peptide to a streptavidin coated CM5 BIAcore chip versus peptide concentration. The dashed line indicates the binding constant.

The linear NH$_2$-QNDHPQNGGQ-COOH (SEQ ID NO: 193) peptide (obtained according to Example 11) was also the subject to an SPR study. FIG. 22 shows surface plasmon resonance (SPR) binding curves of the linear NH$_2$-QNDHPQNGGQ-COOH (SEQ ID NO: 193) peptide to a streptavidin coated CM5 BIAcore chip. FIG. 23 shows surface plasmon resonance (SPR) binding of the linear NH$_2$-QNDHPQNGGQ-COOH (SEQ ID NO: 193) peptide to a streptavidin coated CM5 BIAcore chip versus peptide concentration. The dashed line indicates the binding constant.

While the cylic QNDHPQNGGQ (SEQ ID NO: 192) peptide had a binding constant ($K_D$) of 10.8 µM, the linear NH$_2$-QNDHPQNGGQ-COOH (SEQ ID NO: 193) peptide had a binding constant ($K_D$) of 320 µM. The difference in activity between the cyclic QNDHPQNGGQ (SEQ ID NO: 192) peptide and the linear NH$_2$-QNDHPQNGGQ-COOH (SEQ ID NO: 193) peptide, each prepared according to Example 11, agrees with the difference in activity between the subarrays of linear and cyclized QNDHPQNGGU (SEQ ID NO: 189) peptides separately generated on the microarray according to Example 10. This result shows that the cyclization step according to Example 10 was successful.

What is claimed is:

1. A method of detecting peptide cyclization comprising a) generating a peptide microarray comprising linear peptides coupled to a solid support, wherein each of the linear peptides comprises a variable region and a peptide tag sequence;

wherein:

the peptide tag sequence is fragmented across a first end portion and a second end portion of each linear peptide, and the variable region is between and does not overlap the first end portion and the second end portion;

b) cyclizing at least one of the linear peptides to form at least one cyclic peptide coupled to the solid support by combining the first end portion and the second end portion by forming a peptide bond between the first end portion and the second end portion, wherein after forming the at least one cyclic peptide, the peptide microarray comprises a mixture of linear and cyclized peptides;

c) contacting the peptide microarray comprising the at least one cyclic peptide coupled to the solid support with a detectable target protein;

wherein a binding interaction of the peptide tag sequence with the detectable target protein increases after the cyclizing of the at least one of the linear peptides and the binding interaction has a binding selectivity coefficient of at least 10; and d) measuring the extent of cyclization by detecting the presence of the detectable target protein that is bound to the peptide tag sequence of the at least one cyclic peptide coupled to the solid support;

wherein the variable region of the at least one cyclic peptide is capable of binding to a second target protein.

2. The method of detecting peptide cyclization of claim 1, wherein the detectable target protein is an antibody against the peptide tag sequence.

3. The method of detecting peptide cyclization of claim 1, wherein the detectable target protein is a fluorescent protein and detecting the presence of the detectable target protein comprises fluorescence spectroscopy.

4. The method of detecting peptide cyclization of claim 1, wherein the detectable target protein is an anti-FLAG antibody or an anti-Myc antibody.

5. The method of detecting peptide cyclization of claim 1, wherein at least one of the linear peptides is of formula II

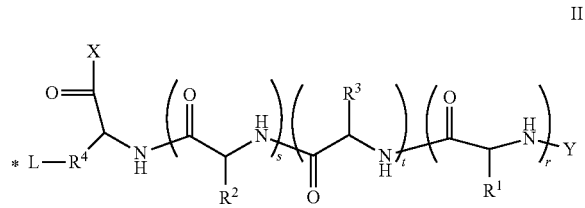

and the at least one cyclic peptide is of formula I

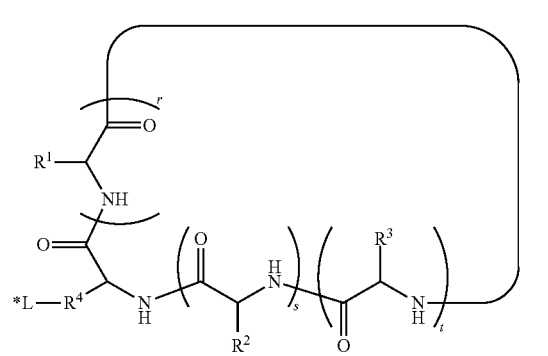

wherein each $R^1$, $R^2$, and $R^3$ is independently a natural amino acid side chain or a non-natural amino acid side chain;

$R^4$ is an amino acid side chain comprising a carboxylic acid, an alcohol, or an amine bonded to L;

L is a bivalent linking group;

X is OH or a C-terminal protecting group;

Y is hydrogen or an N-terminal protecting group;

each r and s is independently an integer from 1 to 50;

t is an integer from 3 to 50;

and * is a point of connection connecting the at least one cyclic peptide of formula I or the linear peptides of Formula II to the solid support, wherein the peptide tag sequence consists of the amino acid residues with the $R^1$, $R^2$ and $R^4$ sidechains, and the variable region consists of the amino acid residues with the $R^3$ sidechains.

6. The method of claim 5, wherein each $R^3$ is defined such that the variable region comprises an amino acid sequence of interest capable of binding to the second target protein and the second target protein differs from the target protein of the peptide tag sequence.

7. The method of claim 6 wherein the second target protein is a therapeutic target.

8. The method of claim 6 wherein t is an integer from 3 to 10.

9. The method of claim 1, wherein the second target protein differs from the target protein of the peptide tag sequence.

10. The method of claim 1 further comprising:
e) contacting the peptide microarray with the second target protein; and
f) detecting the presence of the second target protein that is bound to the variable region of the at least one cyclic peptide.

11. The method of claim 10 wherein the second target protein is a therapeutic target.

12. The method of claim 1, wherein the solid support is a slide or chip selected from glass, carbon composite or plastic.

13. The method of claim 5, wherein L is of the formula

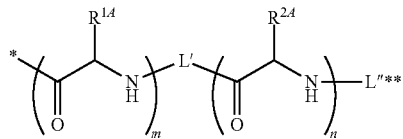

wherein each $R^{1A}$ and $R^{2A}$ is independently a natural amino acid side chain or a non-natural amino acid side chain;
each L' and L" is independently a bivalent linking group or a bond;
m is an integer from 0 to 6;
n is an integer from 0 to 6;
* is the point of connection connecting the at least one cyclic peptide to the solid support having the reactive surface;
and ** is a point of connection connecting L to the rest of the least one cyclic peptide.

14. The method of claim 13, wherein L is 6-aminohexanoic acid.

15. The method of claim 3, wherein the fluorescent protein is labeled with a cyanine dye.

16. The method of claim 1 further comprising
washing the peptide microarray containing the at least one cyclic peptide after contacting the at least one cyclic peptide with the detectable target protein;
wherein:
after the washing the detectable target protein remains bound to the peptide tag sequence after the first end portion and the second end portion combine to cyclize at least one of the linear peptides; and
after the washing the detectable target protein does not remain bound to the peptide tag sequence before the first end portion and the second end portion combine to cyclize at least one of the linear peptides.

17. The method of claim 16, wherein the detectable target protein is a fluorescent protein and detecting the presence of the detectable target protein comprises fluorescence spectroscopy.

* * * * *

SEQUENCE LISTING

<160> NUMBER OF SEQ ID NOS: 258

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Asp Tyr Ala Leu Gln Gly Pro Gly
1               5

<210> SEQ ID NO 2
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Gly Gly Asp Tyr Ala Leu Gln Gly Pro Gly
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Gly Gly Asp Tyr Ala Leu Gln Gly Pro Gly
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Gly Gly Asp Tyr Ala Leu Gln Gly Pro Gly
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Gly Gly Asp Tyr Ala Leu Gln Gly Pro Gly
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Asp Gly Asp Tyr Ala Leu Gln Gly Pro Gly
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Gly Gly Asp Tyr Ala Leu Gln Gly Pro Gly
```

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Cys Gly Asp Tyr Ala Leu Gln Gly Pro Gly
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Gly Gly Asp Tyr Ala Leu Gln Gly Pro Gly
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Gly Gly Asp Tyr Ala Leu Gln Gly Pro Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Gly Gly Asp Tyr Ala Leu Gln Gly Pro Gly
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gly Gly Asp Tyr Ala Leu Gln Gly Pro Gly
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Ile Gly Gly Asp Tyr Ala Leu Gln Gly Pro Gly
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Gly Gly Asp Tyr Ala Leu Gln Gly Pro Gly
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His Gly Gly Asp Tyr Ala Leu Gln Gly Pro Gly
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Gly Gly Asp Tyr Ala Leu Gln Gly Pro Gly
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Gly Gly Asp Tyr Ala Leu Gln Gly Pro Gly
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Gly Gly Asp Tyr Ala Leu Gln Gly Pro Gly
1               5                   10

<210> SEQ ID NO 19

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Trp Gly Asp Tyr Ala Leu Gln Gly Pro Gly
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Gly Gly Asp Tyr Ala Leu Gln Gly Pro Gly
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Gly Gly Asp Tyr Ala Leu Gln Gly Pro Gly
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Gly Gly Asp Tyr Ala Leu Gln Gly Pro Gly
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Tyr Gly Asp Tyr Ala Leu Gln Gly Pro Gly
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

Gly Glu Gly Asp Tyr Ala Leu Gln Gly Pro Gly
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Pro Gly Asp Tyr Ala Leu Gln Gly Pro Gly
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly His Gly Asp Tyr Ala Leu Gln Gly Pro Gly
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Asn Gly Asp Tyr Ala Leu Gln Gly Pro Gly
1               5                   10

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Tyr Ala Leu Gln
1               5

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Gly Asp Tyr Ala Leu Gln Gly Gly Gly
1               5                   10

<210> SEQ ID NO 30
<211> LENGTH: 11
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 30

Trp Asp Gly Asp Tyr Ala Leu Gln Gly Gly Gly
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Gly Gly Asp Tyr Ala Leu Gln Gly Gly Gly Gly
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly Gly Asp Tyr Ala Leu Gln Gly Gly Gly Gly
1               5                   10

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr or Phe
<220> FEATURE:
<221> NAME/KEY: MOD_RES
<222> LOCATION: (2)..(2)
<223> OTHER INFORMATION: Val or Ala

<400> SEQUENCE: 33

Xaa Xaa Leu Gln Gly
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Tyr Ala Leu Gln
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 35

Asp Tyr Val Leu Gln
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asn Tyr Ala Leu Gln
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Tyr Ala Leu Gln
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Pro Tyr Ala Leu Gln
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Tyr Val Leu Gln
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Phe Ala Leu Gln
1               5

<210> SEQ ID NO 41

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Phe Tyr Ala Leu Gln
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Tyr Val Leu Gln
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Tyr Ala Leu Gln
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Phe Ala Leu Gln
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Pro Tyr Val Leu Gln
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46
```

```
Trp Tyr Ala Leu Gln
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Tyr Ala Leu Gln
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His Tyr Ala Leu Gln
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu Phe Ala Leu Gln
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asn Phe Val Leu Gln
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Tyr Phe Leu Gln
1               5

<210> SEQ ID NO 52
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 52

Glu Tyr Val Ala Gln
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Tyr Val Ala Gln
1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Phe Tyr Leu Gln
1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Glu Tyr Phe Leu Gln
1               5

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Leu or Ser

<400> SEQUENCE: 56

Ser Lys Xaa Lys
1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

<223> OTHER INFORMATION: Lys or Arg
<220> FEATURE:
<221> NAME/KEY: MOD_RES
<222> LOCATION: (2)..(2)
<223> OTHER INFORMATION: Ser or Thr

<400> SEQUENCE: 57

Xaa Xaa Lys Leu
1

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Arg Ser Lys Leu
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Ser Lys Leu Ala
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Lys Ser Lys Leu
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Leu Ser Lys Leu
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Ser Lys Leu Gly

```
1               5
```

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Arg Gly Ser Lys Leu
1               5
```

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Arg Ser Lys Ser Lys
1               5
```

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Ser Lys Ser Lys Leu
1               5
```

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Pro Lys Thr Lys Leu
1               5
```

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Arg Ser Lys Leu Ala
1               5
```

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Gly Arg Ser Lys Leu
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Lys Leu Ser Lys
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Phe Thr Lys Ser Lys
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Leu Lys Ser Lys
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Leu Gly Ala Lys
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Arg Ser Lys Leu
1               5

<210> SEQ ID NO 74

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Ser Lys Leu Lys
1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asn Arg Thr Lys Leu
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Arg Thr Lys Leu
1               5

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Gly Gly Arg Ser Lys Leu Ala Gly Gly Gly
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Gly Gly Ala Arg Ser Lys Leu Gly Gly Gly Gly
1               5                   10

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Phe or Tyr
<220> FEATURE:
<221> NAME/KEY: MOD_RES
<222> LOCATION: (2)..(2)
<223> OTHER INFORMATION: Phe, Tyr or Thr

<400> SEQUENCE: 79

Xaa Xaa Leu Gln
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr or Phe

<400> SEQUENCE: 80

Xaa Val Ala Gln
1

<210> SEQ ID NO 81
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr, Leu or Ser

<400> SEQUENCE: 81

Lys Xaa Lys
1

<210> SEQ ID NO 82
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Lys Leu
1

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Pro
<220> FEATURE:
<221> NAME/KEY: MOD_RES
<222> LOCATION: (5)..(5)
<223> OTHER INFORMATION: Glu protected on the C-terminus with either an
      allyl ester (cyclic features) or t-butyl ester
      (linear features)
```

```
<400> SEQUENCE: 83

Asn Gln Pro Trp Glu
1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Pro
<220> FEATURE:
<221> NAME/KEY: MISC_FEATURE
<222> LOCATION: (1)..(5)
<223> OTHER INFORMATION: Cyclic peptide

<400> SEQUENCE: 84

Asn Gln Pro Trp Gln
1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Pro

<400> SEQUENCE: 85

Asn Gln Pro Trp Gln
1               5

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (7)..(8)
<223> OTHER INFORMATION: Any amino acid
<220> FEATURE:
<221> NAME/KEY: MOD_RES
<222> LOCATION: (9)..(9)
<223> OTHER INFORMATION: Any naturally occurring amino acid
<220> FEATURE:
<221> NAME/KEY: MOD_RES
<222> LOCATION: (10)..(10)
<223> OTHER INFORMATION: Glu protected on the C-terminus with either an
      allyl ester (cyclic features) or t-butyl ester
      (linear features)

<400> SEQUENCE: 86
```

```
Xaa Xaa Xaa His Pro Gln Xaa Xaa Xaa Glu
1               5                   10
```

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 87

```
Xaa Tyr Asp His Pro Gln Asn Gly Xaa
1               5
```

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 88

```
Xaa Trp Asp His Pro Gln Ser Gly Xaa
1               5
```

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 89

```
Xaa Asn Gln His Pro Gln Ala Gly Xaa
1               5
```

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 90

Xaa Tyr Glu His Pro Gln Val Gly Xaa
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 91

Xaa Asn Asp His Pro Gln Asn Gly Xaa
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 92

Xaa Phe Gly His Pro Gln Gly Gly Xaa
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 93

Xaa Gly Asp His Pro Gln Asn Gly Xaa
1               5
```

```
<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 94

Xaa Tyr Glu His Pro Gln Lys Gly Xaa
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 95

Xaa Tyr Asp His Pro Gln Gly Gly Xaa
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 96

Xaa Trp Asp His Pro Gln Val Gly Xaa
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
```

```
<222> LOCATION: (9)..(9)
<223> OTHER INFORMATION: Any naturally occurring amino acid

<400> SEQUENCE: 97

Xaa Trp Glu His Pro Gln Ala Gly Xaa
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 98

Xaa Asn Gln His Pro Gln Val Gly Xaa
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 99

Xaa Trp Asp His Pro Gln Asn Gly Xaa
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 100

Xaa Asn Gly His Pro Gln Gly Gly Xaa
1               5

<210> SEQ ID NO 101
<211> LENGTH: 9
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 101

Xaa Ser Gly His Pro Gln Gly Gly Xaa
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 102

Xaa Gly Gln His Pro Gln Val Gly Xaa
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 103

Xaa Trp Gln His Pro Gln Val Gly Xaa
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 104
```

```
Xaa Cys Asp His Pro Gln Asn Gly Xaa
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 105

Xaa His Asp His Pro Gln Gly Gly Xaa
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 106

Xaa His Gln His Pro Gln Val Gly Xaa
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 107

Xaa Phe Asp His Pro Gln Asn Gly Xaa
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 108

Xaa Trp Gln His Pro Gln Asn Gly Xaa
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 109

Xaa Trp Ala His Pro Gln Gly Gly Xaa
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 110

Xaa Ser Asp His Pro Gln Gly Gly Xaa
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 111

Xaa Trp Asp His Pro Gln Gly Gly Xaa
1               5
```

```
<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 112

Xaa Thr Asp His Pro Gln Asn Gly Xaa
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 113

Xaa Asn Gln His Pro Gln Gly Gly Xaa
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 114

Xaa His Gln His Pro Gln Phe Gly Xaa
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
```

```
<221> NAME/KEY: MOD_RES
<222> LOCATION: (9)..(9)
<223> OTHER INFORMATION: Any naturally occurring amino acid

<400> SEQUENCE: 115

Xaa Trp Asp His Pro Gln Ala Gly Xaa
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 116

Xaa Tyr Glu His Pro Gln Gly Gly Xaa
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 117

Xaa Tyr Asp His Pro Gln Val Gly Xaa
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 118

Xaa Asn Asp His Pro Gln Val Gly Xaa
1               5

<210> SEQ ID NO 119
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 119

Xaa Trp Glu His Pro Gln Gly Gly Xaa
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 120

Xaa Tyr Asp His Pro Gln Asn Asn Xaa
1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 121

Xaa Trp Gln His Pro Gln Lys Gly Xaa
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid
```

```
<400> SEQUENCE: 122

Xaa His Asp His Pro Gln Ala Gly Xaa
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 123

Xaa Trp Asp His Pro Gln Lys Gly Xaa
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 124

Xaa Trp Gly His Pro Gln Asn Gly Xaa
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 125

Xaa Tyr Asp His Pro Gln Lys Gly Xaa
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 126

Xaa Cys Gly His Pro Gln Gly Gly Xaa
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 127

Xaa Trp Asp His Pro Gln Arg Gly Xaa
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 128

Xaa Trp Gln His Pro Gln Phe Gly Xaa
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 129

Xaa Arg Asp His Pro Gln Ala Gly Xaa
1               5
```

```
<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 130

Xaa Phe Asp His Pro Gln Val Gly Xaa
 1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 131

Xaa Gly Gly His Pro Gln Gly Gly Xaa
 1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 132

Xaa Ala Asp His Pro Gln Asn Gly Xaa
 1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
```

```
<220> FEATURE:
<221> NAME/KEY: MOD_RES
<222> LOCATION: (9)..(9)
<223> OTHER INFORMATION: Any naturally occurring amino acid

<400> SEQUENCE: 133

Xaa Trp Gly His Pro Gln Ala Gly Xaa
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 134

Xaa Phe Asp His Pro Gln Lys Gly Xaa
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 135

Xaa Trp Gln His Pro Gln Gly Gly Xaa
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 136

Xaa Gln Asp His Pro Gln Asn Gly Xaa
1               5

<210> SEQ ID NO 137
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 137

Xaa Trp Gln His Pro Gln Arg Gly Xaa
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 138

Xaa Pro His His Pro Gln Ser Gly Xaa
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 139

Xaa His Asp His Pro Gln Asn Gly Xaa
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid
```

```
<400> SEQUENCE: 140

Xaa Asn Asp His Pro Gln Gly Gly Xaa
1               5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 141

Xaa His Gln His Pro Gln Gly Gly Xaa
1               5

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 142

Xaa Asn Glu His Pro Gln Gly Gly Xaa
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 143

Xaa Leu Asp His Pro Gln Asn Gly Xaa
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued

```
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 144

Xaa Tyr Gln His Pro Gln Ala Gly Xaa
1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 145

Xaa Phe Gly His Pro Gln Gly Pro Xaa
1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 146

Xaa Phe Glu His Pro Gln Val Gly Xaa
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 147

Xaa Trp Glu His Pro Gln Lys Gly Xaa
```

1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 148

Xaa Phe Gln His Pro Gln Gly Gly Xaa
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 149

Xaa Phe Glu His Pro Gln Gly Gly Xaa
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 150

Xaa Thr Asp His Pro Gln Gly Gly Xaa
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 151

Xaa Tyr Asp His Pro Gln Ala Gly Xaa
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 152

Xaa Trp Gly His Pro Gln Gly Pro Xaa
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 153

Xaa Phe Gln His Pro Gln Val Gly Xaa
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 154

Xaa Ser Gln His Pro Gln Gly Gly Xaa
1               5

<210> SEQ ID NO 155

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 155

Xaa Trp Gln His Pro Gln Ala Gly Xaa
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 156

Xaa Phe Asp His Pro Gln Ala Gly Xaa
1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 157

Xaa Gln Gly His Pro Gln Gly Gly Xaa
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
```

```
<223> OTHER INFORMATION: Any naturally occurring amino acid

<400> SEQUENCE: 158

Xaa Trp Asp His Pro Gln His Ser Xaa
1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 159

Xaa Tyr Gly His Pro Gln Gly Gly Xaa
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 160

Xaa Trp Glu His Pro Gln Arg Gly Xaa
1               5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 161

Xaa Trp Glu His Pro Gln Asn Gly Xaa
1               5

<210> SEQ ID NO 162
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 162

Xaa His Glu His Pro Gln Phe Gly Xaa
1               5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 163

Xaa Arg Asp His Pro Gln Asn Gly Xaa
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 164

Xaa Trp Glu His Pro Gln Val Gly Xaa
1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 165

```
Xaa Gln Trp His Pro Gln Gly Gly Xaa
1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 166

Xaa Tyr Asp His Pro Gln Ala Pro Xaa
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 167

Xaa Trp Gly His Pro Gln Gly Gly Xaa
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 168

Xaa His Gln His Pro Gln Ala Gly Xaa
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 169

Xaa Asn Asp His Pro Gln Ala Gly Xaa
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 170

Xaa Gly Gly His Pro Gln Gly Pro Xaa
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 171

Xaa Asn Asp His Pro Gln Asn Asn Xaa
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 172

Xaa Phe Gln His Pro Gln Ala Gly Xaa
1               5
```

-continued

```
<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 173

Xaa Tyr Gln His Pro Gln Val Gly Xaa
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 174

Xaa His Glu His Pro Gln Gly Gly Xaa
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 175

Xaa Tyr Gln His Pro Gln Gly Gly Xaa
1               5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
```

```
<222> LOCATION: (9)..(9)
<223> OTHER INFORMATION: Any naturally occurring amino acid

<400> SEQUENCE: 176

Xaa Trp Asp His Pro Gln His Gly Xaa
1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 177

Xaa Phe Asp His Pro Gln Arg Gly Xaa
1               5

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 178

Xaa His Asp His Pro Gln Arg Gly Xaa
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 179

Xaa Ser Asp His Pro Gln Asn Gly Xaa
1               5

<210> SEQ ID NO 180
<211> LENGTH: 9
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 180

Xaa Tyr Asp His Pro Gln Arg Gly Xaa
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 181

Xaa Asp Asp His Pro Gln Asn Gly Xaa
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 182

Xaa Trp Asn His Pro Gln Val Gly Xaa
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 183
```

```
Xaa Phe Asp His Pro Gln Gly Gly Xaa
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 184

Xaa Tyr Asp His Pro Gln Ser Gly Xaa
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 185

Xaa Asn Gln His Pro Gln Asn Gly Xaa
1               5

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid

<400> SEQUENCE: 186

Xaa Pro Tyr His Pro Gln Ser Gly Xaa
1               5

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (6)..(7)
<223> OTHER INFORMATION: Any amino acid

<400> SEQUENCE: 187

Xaa Xaa His Pro Gln Xaa Xaa
1               5

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Glu protected on the C-terminus with either an
      allyl ester (cyclic features) or t-butyl ester
      (linear features)

<400> SEQUENCE: 188

Leu Tyr Asp His Pro Gln Asn Gly Gly Glu
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Glu protected on the C-terminus with either an
      allyl ester (cyclic features) or t-butyl ester
      (linear features)

<400> SEQUENCE: 189

Gln Asn Asp His Pro Gln Asn Gly Gly Glu
1               5                   10

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: Cyclic peptide

<400> SEQUENCE: 190

Leu Tyr Asp His Pro Gln Asn Gly Gly Gln
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 191

Leu Tyr Asp His Pro Gln Asn Gly Gly Gln
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: Cyclic peptide

<400> SEQUENCE: 192

Gln Asn Asp His Pro Gln Asn Gly Gly Gln
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gln Asn Asp His Pro Gln Asn Gly Gly Gln
1               5                   10

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MISC_FEATURE
<222> LOCATION: (6)..(6)
<223> OTHER INFORMATION: Side chain coupled to the solid support

<400> SEQUENCE: 194

Trp Asp Tyr Lys Asp Xaa Asp Gln Lys Gly Gly
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MISC_FEATURE
<222> LOCATION: (6)..(6)
<223> OTHER INFORMATION: Side chain coupled to the solid support

<400> SEQUENCE: 195

```
Glu Gln Lys Leu Ile Xaa Glu Glu Asp Trp Gly
1               5                   10
```

<210> SEQ ID NO 196
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

```
Arg Gly Thr Lys Leu
1               5
```

<210> SEQ ID NO 197
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

```
Phe Pro Lys Leu Lys
1               5
```

<210> SEQ ID NO 198
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

```
Lys Leu Lys Tyr Lys
1               5
```

<210> SEQ ID NO 199
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

```
Arg Ala Lys Tyr Lys
1               5
```

<210> SEQ ID NO 200
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

```
Lys Thr Lys Tyr Lys
1               5
```

<210> SEQ ID NO 201
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 201

Gly Tyr Lys Leu Lys
1               5

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Met Met Met Met Met
1               5

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ala Met Met Met Met
1               5

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Pro Met Met Met Met
1               5

<210> SEQ ID NO 205
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Val Met Met Met Met
1               5

<210> SEQ ID NO 206
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gln Met Met Met Met
1               5
```

```
<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Met Ala Met Met Met
1               5

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Met Gln Met Met Met
1               5

<210> SEQ ID NO 209
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Met Pro Met Met Met
1               5

<210> SEQ ID NO 210
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Met Asn Met Met Met
1               5

<210> SEQ ID NO 211
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Pro Ala Met Met Met
1               5

<210> SEQ ID NO 212
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212
```

```
Pro Phe Met Met Met
1               5

<210> SEQ ID NO 213
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Pro Val Met Met Met
1               5

<210> SEQ ID NO 214
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Pro Glu Met Met Met
1               5

<210> SEQ ID NO 215
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Val Ala Met Met Met
1               5

<210> SEQ ID NO 216
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Val Phe Met Met Met
1               5

<210> SEQ ID NO 217
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Pro Val Met Met Met
1               5

<210> SEQ ID NO 218
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 218

Val Glu Met Met Met
1               5

<210> SEQ ID NO 219
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ala Ala Met Met Met
1               5

<210> SEQ ID NO 220
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ala Phe Met Met Met
1               5

<210> SEQ ID NO 221
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ala Val Met Met Met
1               5

<210> SEQ ID NO 222
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ala Glu Met Met Met
1               5

<210> SEQ ID NO 223
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Met Met Met Met
1
```

-continued

```
<210> SEQ ID NO 224
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<223> OTHER INFORMATION: See specification as filed for detailed
      description of substitutions and preferred embodiments

<400> SEQUENCE: 224

Xaa Met Met Met Met Met
1               5

<210> SEQ ID NO 225
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any naturally occurring amino acid
<220> FEATURE:
<223> OTHER INFORMATION: See specification as filed for detailed
      description of substitutions and preferred embodiments

<400> SEQUENCE: 225

Met Xaa Met Met Met Met
1               5

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any naturally occurring amino acid
<220> FEATURE:
<223> OTHER INFORMATION: See specification as filed for detailed
      description of substitutions and preferred embodiments

<400> SEQUENCE: 226

Met Met Xaa Met Met Met
1               5

<210> SEQ ID NO 227
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any naturally occurring amino acid
<220> FEATURE:
<223> OTHER INFORMATION: See specification as filed for detailed
      description of substitutions and preferred embodiments
```

```
<400> SEQUENCE: 227

Met Met Met Xaa Met Met
1               5

<210> SEQ ID NO 228
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any naturally occurring amino acid
<220> FEATURE:
<223> OTHER INFORMATION: See specification as filed for detailed
      description of substitutions and preferred embodiments

<400> SEQUENCE: 228

Met Met Met Met Xaa Met
1               5

<210> SEQ ID NO 229
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any naturally occurring amino acid
<220> FEATURE:
<223> OTHER INFORMATION: See specification as filed for detailed
      description of substitutions and preferred embodiments

<400> SEQUENCE: 229

Met Met Met Met Met Xaa
1               5

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Leu Tyr Asp His Pro Gln Asn Gly Gly
1               5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Gln Asn Asp His Pro Gln Asn Gly Gly
1               5

<210> SEQ ID NO 232
<211> LENGTH: 11
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 232

Gly Asp Tyr Lys Asp Asp Asp Asp Lys Gly Gly
1               5                   10

<210> SEQ ID NO 233
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 233

Glu Gln Lys Leu Ile Ser Glu Glu Asp Leu Gly
1               5                   10

<210> SEQ ID NO 234
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 234

Trp Asp Tyr Lys Asp Asp Asp Asp Lys Gly Gly
1               5                   10

<210> SEQ ID NO 235
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 235

Trp Asp Tyr Lys Asp Phe Asp Asp Lys Gly Gly
1               5                   10

<210> SEQ ID NO 236
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 236

Trp Asp Tyr Lys Asp Phe Asp Gln Lys Gly Gly
1               5                   10

<210> SEQ ID NO 237
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 237

Glu Gln Lys Leu Ile Ser Glu Glu Asp Trp Gly
1               5                   10

<210> SEQ ID NO 238
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Leu Asn Asp Ile Phe Glu Ala Gln Lys Ile Glu Trp His Glu
1               5                   10                  15

<210> SEQ ID NO 239
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 240
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Glu Glu Glu Glu Glu Glu
1               5

<210> SEQ ID NO 241
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Ala Pro Val Pro Tyr Pro Asp Pro Leu Glu Pro Arg
1               5                   10

<210> SEQ ID NO 242
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Asp Tyr Lys Asp Asp Asp Asp Lys
1               5

<210> SEQ ID NO 243
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 243

Tyr Pro Tyr Asp Val Pro Asp Tyr Ala
1               5

<210> SEQ ID NO 244
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

His His His His His His
1               5

<210> SEQ ID NO 245
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Glu Gln Lys Leu Ile Ser Glu Glu Asp Leu
1               5                   10

<210> SEQ ID NO 246
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Lys Glu Thr Ala Ala Ala Lys Phe Glu Arg Gln His Met Asp Ser
1               5                   10                  15

<210> SEQ ID NO 247
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 248
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 248

Ser Leu Ala Glu Leu Leu Asn Ala Gly Leu Gly Gly Ser
1               5                   10

<210> SEQ ID NO 249
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Thr Gln Asp Pro Ser Arg Val Gly
1               5

<210> SEQ ID NO 250
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Trp Ser His Pro Gln Phe Glu Lys
1               5

<210> SEQ ID NO 251
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Cys Cys Pro Gly Cys Cys
1               5

<210> SEQ ID NO 252
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gly Lys Pro Ile Pro Asn Pro Leu Leu Gly Leu Asp Ser Thr
1               5                   10

<210> SEQ ID NO 253
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Tyr Thr Asp Ile Glu Met Asn Arg Leu Gly Lys
1               5                   10

<210> SEQ ID NO 254
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Asp Leu Tyr Asp Asp Asp Asp Lys
1               5

<210> SEQ ID NO 255
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(9)
<223> OTHER INFORMATION: Gly or Ser
<220> FEATURE:
<221> NAME/KEY: MOD_RES
<222> LOCATION: (15)..(15)
<223> OTHER INFORMATION: Allyl-Glu

<400> SEQUENCE: 255

Asp Gln Lys Gly Gly Xaa Xaa Xaa Xaa Trp Asp Tyr Lys Asp Glu
1               5                   10                  15

<210> SEQ ID NO 256
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(9)
<223> OTHER INFORMATION: Gly or Ser
<220> FEATURE:
<221> NAME/KEY: MOD_RES
<222> LOCATION: (15)..(15)
<223> OTHER INFORMATION: Allyl-Glu

<400> SEQUENCE: 256

Glu Glu Asp Trp Gly Xaa Xaa Xaa Xaa Glu Gln Lys Leu Ile Glu
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(9)
<223> OTHER INFORMATION: Gly or Ser

<400> SEQUENCE: 257

Asp Gln Lys Gly Gly Xaa Xaa Xaa Xaa Trp Asp Tyr Lys Asp Gly
1               5                   10                  15

<210> SEQ ID NO 258
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(9)
<223> OTHER INFORMATION: Gly or Ser

<400> SEQUENCE: 258

Glu Glu Asp Trp Gly Xaa Xaa Xaa Xaa Glu Gln Lys Leu Ile Gly
1               5                   10                  15
```